United States Patent
Voss

(10) Patent No.: US 8,821,534 B2
(45) Date of Patent: Sep. 2, 2014

(54) CLIP APPLIER HAVING IMPROVED HEMOSTASIS AND METHODS OF USE

(75) Inventor: Laveille Kao Voss, Belmont, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 276 days.

(21) Appl. No.: 12/961,331

(22) Filed: Dec. 6, 2010

(65) Prior Publication Data

US 2012/0143216 A1   Jun. 7, 2012

(51) Int. Cl.
*A61B 17/08*   (2006.01)

(52) U.S. Cl.
USPC .......................... 606/213; 606/142; 606/158

(58) Field of Classification Search
USPC .......................... 606/139, 142, 157, 158, 213
See application file for complete search history.

(56) References Cited

U.S. PATENT DOCUMENTS

| | | | |
|---|---|---|---|
| 287,046 | A | 10/1883 | Norton |
| 438,400 | A | 10/1890 | Brennen |
| 556,082 | A | 3/1896 | Boeddinghaus |
| 1,088,393 | A | 2/1914 | Backus |
| 1,242,139 | A | 10/1917 | Callahan |
| 1,331,401 | A | 2/1920 | Summers |
| 1,480,935 | A | 1/1924 | Gleason |
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,210,061 | A | 8/1940 | Caminez |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,755,699 | A | 7/1956 | Forster |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,113,379 | A | 12/1963 | Frank |
| 3,120,230 | A | 2/1964 | Skold |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

U.S. Appl. No. 12/608,773, Jan. 7, 2013, Office Action.

(Continued)

*Primary Examiner* — Corrine M McDermott
*Assistant Examiner* — Alexander Orkin
(74) *Attorney, Agent, or Firm* — Workman Nydegger; Randy Shen

(57) ABSTRACT

A hemostasis assembly having a selectively expandable hemostasis member can be used with a medical device and in a method for delivering a closure element through tissue and into an opening formed in, or adjacent to, a wall of a blood vessel or other body lumen of any size while maintaining or improving hemostasis. The medical device and method of use utilizes such an expandable hemostasis member to maintain or improve hemostasis throughout a medical procedure for closing and/or sealing openings through tissues and/or blood vessels.

14 Claims, 51 Drawing Sheets

(56) References Cited

U.S. PATENT DOCUMENTS

| | | |
|---|---|---|
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |

(56) References Cited

U.S. PATENT DOCUMENTS

| | | |
|---|---|---|
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A * | 5/1995 | Weldon et al. ............... 606/213 |
| 5,419,777 A | 5/1995 | Hofling |
| 5,421,832 A | 5/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Lindon et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |

(56) References Cited

U.S. PATENT DOCUMENTS

| | | |
|---|---|---|
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,102 B1 | 4/2001 | Baker et al. |
| 6,231,561 B1 | 5/2001 | Frazier et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |

(56) References Cited

U.S. PATENT DOCUMENTS

| | | |
|---|---|---|
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,623,509 B2 | 9/2003 | Ginn |
| 6,623,510 B2 | 9/2003 | Carley et al. |
| 6,626,918 B1 | 9/2003 | Ginn et al. |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 * | 6/2004 | Goldfarb et al. ............... 606/139 |
| 6,755,842 B2 | 6/2004 | Kanner |
| 6,767,356 B2 | 7/2004 | Kanner et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 * | 5/2007 | Blatter ........................ 606/153 |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |

(56) References Cited

U.S. PATENT DOCUMENTS

| | | |
|---|---|---|
| 7,316,706 B2 | 1/2008 | Bloom et al. |
| 7,322,995 B2 | 1/2008 | Bechman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,780,696 B2 | 8/2010 | Daniel et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 | 2/2011 | Carley et al. |
| 7,887,555 B2 | 2/2011 | Carley et al. |
| 7,887,563 B2 | 2/2011 | Cummins et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelöv |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0208211 A1 | 11/2003 | Kortenbach |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0216057 A1 | 9/2005 | Coleman et al. |
| 2005/0222614 A1 | 10/2005 | Ginn et al. |
| 2005/0228443 A1* | 10/2005 | Yassinzadeh ............... 606/213 |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |

(56) References Cited

U.S. PATENT DOCUMENTS

| | | |
|---|---|---|
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1* | 4/2007 | Lee .............................. 606/213 |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0160958 A1 | 6/2010 | Clark |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Karineimi et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |

(56) References Cited

FOREIGN PATENT DOCUMENTS

| | | |
|---|---|---|
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 13/490,143, Jan. 4, 2013, Office Action.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,470, Dec. 20, 2011, Office Action.
U.S. Appl. No. 12/684,562, Dec. 28, 2011, Office Action.
U.S. Appl. No. 12/684,569, Dec. 20, 2011, Office Action.
U.S. Appl. No. 12/897,358, Jan. 12, 2012, Notice of Allowance.
U.S. Appl. No. 12/941,809, Dec. 13, 2011, Office Action.
U.S. Appl. No. 12/945,646, Oct. 26, 2011, Office Action.
U.S. Appl. No. 12/955,859, Dec. 15, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/947,809, Jan. 30, 2012, Office Action.
U.S. Appl. No. 12/966,923, Feb. 3, 2012, Notice of Allowance.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 13/030,922, filed Feb. 18, 2011, Cummins.
U.S. Appl. No. 13/039,087, filed Mar. 2, 2011, Palermo et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.

(56) References Cited

OTHER PUBLICATIONS

U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No: 1978-B8090A.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No.5, Deparment of Anesthesia, Children's Hospital, Boston, MA.
E Pikoulis et al, Arterial reconstruction with vascular clips is safe and quicker than sutured repair, Cardiovascular Surgery, Dec 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.

Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

(56) References Cited

OTHER PUBLICATIONS

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/264,306, Feb. 16, 2011, Issue Notification.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/356,214, Feb. 23, 2011, Issue Notification.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.

(56) References Cited

OTHER PUBLICATIONS

U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007 Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/3961,41, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.

(56) References Cited

OTHER PUBLICATIONS

U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 12/945,646, Jan. 20, 2011, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/114,031, Mar. 6, 2012, Office Action.
U.S. Appl. No. 12/135,858, Feb. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/608,769, Feb. 10, 2012, Office Action.
U.S. Appl. No. 12/642,319, Feb. 27, 2012, Office Action.
U.S. Appl. No. 12/684,400, Feb. 13, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/897,358, Mar. 5, 2012, Notice of Allowance.
U.S. Appl. No. 12/945,646, Feb. 21, 2012, Notice of Allowance.
U.S. Appl. No. 12/973,204, Mar. 7, 2012, Notice of Allowance.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 11/532576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 10/682,459, Apr. 1, 2011, Notice of Allowance.
U.S. Appl. No. 12/403,277, Mar. 31, 2011, Office Action.
U.S. Appl. No. 12/113,851, Mar. 29, 2012, Office Action.
U.S. Appl. No. 12/114,091, Apr. 5, 2012, Office Action.
U.S. Appl. No. 12/403,277, Apr. 3, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/987,792, Mar. 13, 2012, Office Action.
U.S. Appl. No. 10/147,774, Apr. 6, 2011, Issue Notification.
U.S. Appl. No. 12/122,603, Apr. 22, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 13/308,227, filed Nov. 30, 2011, Yibarren.
U.S. Appl. No. 11/390,586, May 3, 2012, Notice of Allowance.
U.S. Appl. No. 12/684,542, Apr. 16, 2012, Office Action.
U.S. Appl. No. 12/688,065, Apr. 26, 2012, Office Action.
U.S. Appl. No. 12/897,358, May 2, 2012, Issue Notification.
U.S. Appl. No. 12/114,031, May 11, 2011, Office Action.
U.S. Appl. No. 12/143,020, May 11, 2011, Office Action.
U.S. Appl. No. 13/028,041, filed Feb. 15, 2011, Von Oepen.
U.S. Appl. No. 13/112,618, filed May 20, 2011, Gianotti et al.
U.S. Appl. No. 13/112,631, filed May 20, 2011. Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 12/143,020, May 30, 2012, Issue Notification.
U.S. Appl. No. 12/393,877, May 21, 2012, Office Action.
U.S. Appl. No. 12/608,773, Jun. 7, 2012, Office Action.
U.S. Appl. No. 12/684,400, May 9, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 13/026,989, Jun. 8, 2012, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 11/675,462, Aug. 15, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/608,773, Jul. 20, 2012, Office Action.
U.S. Appl. No. 12/684,562, Aug. 21, 2012, Office Action.
U.A. Appl. No. 12/684,569, Jul. 30, 2012, Office Action.
U.S. Appl. No. 12/850,242, Aug. 6, 2012, Office Action.
U.S. Appl. No. 12/955,859, Aug. 6, 2012, Office Action.
U.S. Appl. No. 13/039,087, Jul. 17, 2012, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 12/548,274, Sep. 10, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/987,792, Sep. 17, 2012, Office Action.
U.S. Appl. No. 13/026,989, Sep. 16, 2011, Office Action.
U.S. Appl. No. 12/122,603, Sep. 23, 2011, Office Action.
U.S. Appl. No. 12/393,877, Sep. 29 2011, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 12/338,977, Nov. 28, 2012, Office Action.
U.S. Appl. No. 13/030,922, Dec. 18, 2012, Office Action
U.S. Appl. No. 11/396,141, Apr. 30, 2013, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 11/344,891, Jan. 22, 2013, Notice of Allowance.
U.S. Appl. No. 11/744,089, Apr. 15, 2013, Office Action.
U.S. Appl. No. 11/852,190, Apr. 24, 2013, Office Action.
U.S. Appl. No. 12/402,398, Mar. 13, 2013, Notice of Allowance.
U.S. Appl. No. 12/848,642, Apr. 26, 2013, Office Action.
U.S. Appl. No. 12/850,242, Apr. 18, 2013, Office Action.
U.S. Appl. No. 13/028,041, Jan. 4, 2013, Restriction Requirement.
U.S. Appl. No. 13/028,041, Feb. 26, 2013, Office Action.
U.S. Appl. No. 13/030,922, Jan. 31, 2013, Office Action.
U.S. Appl. No. 13/052,634, Feb. 8, 2013, Restriction Requirement.
U.S. Appl. No. 13/052,634, Apr. 22, 2013, Office Action.
U.S. Appl. No. 13/112,618, Mar. 29, 2013, Restriction Requirement.
U.S. Appl. No. 13/112,631, Mar. 29, 2013, Restriction Requirement.
U.S. Appl. No. 13/153,594, Jan. 29, 2013, Office Action.
U.S. Appl. No. 13/308,227, Apr. 10, 2013, Office Action.
U.S. Appl. No. 13/488,233, Feb. 5, 2013, Notice of Allowance.

(56) References Cited

OTHER PUBLICATIONS

U.S. Appl. No. 13/490,143, Apr. 29, 2013, Notice of Allowance.
U.S. Appl. No. 13/525,839, Apr. 1, 2013, Office Action.
U.S. Appl. No. 13/615,547, Jan. 18, 2013, Office Action.
U.S. Appl. No. 13/615,547, Apr. 12, 2013, Notice of Allowance.
U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 12/338,977, Jun. 19, 2013, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 10/786,444, Jul. 11, 2013, Notice of Allowance.
U.S. Appl. No. 10/908,721, Jul. 18, 2013, Notice of Allowance.
U.S. Appl. No. 11/396,141, Aug. 21, 2013, Office Action.
U.S. Appl. No. 11/411,925, Oct. 1, 2013, Office Action.
U.S. Appl. No. 11/427,309, Sep. 25, 2013, Issue Notification.
U.S. Appl. No. 11/532,325, Jul. 17, 2013, Office Action.
U.S. Appl. No. 11/744,089, Aug. 8, 2013, Notice of Allowance.
U.S. Appl. No. 12/106,928, Jun. 28, 2013, Office Action.
U.S. Appl. No. 12/106,937, Jun. 28, 2013, Office Action.
U.S. Appl. No. 12/850,242, Aug. 6, 2013, Notice of Allowance.
U.S. Appl. No. 12/941,809, Jul. 3, 2013, Office Action.
U.S. Appl. No. 12/955,859, Aug. 1, 2013, Notice of Allowance.
U.S. Appl. No. 13/026,989, Aug. 23, 2013, Office Action.
U.S. Appl. No. 13/028,041, Aug. 21, 2013, Notice of Allowance.
U.S. Appl. No. 13/030,922, Jul. 18, 2013, Office Action.
U.S. Appl. No. 13/308,227, Sep. 11, 2013, Office Action.
U.S. Appl. No. 13/525,839, Jul. 15, 2013, Notice of Allowance.
U.S. Appl. No. 14/246,926, filed Apr. 7. 2014, Carley et al.
U.S. Appl. No. 14/246,973, filed Apr. 1, 2014, Carley et al.
Turn—macmillandictionary.com/dictionary.american/turn.
Turn-Merriam-webster.com/dictionary/turn.
U.S. Appl. No. 11/113,549, Mar. 14, 2014, Notice of Allowance.
U.S. Appl. No. 11/396,141, Nov. 4, 2013, Notice of Allowance.
U.S. Appl. No. 11/396,141, Mar. 19, 2014, Issue Notification.
U.S. Appl. No. 11/411,925, Feb. 5, 2014, Notice of Allowance.
U.S. Appl. No. 11/455,993, Jan. 29, 2014, Office Action.
U.S. Appl. No. 11/532,325, Dec. 2, 2013, Office Action.
U.S. Appl. No. 11/674,930, Apr. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/106,937, Jan. 22, 2014, Office Action.
U.S. Appl. No. 12/113,851, Mar. 17, 2014, Office Action.
U.S. Appl. No. 12/114,031, Mar. 10, 2014, Office Action.
U.S. Appl. No. 12/122,603, Nov. 20, 2013, Office Action.
U.S. Appl. No. 12/403,277, Jan. 27, 2014, Office Action.
U.S. Appl. No. 12/642,319, Dec. 16, 2013, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014. Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/112,618, Nov. 20, 2013, Office Action.
U.S. Appl. No. 13/112,631, Dec. 2, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 11/411,925, Jun. 4, 2014, Issue Notification.
U.S. Appl. No. 11/852,190, Jun. 4, 2014, Issue Notification.
U.S. Appl. No. 12/122,603, Apr. 30, 2014, Office Action.
U.S. Appl. No. 12/642,319, May 27, 2014, Notice of Allowance.
U.S. Appl. No. 12/848,642, Jun. 4, 2014, Issue Notification.
U.S. Appl. No. 12/941,809, Jun. 4, 2014, Issue Notification.
U.S. Appl. No. 12/987,792, Jun. 11, 2014, Office Action.

* cited by examiner

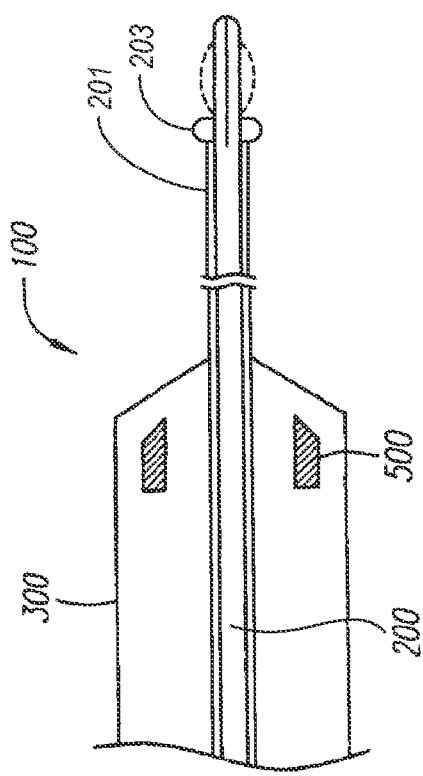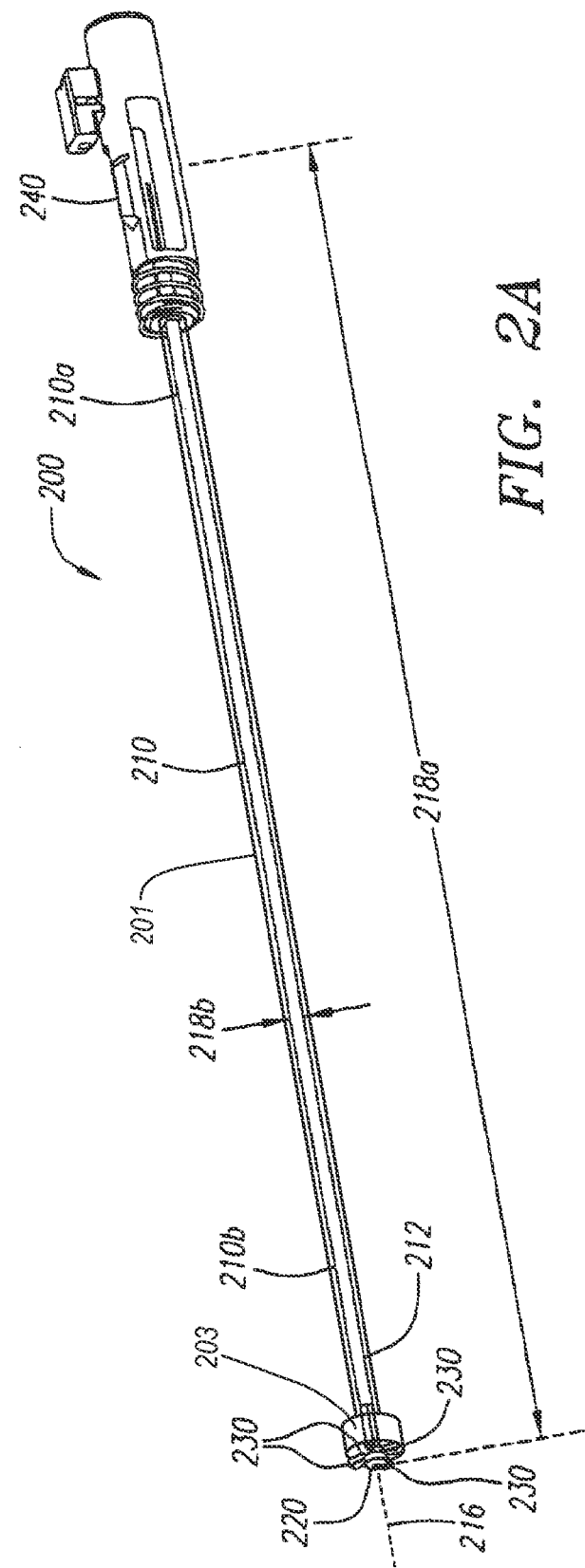

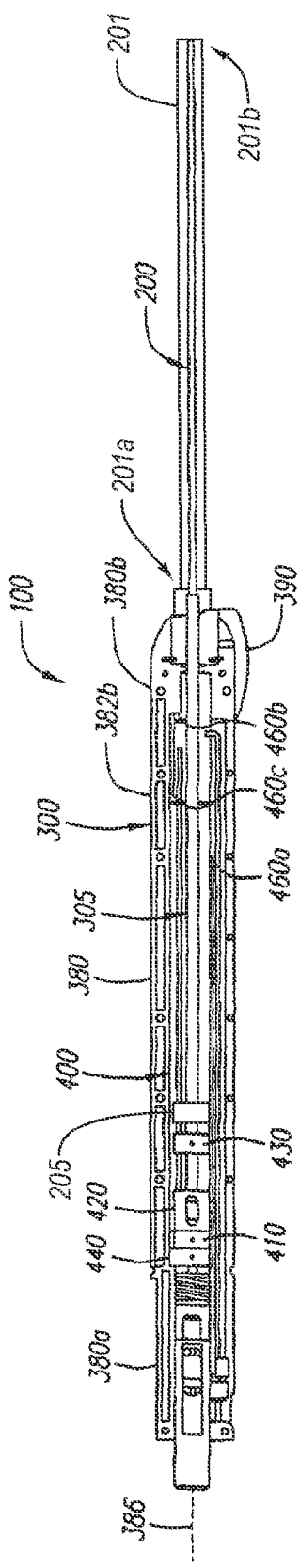
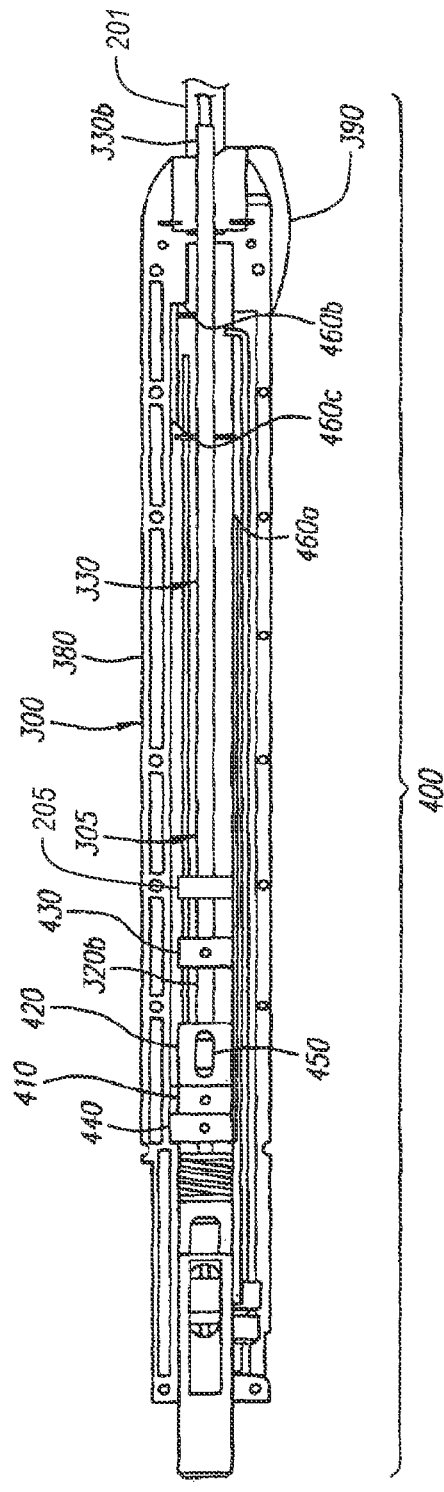
FIG. 4A
FIG. 4B

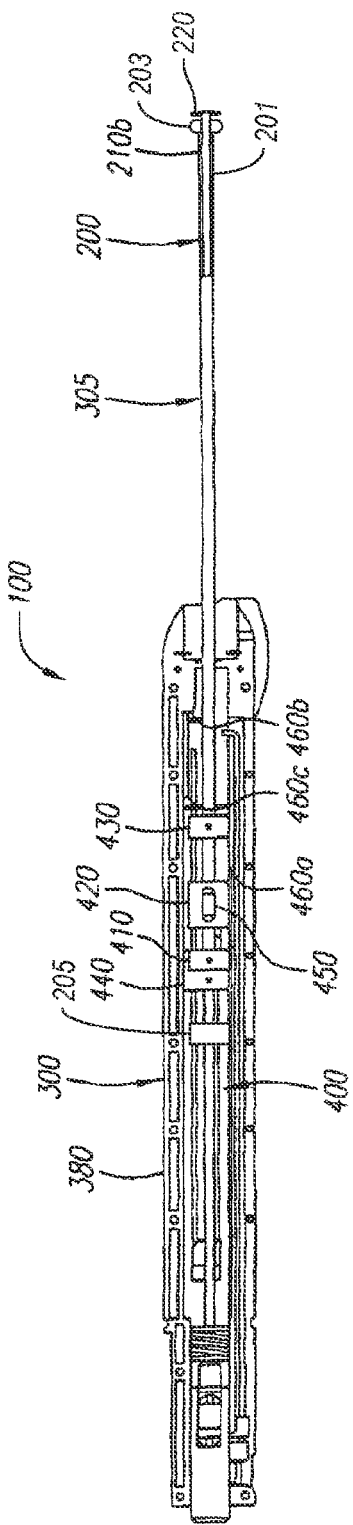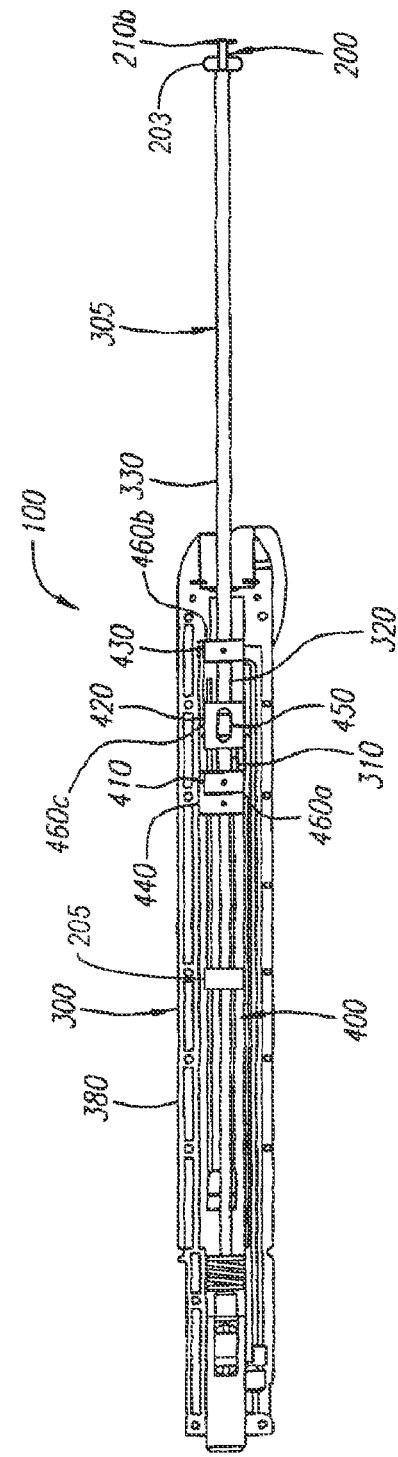

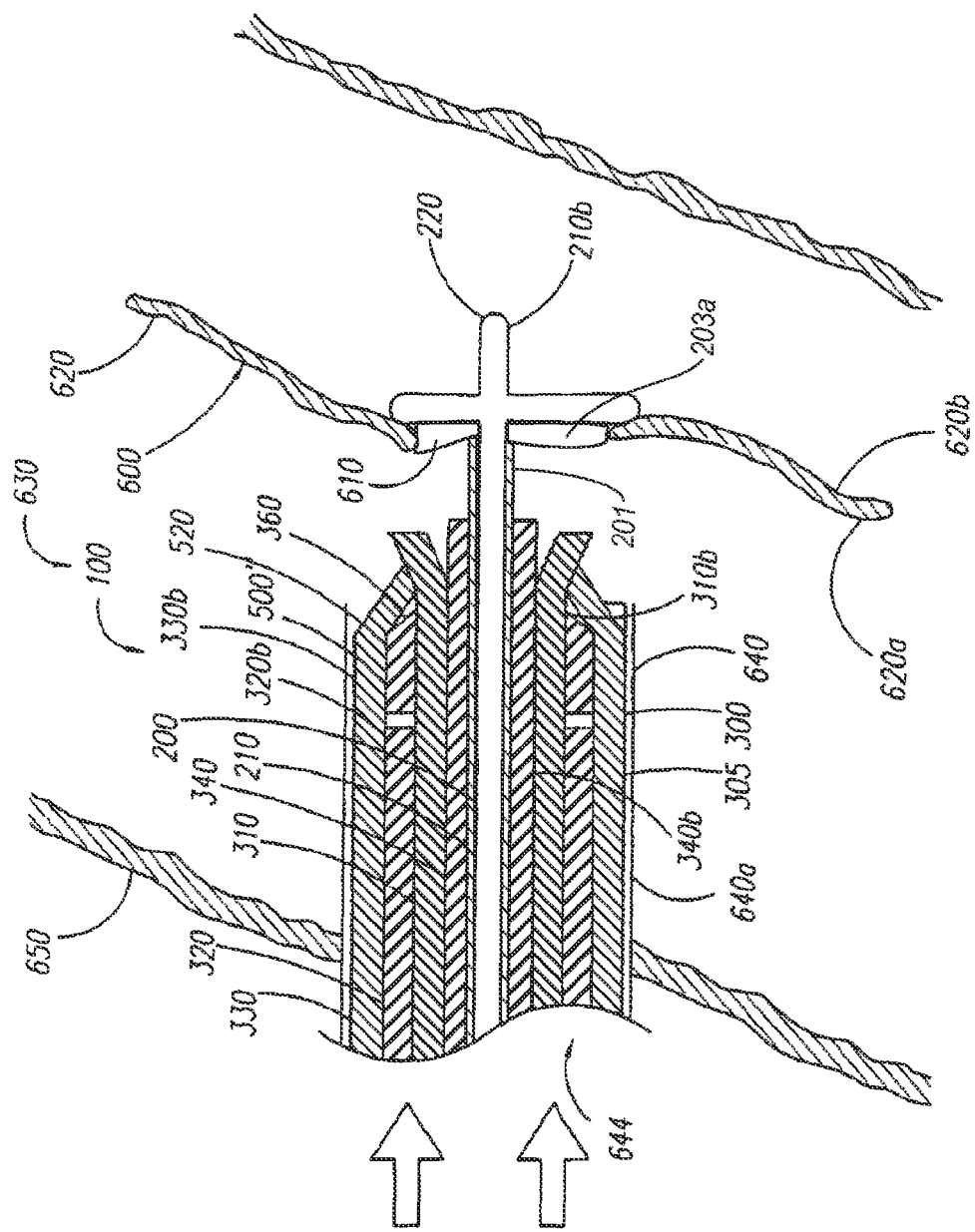

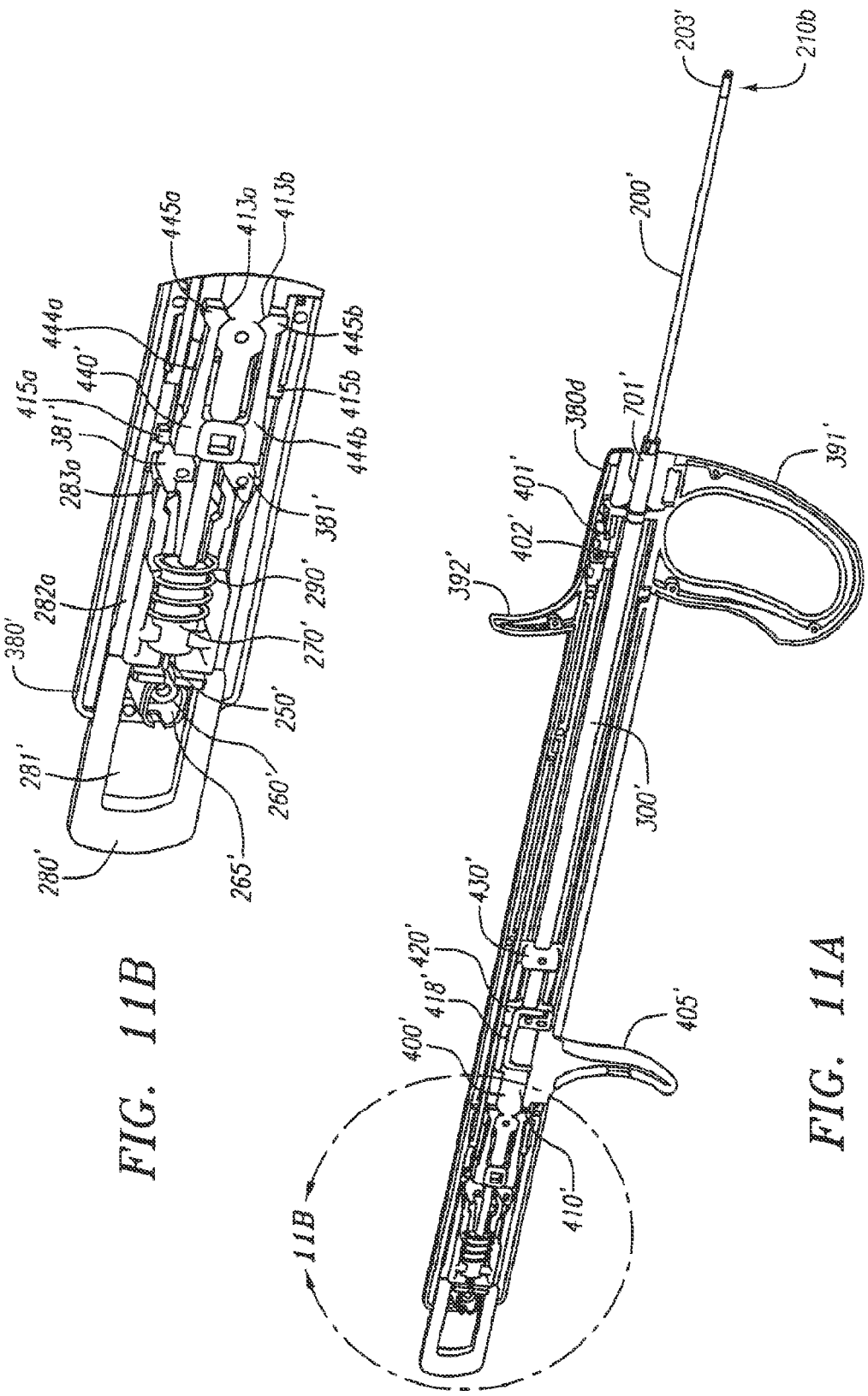

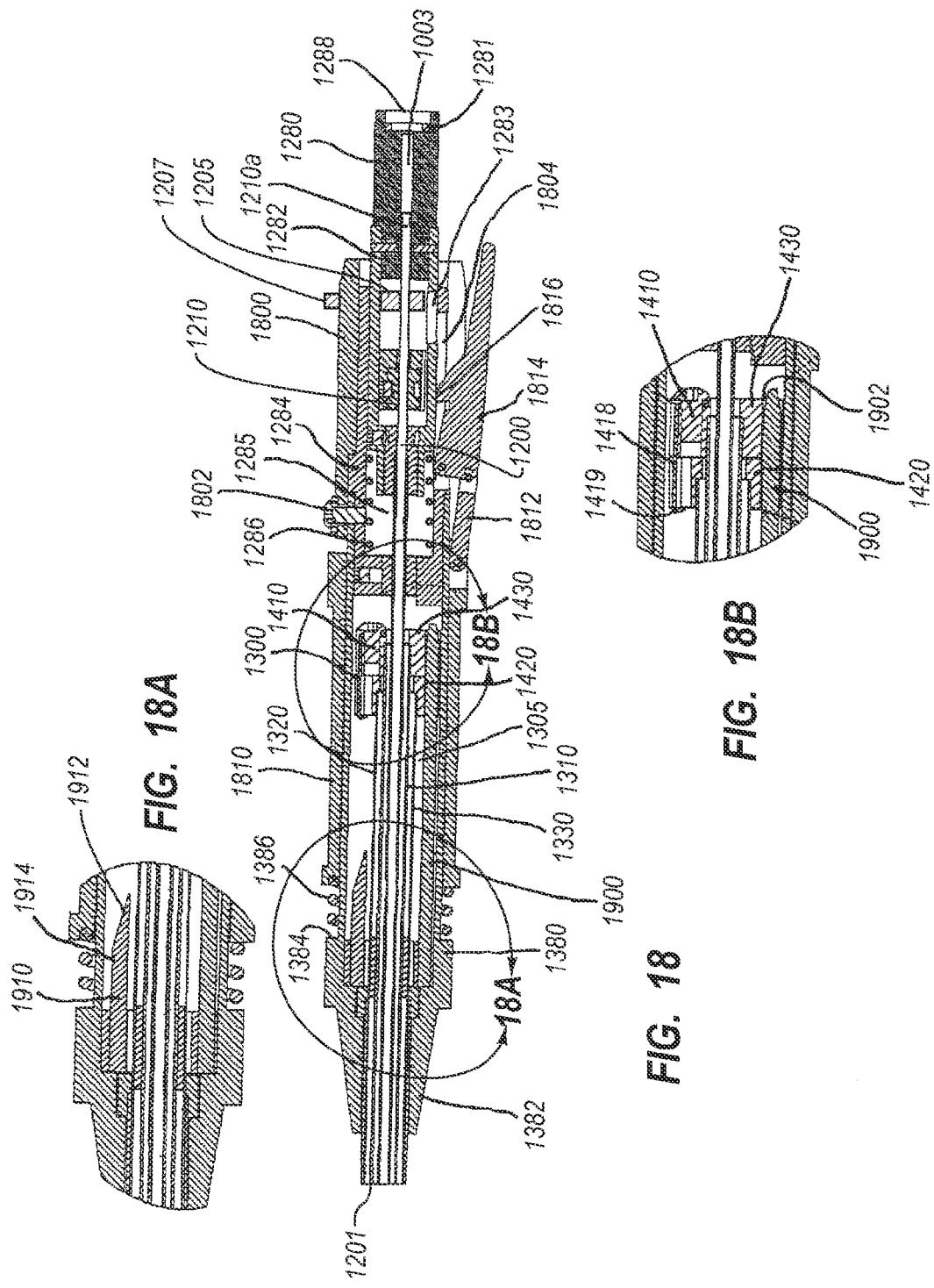

CLIP APPLIER HAVING IMPROVED HEMOSTASIS AND METHODS OF USE

BACKGROUND OF THE INVENTION

1. The Field of the Invention

The present invention relates generally to an apparatus and method for closing and/or sealing openings through tissue, and methods for providing improved hemostasis while delivering a closure element for closing a puncture in a blood vessel or other body lumen formed during a diagnostic or therapeutic procedure. More Particularly, the present invention relates generally to an apparatus and method for maintaining hemostasis during a medical procedure for closing and/or sealing openings through tissues and/or blood vessels.

2. The Related Technology

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally external pressure would be applied to the puncture site until clotting and wound sealing occur, however, the patient must remain bedridden for a substantial period of time after clotting to ensure closure of the wound. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Recently, it has been found that previous devices and methods for closing and/or sealing openings through tissue and/or blood vessels do not maintain hemostasis during the medical procedure. As such, blood can ooze or flow through the opening and complicate the medical procedure. Therefore, it would be advantageous to maintain hemostasis during a medical procedure for closing and/or sealing openings through tissues and/or blood vessels.

SUMMARY OF THE INVENTION

The present invention is directed toward a medical device and method for delivering a closure element through tissue and into an opening formed in, or adjacent to, a wall of a blood vessel or other body lumen of any size while maintaining or improving hemostasis. Generally, the present invention provides a medical device and method for use that maintains or improves hemostasis during a medical procedure for closing and/or sealing openings through tissues and/or blood vessels. It is further contemplated that the hemostasis system, implantable locator, hemostatic locator system, and medical devices described herein can be utilized for other medical procedures not described herein, and it shall be further understood that the methods described herein should be considered exemplary and not limiting.

In one embodiment, the present invention is a medical device for delivering a closure element to an opening formed in a body lumen or body tissue with improved hemostasis. Such a medical device can include a locator assembly, a hemostasis assembly, and a carrier assembly. The locator assembly can have a distal end region configured to extend through tissue into the opening and to selectively engage an internal surface of said body lumen adjacent to the opening so as to provide a desired position of the medical device relative to the body lumen. The distal end region can include a locator that is implantable to improve hemostasis. Also, the locator can be a hemostatic locator with similar hemostatic characteristics as the hemostasis assembly. The hemostasis assembly can be associated with the locator assembly, whether or not the locator assembly includes an implantable locator or hemostatic locator. The hemostasis assembly can have a selectively expandable member on a distal end configured to extend into the opening so as to be disposed therein when the locator assembly is in contact with said internal surface of said body lumen. The expandable member can be configured to expand laterally when disposed in the opening so as to substantially plug the opening to provide hemostasis. Also, the hemostasis assembly can include a member, such as the selectively expandable member or other aspect of the distal end that includes a hemostatic agent coated thereon. The carrier assembly can be slidably coupled with the locator assembly and hemostasis assembly. The carrier assembly can have a carrier member supporting the closure element and a cover member retaining the closure element within the carrier assembly. The carrier assembly can be positioned through the tissue adjacent to the opening and can be configured to distally deploy the closure element such that the closure element substantially uniformly expands to a cross-section that is greater than a natural cross-section of the closure element. The closure element can be configured to engage the body lumen when deployed such that the lumen is drawn substantially closed.

In one embodiment, the expandable member of the hemostasis assembly can be selectively controlled between an unexpanded state and an expanded state for engaging a wall of said opening. The expandable member of the hemostasis assembly in the unexpanded state can have a cross-section that is less than a cross-section of the opening. The expandable member of the hemostasis assembly in the expanded state can have a cross-section that is greater than or substantially equal to a cross-section of the opening. Also, a hemostatic agent can be included with the expandable member or the expandable member can be configured to release some hemostatic agent when expanding or fully expanded.

In one embodiment, the expandable member of the hemostasis assembly can include one or more expansion elements configured to expand substantially transversely with respect to a longitudinal axis of the hemostasis assembly. The one or more expansion elements can be disposed within a flexible portion of the expandable member of the hemostasis assembly so that the expansion elements flex the flexible portion from the unexpanded state to the expanded state in order to plug the opening and provide hemostasis.

In one embodiment, the expandable member includes a substantially flexible and/or deformable member with a substantially fixed end region fixedly coupled with the hemostasis assembly, an intermediate region, and a movable end region movable coupled with the hemostasis assembly such that the intermediate region is configured to expand transversely outwardly when the movable end region is axially moved toward the substantially fixed end region.

In one embodiment, the hemostasis assembly can include a control system coupled to a proximal end region of the hemostasis assembly. The control system can be configured to selectively control the expandable member of the hemostasis assembly between the expanded state and the unexpanded state. The control system can expand the expandable member and maintain the expandable member in the expanded state for a desired duration when the control system is engaged. The control system can change the expandable member from the expanded state to the unexpanded state when the control system is disengaged.

In one embodiment, the expandable member can include an expandable bladder. The bladder can be coupled to a fluid source that can inflate the bladder. For example, an inflation tube can be coupled with the bladder such that fluid, such as air, can be passed through the inflation tube to expand the bladder. A pump or other device that can cause the bladder to inflate may also be associated with the bladder an inflation tube.

In one embodiment, the expandable member expands by longitudinally compressing the expandable member so as to laterally expand the expandable member.

In one embodiment, the hemostasis assembly can include an actuator member that is actuated so as to expand the expandable member.

In one embodiment, the present invention includes a medical system for closing an opening formed in a body lumen or body tissue with improved hemostasis. Such a system can include an introducer sheath, locator assembly, hemostasis assembly, closure element, and carrier assembly for the closure element. The introducer sheath can be configured to be deployed into the body lumen or body tissue. The introducer sheath can include a proximal end, a distal end, and a lumen extending from the proximal end to the distal end. The locator assembly can be configured so as to be capable of being disposed in the lumen of the introducer sheath. The locator assembly can have a locator member at a distal end region of the locator assembly configured to extend through tissue into the opening and to selectively engage an internal surface of the body lumen adjacent to the opening so as to provide a desired position of the medical device relative to the opening and body lumen. Optionally, the locator member can be implantable and either biostable or biodegradable. In another option, the locator member can be hemostatic. The hemostasis assembly can be associated with the locator assembly, and can be capable of being disposed in the lumen of the introducer sheath with the locator assembly. The hemostasis assembly can have a selectively expandable member on a distal end configured to extend into the opening so as to be disposed therein when the locator assembly is in contact with the internal surface of the body lumen. The expandable member can be configured to expand laterally when disposed in the opening so as to contact the wall of the opening and substantially plug the opening to provide hemostasis. The carrier assembly can be slidably coupled with the locator assembly and hemostasis assembly, and can be dimensioned so as to be capable of being disposed in the introducer sheath with the locator assembly and the hemostasis assembly. The carrier assembly can have a carrier member supporting the closure element and a cover member retaining the closure element within the carrier assembly. The carrier assembly can be positioned through the tissue adjacent to the opening, and can be configured to distally deploy the closure element such that the closure element substantially uniformly expands to a cross-section that is greater than a natural cross-section of the closure element. The closure element can be configured to engage the tissue when deployed such that the tissue is drawn substantially closed.

In one embodiment, the expandable member of the hemostasis assembly can be selectively controlled between an unexpanded state and an expanded state for engaging a wall of the opening. Also, the locator member of the locator assembly can be selectively controlled between an unexpanded state and an expanded state for engaging the body lumen. The expandable member of the hemostasis assembly and the locator member of the locator assembly both can be in the unexpanded state and can have a cross-section that is less than a cross-section of the opening. The expandable member of the hemostasis assembly and the locator member of the locator assembly both in the expanded state can each have a cross-section that is greater than or substantially equal to a cross-section of the opening. Optionally, the expandable member and locator member can be configured to cooperate in providing hemostasis. this can allow for the locator member to apply pressure to the inside wall of a blood vessel while the expandable member of the homeostasis assembly can apply pressure to the outside of the vessel and/or against the vessel walls surrounding the opening in the vessel.

In one embodiment, the expandable member of the hemostasis assembly can include one or more hemostasis expansion elements configured to expand substantially transversely with respect to a longitudinal axis of the hemostasis assembly. The locator member of the locator assembly can also include one or more locator expansion elements configured to expand substantially transversely with respect to a longitudinal axis of the locator assembly.

In one embodiment, the hemostasis expansion elements are disposed within a flexible portion of the expandable member of the hemostasis assembly so that the one or more hemostasis expansion elements flex the flexible portion from the unexpanded state to the expanded state in order to plug the opening and provide hemostasis. The locator expansion elements can be substantially equally distributed about an outer periphery of the locator member of the locator assembly.

In one embodiment, each of the locator expansion elements can include a substantially flexible member with a substantially fixed end region fixedly coupled with said distal end region of the locator assembly, an intermediate region, and a movable end region movable coupled with the distal end region of the locator assembly such that the intermediate regions are configured to expand transversely outwardly when the movable end regions are axially moved toward said substantially fixed end regions.

In one embodiment, the expandable member of the hemostasis assembly can include a substantially flexible member with a substantially fixed end region fixedly coupled with the hemostasis assembly, an intermediate region, and a movable end region movable coupled with the hemostasis assembly such that the intermediate region is configured to expand transversely outwardly when the movable end region is axially moved toward the substantially fixed end region.

In one embodiment, the hemostasis assembly can include a hemostasis control system coupled to a proximal end region of the hemostasis assembly. The hemostasis control system can be configured to selectively control the expandable member of the hemostasis assembly between the expanded state and the unexpanded state.

In one embodiment, the locator assembly can include a locator control system coupled to a proximal end region of the locator assembly. The locator control system can be configured to selectively control the locator member of the locator assembly between the expanded state and the unexpanded state. The locator control can also be configured to release the locator upon application of the closure element so that the locator is retained against the inner wall of the vessel in order to facilitate hemostasis. The hemostasis control system and locator control system can be integrated. Also, the hemostasis control system and locator control system can be included in the same control system.

Generally, an embodiment of a closure element in accordance with the present can include a clip for closing an opening formed in a wall of a body lumen or body tissue. Such a clip can include a shape-memory clip having a relaxed configuration with a substantially planar-annular body defining a lumen with a plurality of tines directed inwardly from the body. Additionally, the clip can be oriented and held by a clip applier in a retaining configuration having a substantially asymmetrically-elongated tubular shape with a substantially trapezoidal longitudinal cross-sectional profile and a proximal portion having the plurality of tines being longitudinally and distally directed with a first tine of the plurality being more distally oriented compared to a substantially opposite second tine being more proximal. Also, the clip can be capable of retracting to a deploying configuration having a substantially symmetrical tubular shape with a substantially rectangular longitudinal cross-sectional profile with the first tine being substantially even with the second tine when the clip is being delivered from the clip applier to close the opening.

Additionally, the clip in the retaining configuration can have a lumen that has a smaller orthogonal cross-sectional profile (e.g., orthogonal to longitudinal direction) compared to the lumen in the deploying configuration. Alternatively, the clip in the retaining configuration can have a lumen that has a more oval orthogonal cross-sectional profile compared to the lumen in the deploying configuration having a more circular orthogonal cross-sectional profile. Also, the clip can automatically retract from the retaining configuration to the deploying configuration when being released from the clip applier. Further, the clip can automatically convert to the relaxed configuration from the deploying configuration after being released from the clip applier. Such conversion to the relaxed configuration can allow for the tines of the clip to grab the locator during the relaxation process, and retain the locator against the blood vessel wall to facilitate hemostasis.

In another embodiment, the present invention can include a clip applier apparatus for delivering a clip to an opening formed in a wall of a body lumen or body tissue. Such a clip applier can include a shape-memory clip as described herein. Additionally, the clip applier can include a carrier tube having an outer surface configured for slidably retaining the clip in a retaining configuration and slidably delivering the clip in a deploying configuration, wherein the retaining configuration and deploying configuration are described herein.

In one embodiment, the clip applier can include a pusher tube that can push the clip from the retaining configuration to the deploying configuration. Also, the pusher tube can be configured to distally push the clip in the retaining configuration over the carrier tube toward a distal end of the carrier tube. Further, the pusher tube can be configured to distally push the clip over a distal end of the carrier tube so that the clip retracts from the retaining configuration to the deploying configuration.

Additionally, the carrier tube can be configured so that the outer surface corresponds in shape and size with the lumen of the clip in the retaining configuration. Accordingly, the outer surface of the carrier tube can be generally oval in shape. Also, the outer surface can have a smaller orthogonal cross-sectional profile compared to the size of the lumen of the clip in the deploying configuration.

In yet another embodiment, the clip applier can include a clip expander that is capable of expanding the clip during deployment. As such, the clip expander can be a selectively expandable shape-memory clip expander. Also, the clip expander can be disposed at a distal portion of the carrier tube.

In still another embodiment, the clip applier can include a cover tube that contains any of the carrier tube, pusher tube, clip, and/or clip expander. As such, the cover tube can define a lumen that retains the clip in the retaining configuration. Also, the lumen of the cover tube can retain the clip expander in a contracted orientation so that the clip expander can be capable of expanding when moved distally past a distal end of the cover tube.

Another embodiment of the present invention can include a method for closing an opening formed in a wall of a body lumen or body tissue. Such a method can include positioning a carrier tube adjacent to the opening, wherein the carrier tube has a distal portion with an outer surface retaining a shape-memory clip in a retaining configuration. The carrier tube, clip, and retaining configuration can be as described herein. Additionally, the method can include pushing the clip over a distal end of the carrier tube so that the clip retracts to a deploying configuration, wherein the deploying configuration is described herein. Further, the method can include ejecting the clip from the carrier tube so that at least a portion of the plurality of tines disposed on the proximal end of the clip engage a portion of the wall of the body lumen or the body tissue whereby the opening is drawn substantially closed.

Additionally, the method can include pushing the clip toward the distal end of the carrier tube with a pusher tube being configured to distally push the clip in the retaining configuration. Also, the method can include flattening the clip, after being deployed from the carrier tube, to a relaxed configuration with a substantially planar-annular body defining a lumen with a plurality of tines directed inwardly from the body of the clip, wherein at least a portion of the tines have inwardly drawn a portion of the wall of the body lumen or the body tissue so as to substantially close the opening. Further, the method can include expanding the clip from the retaining configuration having a lumen with a smaller orthogonal cross-sectional profile to the deploying configuration so that the lumen has a larger orthogonal cross-sectional profile. Optionally, the clip can be expanded by a selectively expandable shape-memory clip expander. Furthermore, the method can include expanding the clip from the retaining configuration having a lumen with a more oval orthogonal cross-sectional profile to the deploying configuration so that the lumen has a more circular orthogonal cross-sectional profile.

In one embodiment, a method of closing an opening in a body lumen of a subject can include use of a medical device having a locator assembly and hemostasis assembly as described herein. Such a method can include; locating the body lumen with the locator; expanding the expandable hemostasis member so as to provide hemostasis to the opening; and deploying the closure element into the body lumen so as to close the body lumen. The method can also include expanding the locator from an unexpanded state to an expanded state and pulling the locator against the internal surface of the body lumen. The locator can be configured to automatically expand when moved out from tube of the locator assembly.

In one embodiment, the locator is configured to be implanted. As such, deployment of the closure element traps the implantable against the implantable adjacent to the internal surface of the body lumen. Optionally, the locator assembly includes a suture coupled to the implantable locator, and the suture is cut after the opening of the body lumen is closed. The suture can be biodegradable and any portion of the suture remaining in the subject degrades. The locator can be biostable or biodegradable.

In one embodiment, the locator is configured to be withdrawn from the body lumen as the closure element is deployed to close the opening. The locator assembly can include at least a first wire and a second wire that are coupled to the locator such that pulling on both the first wire and second wire draws the locator against the internal surface of the body lumen, and puling on one of the first wire or second wire unwinds the locator and withdraws the locator from the body lumen.

In one embodiment, a hemostasis assembly can have a hemostasis tube, and an expandable hemostasis member located at a distal end of the hemostasis tube, said expandable hemostasis member being configured to selectively expand at an opening in a body lumen so as to cover or plug the opening and provide hemostasis.

In one embodiment, an implantable body lumen locator can include: a biocompatible locator configured to be in an unexpanded state while being inserted through an opening in a body lumen and to be in an expanded state that is larger in diameter than the opening; and a locator assembly configured to deliver the biocompatible locator into the body lumen and selectively expand the locator assembly, and configured to release the biocompatible locator therefrom for implantation. The locator assembly can include one or more sutures coupled to the locator, the one or more sutures being configured to be cut.

In one embodiment, an implantable body lumen locator can include: a biocompatible locator configured to be in an unexpanded state while being inserted through an opening in a body lumen and to be in an expanded state that is larger in diameter than the opening; and a locator assembly configured to deliver the biocompatible locator into the body lumen and selectively expand the locator assembly, and configured to retract the biocompatible locator from the body lumen, said locator assembly having at least a first locator wire coupled with a first end of the locator and a second locator wire coupled to a second end of the locator such that pulling on both the first locator wire and second locator wire draws the locator against the internal surface of the body lumen, and puling on one of the first wire or second wire unwinds the locator and withdraws the locator from the body lumen.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which:

FIG. 1 provides a general illustration of an apparatus for closing openings formed in blood vessel walls in accordance with the present invention.

FIG. 2A illustrates one embodiment of a locator assembly for the apparatus of FIG. 1.

FIG. 4A illustrates a cross-sectional side view of one embodiment of a triggering system for the carrier assembly of FIG. 3A.

FIG. 4B illustrates a first detailed cross-sectional side view of the triggering system of FIG. 4A.

FIG. 5A illustrates the carrier control system of FIGS. 4A-4D as the carrier assembly of FIG. 3A moves distally from an initial predetermined position.

FIG. 5B illustrates the carrier control system of FIGS. 4A-4D as the carrier assembly of FIG. 3A reaches a first predetermined position.

FIG. 8H illustrates the relative positions of the tube set of FIG. 8G upon reaching a second predetermined position.

FIG. 11A illustrates the assembled carrier assembly and triggering assembly of the alternative embodiment of the apparatus shown in FIG. 10A.

FIG. 11B illustrates a close-up view of the proximal end of the apparatus shown in FIG. 11A.

FIG. 18 illustrates a cross-sectional view of the device shown in FIG. 16.

FIG. 18A illustrates a close-up cross-sectional view of a portion of the device shown in FIG. 18.

FIG. 18B illustrates a close-up cross-sectional view of a portion of the device shown in FIG. 18.

Figure 2B:
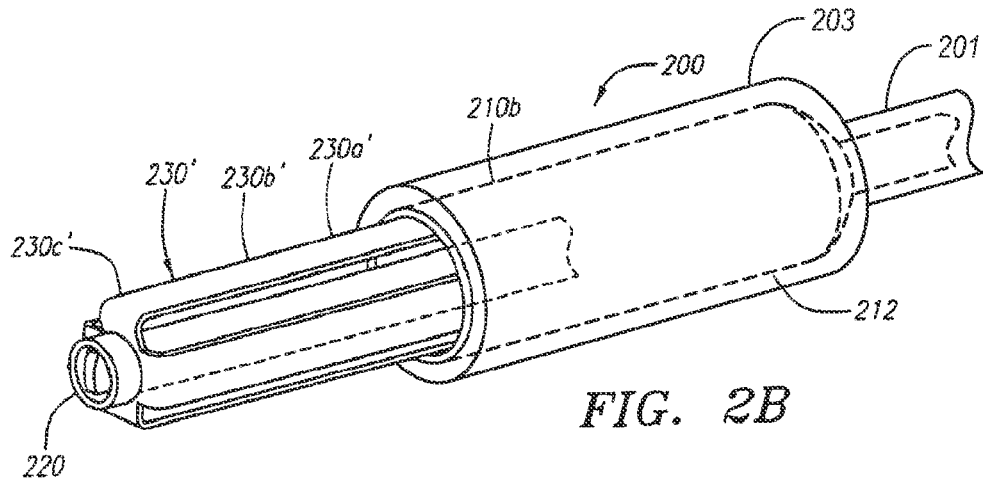
FIG. 2B illustrates one embodiment of a distal end region of the locator assembly of FIG. 2A when the distal end region is in an unexpanded state.

It should be noted that the figures are not drawn to scale and that elements of similar structures or functions are generally represented by like reference numerals for illustrative purposes throughout the figures. It also should be noted that the figures are only intended to facilitate the description of the illustrated preferred embodiments of the present invention. The figures do not describe every aspect of the present invention and do not limit the scope of the invention.

DETAILED DESCRIPTION

Generally, the present invention is directed toward a medical device and method for maintaining hemostasis while delivering a closure element through tissue and into an opening formed in, or adjacent to, a wall of a blood vessel or other body lumen of any size. As such, the present invention provides a medical device and method for use that maintains or improves hemostasis during a medical procedure for closing and/or sealing openings through tissues and/or blood vessels. The present invention also includes an implantable locator that can be used to facilitate hemostasis as well as a locator that includes hemostatic components.

The apparatus can be configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening. The apparatus can include a locator element that locates the blood vessel to improve placement of the closure element, where the locator can optionally be implantable or hemostatic.

Additionally, the apparatus is configured to maintain hemostasis throughout the medical procedure so as to inhibit blood from oozing or flowing from the blood vessel. Further, the apparatus includes an expandable hemostatic element that expands so as to contact the blood vessel at the opening and/or around the opening on the external surface of the blood vessel so as to maintain or improve hemostasis after the apparatus is retracted and the locator element is adjacent to the opening. This can include the expandable hemostatic element being selectively expandable such that the expandable element is retracted while the apparatus is being placed adjacent to the opening and the locator element is locating the blood vessel wall. The expandable hemostatic element is selectively expanded during or after the procedure for locating the blood vessel wall so as to maintain hemostasis, and then retracted during placement of the closure element so that the closure element can engage tissue around the expandable element. After placement of the closure element, the apparatus can be withdrawn.

When properly positioned, the apparatus can be activated to distally deploy the closure element. During deployment, the apparatus can be configured to substantially uniformly expand the closure element beyond a natural cross-section of the closure element such that the closure element, when deployed, is configured to engage significant amount of the blood vessel wall and/or tissue. Engaging the blood vessel wall and/or tissue, the closure element can be further configured to return to the natural cross-section. Thereby, the engaged blood vessel wall and/or tissue are drawn substantially closed and/or sealed, such that, for example, hemostasis within the opening is enhanced. Also, the implantable locator can be held against the inner wall of the blood vessel by the closure element, and thereby implanted, to enhance hemostasis.

During the deployment of the closure element, the expandable hemostatic element expands at or around the opening in the blood vessel so as to provide improved hemostasis. The expandable hemostatic element can be expandable by various means which are described in more detail herein. In one example, the expandable hemostatic element can be selectively expanded as shown herein with relation to the expandable locator, and the expandable hemostatic element can include the features of the expandable locator.

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved by employing a clip applier and associated methods of use in accordance with the present invention.

I. First Clip Applier

Figure 6A:
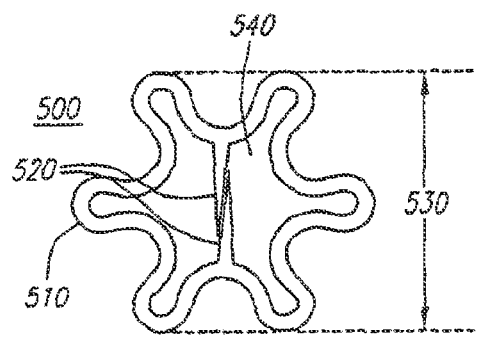
FIG. 6A illustrates a top view of one embodiment of a closure element in a natural, planar configuration and with a natural cross-section for use with the apparatus of FIG. 1.
Figure 6B:
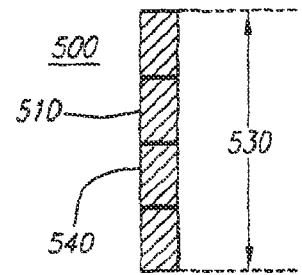
FIG. 6B illustrates a side view of the closure element of FIG. 6A.
Figure 6C:
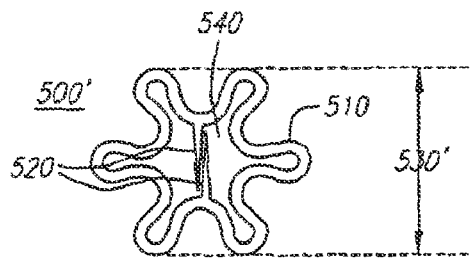
FIG. 6C illustrates a top view of the closure element of FIGS. 6A-6B after a natural cross-section of the closure element has been reduced.
Figure 6D:
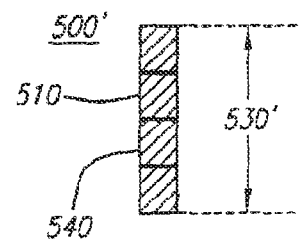
FIG. 6D illustrates a side view of the reduced closure element of FIG. 6C.
Figure 6E:
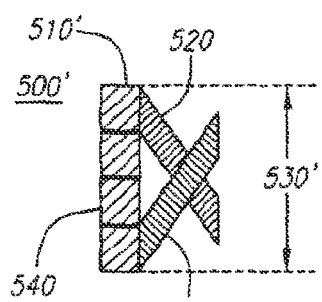
FIG. 6E illustrates a side view of the reduced closure element of FIGS. 6C-6D as the reduced closure element transitions from the natural, planar configuration to a tubular configuration.
Figure 6F:
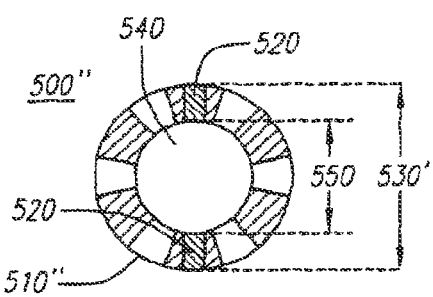
FIG. 6F illustrates a bottom view of the closure element of FIGS. 6C-6D upon completing the transition from the natural, planar configuration to a substantially tubular configuration.

FIG. 1 illustrates a clip applier apparatus 100 in accordance with the present invention. As will be discussed in more detail below, the apparatus 100 can deliver a closure element 500 (shown in FIGS. 6A-6B) through tissue 630 (shown in FIG. 8A) and into an opening 610 (shown in FIG. 8A) formed in and/or adjacent to a wall 620 (shown in FIG. 8A) of a blood vessel 600 (shown in FIG. 8A) or other body lumen. The closure element (also referred to herein as a "clip") 500 can have a generally annular-shape body 510 (shown in FIG. 6A-6B) defining a channel 540 and one or more barbs and/or tines 520 (shown in FIGS. 6A-6B) for receiving and engaging the blood vessel wall 620 and/or the tissue 630 around the opening 610. Although the closure element 500 has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 6A-6B. The natural cross-section 530 of the closure element 500 can be reduced to form a reduced closure element 500' that has a natural, planar configuration with opposing tines 520 and a reduced cross-section 530' as shown in FIGS. 6C-6D. By rotating the opposing tines 520 axially as shown in FIG. 6E, the reduced closure element 500' can be further deformed to form a substantially tubular closure element 500" (shown in FIG. 6F) having the reduced cross-section 530' as well as being in a substantially tubular configuration with the tines 520 in an axial configuration.

Being configured to draw the blood vessel wall 620 and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof. Additionally, it is contemplated that the closure element may be fully, partially, or selectively coated with a beneficial agent or a hemostatic agent, or be constructed as a composite, wherein one component of the composite would be a beneficial agent or hemostatic agent. As desired, the closure element 500 may further include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. Nos. 6,197,042, and 6,623,510, and in co-pending application Ser. Nos. 09/546,998, 09/610,238, and 10/081,726. The disclosures of these references and any others cited therein are expressly incorporated herein by reference.

The apparatus 100 can be configured to receive and retain the closure element 500 such that the closure element 500 is disposed substantially within the apparatus 100. Thereby, if the apparatus 100 is introduced via an introducer sheath 640 (shown in FIG. 8A), for example, the closure element 500 can be disposed within, and delivered by way of, a lumen 644 (shown in FIG. 8A) of the introducer sheath 640. The apparatus 100 also can be configured to engage the blood vessel wall 620 adjacent to the opening 610, which engagement can be via a locator element 220 and a hemostasis member 203 (shown in FIG. 8E). The locator element 220 is configured and used for locating the blood vessel wall, and the hemostasis member 203 is configured to selectively expand so as to fill the opening 610 (e.g., hole) in the body lumen to be closed and sealed by the closure element 500. Alternatively, the hemostasis member 203 can be configured to expand so as to contact the outer wall of the blood vessel opposite of the locator element 220 so that the locator element 220 and hemostasis member 203 can cooperate to facilitate hemostasis. Being disposed substantially within the apparatus 100, the closure element 500 can deeply penetrate, without inadvertently contacting, tissue 630 adjacent to the opening 610 such that the apparatus 100 can position the closure element 500 substantially adjacent to an outer surface 620a (shown in FIG. 8A) of the blood vessel wall 620 adjacent to the opening 610. The hemostasis member 203 maintains or improves hemostasis during the placement of the apparatus 100 with respect to the blood vessel wall 620 and opening 610 by expanding to contact the blood vessel wall 620 at or around the opening 610.

When properly positioned, the apparatus 100 can be activated to deploy the closure element 500. Although in one configuration, the closure element 500 can be configured to substantially uniformly expand beyond the natural cross-section 530 of the closure element 500 during deployment, the apparatus 100, as desired, can deploy the closure element 500 without expanding the closure element 500. The closure element 500, when deployed, can be configured to engage a significant amount of the blood vessel wall 620 and/or tissue 630 adjacent to the opening 610. Engaging the blood vessel wall 620 and/or tissue 630, the closure element 500 is further configured to return to the natural cross-section 530. Thus, the engaged blood vessel wall 620 and/or tissue 630 can be drawn substantially closed and/or sealed, such that, for example, hemostasis within the opening 610 is enhanced.

The apparatus 100 can be provided as one or more integrated components and/or discrete components. As shown in FIG. 1, for example, the apparatus 100 can include a locator (or obturator) and hemostasis assembly 200 (e.g., locator assembly 200) disposed in a carrier assembly 300. For purposes of illustration, the locator and hemostasis assembly 200 and the carrier assembly 300 are shown in FIG. 1 as substantially separate assemblies. As desired, however, the locator and hemostasis assembly 200 and the carrier assembly 300 each can be provided, in whole or in part, as one or more integrated assemblies. It should be noted that the locator and hemostasis assembly 200 can be referred to as the locator assembly 200 or assembly 200. In the instance it is separate, it should be recognized by the skilled artisan that the hemostasis portion of the assembly 200 can function substantially identically with the locator assembly 200 as described herein. Thus, the locator portion and hemostasis portion of the assembly 200 can be integrated as a single assembly or separated into two distinct assemblies.

A. Locator and Hemostasis Assemblies

Being configured to extend into the opening 610, the assembly 200 includes a selectively expandable locator tip 220 that can selectively contact the inner surface 620b of the blood vessel wall 620 adjacent the opening 610. Also, the assembly 200 includes a selectively expandable hemostasis member 203 that can contact the external surface 620b of the blood vessel wall 620 of the opening 610 so as to provide improved hemostasis. The selectively expandable locator tip 220 of the assembly 200 can be configured to draw the blood vessel wall 620 taut and maintain the proper position of the apparatus 100 in relation to the opening 610 as the blood vessel 600 pulsates, and the selectively expandable hemostasis member 203 can expand so as to plug the opening 610 while the locator tip 220 is being properly positioned. The locator portion of the assembly 200 can be provided in the manner disclosed in co-pending application Ser. Nos. 09/732,835 and 10/081,723, the disclosures of which are expressly incorporated herein by reference.

The locator portion of the assembly 200 can include a flexible or semi-rigid tubular body 210 having a central axis 216. As illustrated in FIG. 2A, the tubular body 210 has a proximal end region 210a and a distal end region 210b and includes a predetermined length 218a and a predetermined outer cross-section 218b, both of which can be of any suitable dimension. The distal end region 210b of the locator assembly 200 can include a substantially rounded, soft, and/or flexible distal end or tip 220 to facilitate atraumatic advancement and/or refraction of the distal end region 210b into the blood vessel 600. As desired, a pigtail (not shown) may be provided on the distal end 220 to further aid atraumatic advancement of the distal end region 210b.

The hemostasis portion of the assembly 200 can include a flexible or semi-rigid tubular body 201 (i.e., hemostasis tube 201) that correlates with the central axis 216. The hemostasis tube 201 includes an expandable hemostasis member 203 at the distal end that can selectively expand when disposed in the opening 610 so as to substantially fill and/or plug the opening 610 in order to provide improved hemostasis during placement of the locator tip 220. The expandable hemostasis member 203 can have a donut like shape around the hemostasis tube 201, or it can have any of various planar, spherical, or other shape that can facilitate hemostasis when expanded adjacent with the opening 610 of the blood vessel 620.

The distal end region 210b of the locator portion of the assembly 200 includes the hemostasis member 203 and locator tip 220, each of which can be selectably controllable between an unexpanded state and an expanded state. In the unexpanded state, the hemostasis member 203 and/or locator tip 220 has an unexpanded size; whereas, the hemostasis member 203 and/or locator tip 220 in the expanded state has an expanded size, which is greater than the unexpanded size of the distal end region 210b in the unexpanded state. The hemostasis member 203 and/or locator tip 220 can be configured to expand from the unexpanded size to the expanded size and/or to contract from the expanded size to the unexpanded size, and the expansion and contraction of the hemostasis member 203 and/or locator tip 220 can be substantially uniform about a longitudinal axis of the assembly 200. For example, one or more expansion elements 230 of the locator tip 220 can be provided on the distal end region 210b and can be configured to expand substantially transversely with respect to a longitudinal axis of the assembly 200 while being disposed within blood vessel so as to be capable of contacting the inner surface 620b of the blood vessel wall 620. The hemostasis member 203 can also include one or more expansion elements (not shown) that can be expanded while disposed at or around the opening 610 so as to cover and/or fill at least the cross-sectional area of the opening 610. In one configuration, being substantially equally distributed about an outer periphery 212 of the distal end region 210b, the expansion elements 230 and/or hemostasis member 203 may include radiopaque markers (not shown) or may be wholly or partially formed from a radiopaque material to facilitate observation of the expansion elements 230 and/or the hemostasis member 203 using fluoroscopy or other imaging systems.

Figure 2C:
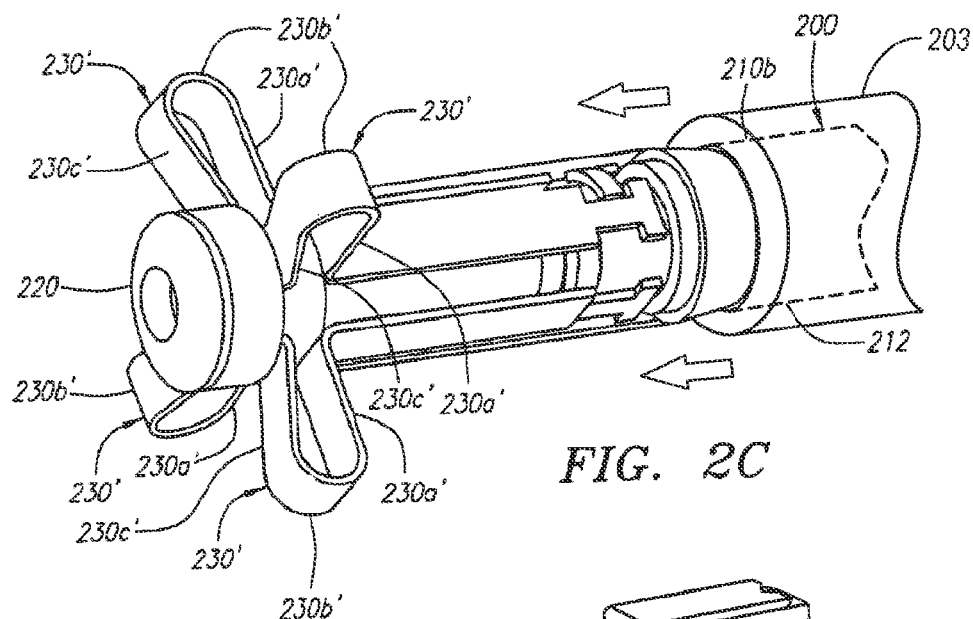
FIG. 2C illustrates the distal end region of the locator assembly of FIG. 2B when the distal end region is in an expanded state.

At least one of the expansion elements 230 of the locator tip 220 can include a substantially flexible member 230' with a substantially fixed end region 230a', an intermediate region 230b', and a movable end region 230c' as shown in FIGS. 2B-2C. For each substantially flexible member 230', the fixed end region 230a' can be fixedly coupled with the distal end region 210b; whereas, the movable end region 230c' can be movably coupled with the distal end region 210b and configured to be axially movable relative to the fixed end region 230a'. When each movable end region 230c' can be axially moved toward the relevant fixed end region 230a', the intermediate regions 230b' buckle and/or expand transversely outwardly, thereby transitioning the distal end region 210b of the locator assembly 200 from the unexpanded state to the expanded state. In contrast, the distal end region 210b transitions from the expanded state to the unexpanded state as each of the movable end regions 230c' are axially moved away from the relevant fixed end region 230a'. Although the expansion elements 230 are shown as the flexible members 230' in FIGS. 2B-2C for purposes of illustration, it is understood that the expansion elements 230 can include any type of expansion elements and are not limited to the illustrated embodiments. It is further contemplated that the expansion elements 230 may further include geometric features that allow/enhance the ability of the expansion elements to bend or fold from a retracted position to an expanded position. The expansion elements may be constructed of a material such as steel, spring steel, plastics or composites. In one configuration, the expansion elements are constructed of nitinol. The expandable hemostasis member 203 can be configured similarly.

Additionally, the hemostasis member 203 can include substantially flexible materials. The flexible materials can provide for the hemostasis member 203 to be selectively expanded to provide hemostasis and selectively retracted after the opening 610 is closed with the closure element 500. In one embodiment, the mechanism for expanding the substantially flexible member 230' can also expand the hemostasis member 203. The hemostasis member 203 may be constructed of a material such as steel, spring steel, shape memory materials plastics, polymers, rubbers, foams, memory foams, bladders, balloon-like materials, composites, and appropriate combinations thereof. In one configuration, the hemostasis member 203 can be constructed of a rubber bladder being reinforced with nitinol. In another configuration, the hemostasis member 203 is a portion of a nylon sheath that can be buckled and shortened in order to be selectively expanded.

Figure 2D:
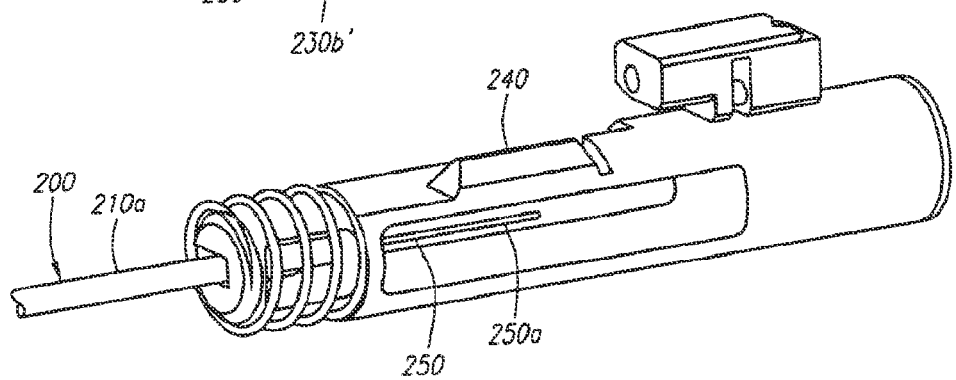
FIG. 2D illustrates one embodiment of a proximal end region of the locator assembly of FIG. 2A.

Referring now to FIG. 2D, the assembly 200 may further include a locator control system 240 associated with the assembly 200. As shown in FIG. 2D, the locator control system 240 can be associated with the proximal end region 210a of the locator assembly 200 and can be configured to selectively control the distal end region 210b of the locator assembly 200 between the unexpanded and expanded states. The locator control system 240 can selectively control the distal end region 210b between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210a and the distal end region 210b. The control member 250 has a proximal end region 250a that is coupled with the locator control system 240, optionally via a control block 260 (shown in FIG. 4D), and a distal end region (not shown) that is coupled with the distal end region 210b of the assembly 200, the expansion elements 230, and/or the movable end regions 230c' of the substantially flexible members 230'. The locator control system 240 can selectively transition the distal end region 210b, the expansion elements 230, and/or the substantially flexible members 230' between the unexpanded and expanded states by moving the control member 250 axially relative to the tubular body 210.

The locator control system 240 further can include a locator release system 490 (FIG. 4D) for maintaining the unexpanded state and/or the expanded state of the distal end region 210b, the expansion elements 230, and/or the substantially flexible members 230'. To aid the locator release system 490 to maintain the expanded state of the distal end region 210b, the locator release system 490 can include any type of locking system and can be engaged, for instance, by activating the switching system. For example, once the substantially flexible members 230' have entered the expanded state, the locator release system 490 can secure the control member 250 to prevent axial movement relative to the tubular body 210, thereby maintaining the substantially flexible members 230' in the expanded state.

In the manner described in more detail below, the locator control system 240 also can be configured to disengage the locator release system 490, such that the distal end region 210b, the expansion elements 230, and/or the substantially flexible members 230' can transition between the expanded and unexpanded states. The locator release system 490 can be disengaged, for example, by activating an emergency release system (not shown). As desired, the locator control system 240 may further include a biasing system (not shown), such as one or more springs or other resilient members, to bias the distal end region 210b, the expansion elements 230, and/or the substantially flexible members 230' to enter and/or maintain the unexpanded state when the locator release system 490 is disengaged. Also, the locator control system 240 can be configured to release the locator when configured to be implanted so that the clip or closure element can capture the implantable locator during the closure process.

Additionally, the hemostasis member 203 can be selectively expanded by the locator control system 250 or a similar control system (not shown). Any control system for selectively expanding and/or retracting the hemostasis member 203 can be configured similarly as the locator control system 250 as shown in the figures and described herein. This can include the control system utilizing the hemostasis tube 201 in order to provide the appropriate signal for selective expansion and/or refraction.

Returning to FIG. 1, the carrier assembly 300 can be coupled with, and slidable relative to, the locator assembly 200. The carrier assembly 300 is configured to receive and retain the closure element 500 (shown in FIGS. 6A-6B), which can be disposed substantially within the carrier assembly 300. When the locator assembly 200 engages the inner surface 620b (shown in FIG. 8A) of the blood vessel wall 620 (shown in FIG. 8A) and the hemostasis member 203 engages the opening 610 and/or outer surface 620a of the blood vessel wall 620 so as to function as a hemostatic plug or hemostatic cap, the carrier assembly 300 can be further configured to position the closure element 500 substantially adjacent to the opening 610 (shown in FIG. 8A) and to deploy the closure element 500. Upon being deployed, the closure element 500 can maintain the reduced cross-section 530' (shown in FIGS. 6C-6D) but can be temporarily and substantially uniformly expanded beyond the natural cross-section 530 (shown in FIGS. 6A-6B) of the closure element 500. In either case, the closure element 500, when deployed, can engage a significant amount of the blood vessel wall 620 and/or tissue 630 adjacent to the opening 610. Thereafter, the closure element 500 can be configured to return to the natural cross-section 530, optionally substantially uniformly, such that the blood vessel wall 620 and/or tissue 630 is drawn substantially closed and/or sealed. During the deployment of the closure element 500 into the blood vessel wall 620, the hemostasis member 203 and locator tip 220 are retracted and extracted from the opening 610. This is done in a manner that retains proper location and hemostasis for placement of the closure element 500.

B. Tube Set

Figure 3A:
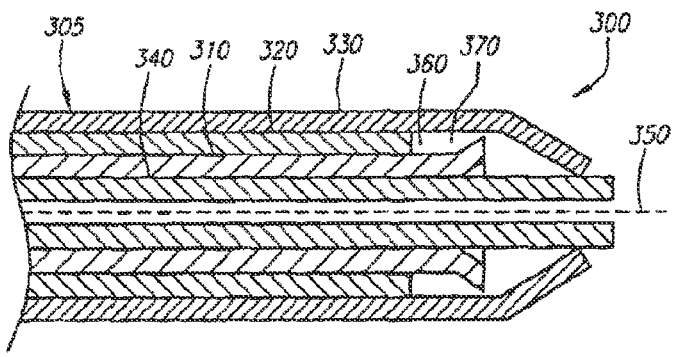
FIG. 3A illustrates one embodiment of a carrier assembly for the apparatus of FIG. 1.
Figure 6G:
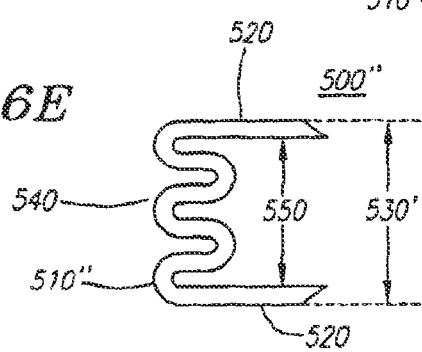
FIG. 6G illustrates a side view of the closure element of FIG. 6F.

Turning to FIGS. 3A-3D, the carrier assembly 300 can include a tube set 305, consisting of a carrier member 310, a pusher member 320, a support tube 340, and a cover member 330. The carrier member 310, the pusher member 320, the support tube 340, and the cover member 330 can be provided as a plurality of nested, telescoping members with a common longitudinal axis 350 as illustrated in FIG. 3A. The carrier member 310 can be configured to receive and support the closure element 500. While being disposed on the carrier member 310, the closure element 500 can be deformed from the natural, planar configuration to form the substantially tubular closure element 500" (shown in FIG. 6F-6G) as will be discussed in more detail below. Being disposed substantially about, and supported by, an outer periphery 312b of the carrier member 310, the substantially tubular closure element 500" can be substantially in axial alignment with the carrier member 310 with the tines 520 pointed substantially distally.

Figure 3B:
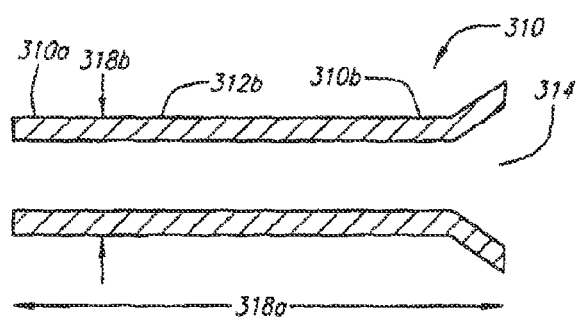
FIG. 3B illustrates one embodiment of a carrier member for the carrier assembly of FIG. 3A.

In one configuration, the carrier member 310 can be formed as a substantially rigid, semi-rigid, or flexible tubular member. The carrier member 310 can have a proximal end region 310a and a distal end region 310b and can include a predetermined length 318a and a predetermined cross-section 318b, both of which can be of any suitable dimension. The carrier member 310 also can define a lumen 314 that extends substantially between the proximal end region 310a and the distal end region 310b and that is configured to slidably receive at least a portion of the tubular body 210 of the locator assembly 200. Although the cross-section 318b of the carrier member 310 generally is substantially uniform, the distal end region 310b of the carrier member 310 can have a cross-section that increases distally, as illustrated in FIGS. 3A-3B, for substantially uniformly expanding the substantially tubular closure element 500" beyond the natural cross-section 530 of the closure element 500 when the substantially tubular closure element 500" is deployed. To deploy the closure element 500 without expanding the closure element 500, the distal end region 310b can be formed with a cross-section (not shown) that is substantially uniform. Although shown and described as having the cross-section that increases distally for expanding the substantially tubular closure element 500", it will be understood that the distal end region 310b of the carrier member 310 can be provided with the substantially-uniform cross-section and that the substantially tubular closure element 500" can be deployed without being expanded.

Being configured to distally deploy the substantially tubular closure element 500", the pusher member 320 has a proximal end region 320a and a distal end region 320b and is coupled with, and slidable relative to, the carrier member 310. The pusher member 320 includes a predetermined length 328a and a predetermined cross-section 328b, both of which can be of any suitable dimension and have an outer periphery 322b that can be configured to slidably receive the carrier member 310 such that the distal end region 320b of the pusher member 320 is offset proximally from the distal end region 310b of the carrier member 310. As desired, the predetermined length 328a of the pusher member 320 can be greater than or substantially equal to the predetermined length 318a of the carrier member 310. The predetermined length 328a of the pusher member 320, however, can be less than the predetermined length 318a of the carrier member 310 such that the carrier member 310 and the pusher member 320 at least partially define a space 360 distal to the distal end region 320b of the pusher member 320 and along the periphery 312b of the carrier member 310.

Figure 3C:
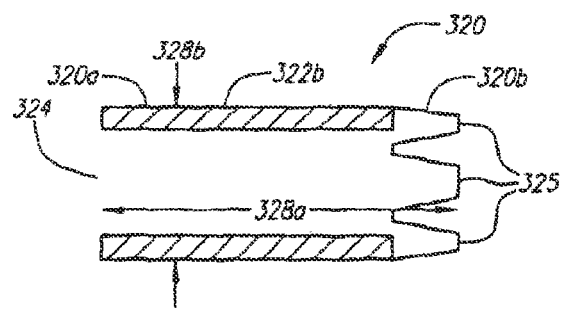
FIG. 3C illustrates one embodiment of a pusher member for the carrier assembly of FIG. 3A.

Being formed from a substantially rigid, semi-rigid, or flexible material, the pusher member 320 can be substantially tubular and can define a lumen 324 that extends substantially between the proximal end region 320a and the distal end region 320b and that is configured to slidably receive at least a portion of the carrier member 310. The cross-section 328b of the pusher member 320 can be substantially uniform, and the distal end region 320b of the pusher member 320 can include one or more longitudinal extensions 325, which extend distally from the pusher member 320 and along the periphery 312b of the carrier member 310 as shown in FIG. 3C. The longitudinal extensions 325 can be biased such that the longitudinal extensions 325 extend generally in parallel with common longitudinal axis 350. The longitudinal extensions 325 are sufficiently flexible to expand radially, and yet sufficiently rigid to inhibit buckling, as the distal end region 320b is directed distally along the carrier member 310 and engage the distally-increasing cross-section of the distal end region 310b of the carrier member 310 to deploy the substantially tubular closure element 500".

Figure 3D:
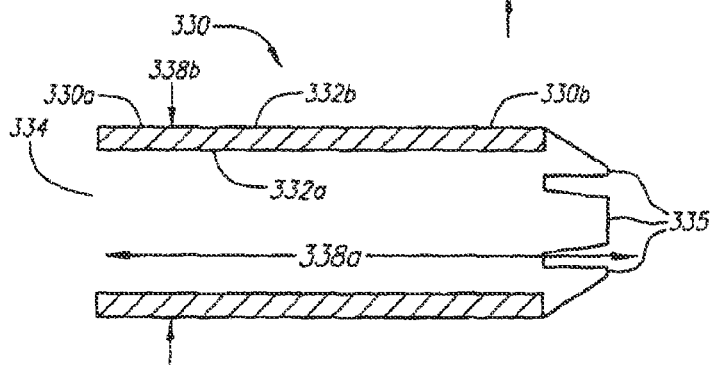
FIG. 3D illustrates one embodiment of a cover member for the carrier assembly of FIG. 3A.

A cover member 330 is configured to retain the substantially tubular closure element 500" substantially within the carrier assembly 300 prior to deployment as shown in FIG. 3D. Being coupled with, and slidable relative to, the pusher member 320, the cover member 330 has a proximal end region 330a and a distal end region 330b and includes a predetermined length 338a and a predetermined cross-section 338b, both of which can be of any suitable dimension. The cover member 330 can be formed as a substantially rigid, semi-rigid, or flexible tubular member. The cover member 330 can have an inner periphery 332a and an outer periphery 332b and can define a lumen 334. The lumen 334 can extend substantially between the proximal and distal end regions 330a, 330b of the cover member 330 and can be configured to slidably receive at least a portion of the pusher member 320. When the cover member 330 is properly positioned within the carrier assembly 300, the distal end region 330b can be configured to extend over the space 360, thereby defining an annular cavity 370 for receiving and retaining the substantially tubular closure element 500".

The cross-section 338b of the cover member 330 can be substantially uniform, and the distal end region 330b of the cover member 330 can include one or more longitudinal extensions 335, which extends distally from the cover member 330 and along an outer periphery 322b of the pusher member 320 as shown in FIG. 3D. Although the longitudinal extensions 335 can extend generally in parallel with common longitudinal axis 350, the longitudinal extensions 335 can be biased such that the plurality of longitudinal extensions 335 extend substantially radially inwardly as illustrated in FIGS. 3A and 3D. Thereby, the longitudinal extensions 335 can at least partially close the lumen 334 substantially adjacent to the distal end region 330b of the cover member 330. To permit the substantially tubular closure element 500" to be deployed from the annular cavity 370, the longitudinal extensions 335 can be sufficiently flexible to expand radially to permit the distal end region 310b of the carrier member 310 to move distally past the cover member 330 to open the annular cavity 370 such that the distal end region 330b no longer extends over the space 360.

If the carrier assembly 300 is assembled as the plurality of nested, telescoping members as shown in FIG. 3A, the carrier member 310 can be at least partially disposed within, and slidable relative to, the lumen 324 of the pusher member 320 as shown in FIG. 3C. The pusher member 320, in turn, can be at least partially disposed within, and slidable relative to, the lumen 334 of the cover member 330. To couple the carrier assembly 300 with the locator assembly 200, the tubular body 210 of the locator assembly 200 can be at least partially disposed within, and slidable relative to, the lumen 314 of the carrier member 310. The longitudinal axis of the locator assembly 200 can be substantially in axial alignment with the common longitudinal axis 350 of the carrier member 310, the pusher member 320, the cover member 330, and the support tube 340.

Figure 3E:
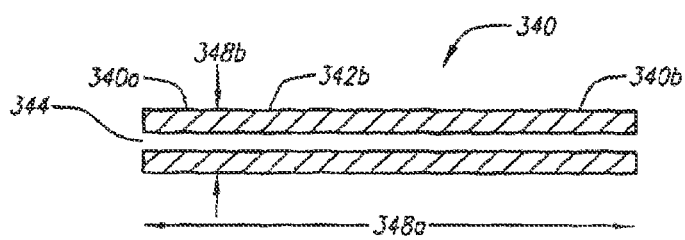
FIG. 3E illustrates one embodiment of a support member for the carrier assembly of FIG. 3A.

It will be appreciated that the tube set 305 can also include a support member 340 as shown in FIGS. 3A and 3E. The support member 340 is configured to slidably receive the tubular body 210 of the locator assembly 200 and to provide radial support for the distal end region 210b of the tubular body 210 when the locator assembly 200 is coupled with the carrier assembly 300. The carrier assembly 300 can advantageously include the support member 340, for example, if the tubular body 210 is not sufficiently rigid or under other circumstances in which support for the tubular body 210 might be desirable. It also will be appreciated that the support member 340 also can be configured to inhibit the plurality of longitudinal extensions 335, which extend from the distal end region 330b of the cover member 330, from expanding prematurely prior to the closure element 500 being deployed.

The support member 340 can be formed as a substantially rigid, semi-rigid, or flexible tubular member, having a proximal end region 340a and a distal end region 340b. Wherein an outer periphery 342b of the support member 340 can define a lumen 344 that extends substantially between the proximal end region 340a and the distal end region 340b, the lumen is configured to slidably receive and support at least a portion of the tubular body 210 of the locator assembly 200. The support member 340, in turn, can be at least partially slidably disposed within the lumen 314 of the carrier member 310 such that the tubular body 210 of the locator assembly 200 may be coupled with, and slidable relative to, the carrier member 310 in the manner described in more detail above. The support member 340 can have a predetermined length 348a and a predetermined cross-section 348b, both of which can be of any suitable dimension, and the cross-section 348b can be substantially uniform. Although shown and described as being substantially separate for purposes of illustration, it will be appreciated that the carrier member 310, the pusher member 320, the cover member 330, and/or the support member 340 can be provided, in whole or in part, as one or more integrated assemblies.

In one embodiment, the support tube 340 can be configured as a hemostatic tube as described herein, and all references to the support tube 340 can also refer to the hemostasis tube 201 or like hemostatic member.

C. Clip Applier Components

The carrier assembly 300 may further include a housing 380 as illustrated in FIG. 4A. In one configuration, the housing 380 can be formed as an elongate member with a longitudinal axis 386. The housing 380 can have an outer periphery 382b and can include a proximal end region 380a and a distal end region 380b. Thereby, when the apparatus 100 can be properly assembled, the tubular body 210 of the locator assembly 200 and hemostasis tube 201 at least partially disposed within the tube set 305 such that the distal end region 210b of the tubular body 210 and distal end region 201b of the hemostasis tube 201 extends beyond the distal end regions 310b, 320b, 330b, and/or 340b. The tubular body 210, hemostasis tube 201, the carrier member 310, the pusher member 320, the cover member 330, and, if provided, the support member 340 can be at least partially disposed within, and slidable relative to, the housing 380, and the respective distal end regions 201b, 210b, 310b, 320b, 330b, and 340b extend from the distal end region 380b of the housing 380 such that the common longitudinal axis 350 (shown in FIG. 3A) of the tube set 305 is substantially axially aligned with the longitudinal axis 386 of the housing 380. Being configured to slidably retain the respective proximal end regions 201a, 210a, 310a, 320a, 330a, and 340a, the housing 380 supports the tube set 305 and can have one or more handles 390 to facilitate use of the apparatus 100. The handles 390 extend substantially radially from the outer periphery 382b of the housing 380 and can be provided in the manner known in the art.

When the apparatus 100 is properly assembled, the tubular body 210 of the locator assembly 200 and the hemostasis tube 201 can be at least partially disposed within the tube set 305 of the carrier assembly 300 such that the distal end region 210b of the tubular body 210 and distal end region 201b of the hemostasis tube 201 extend beyond the distal end regions 310b, 320b, 330b, and/or 340b. Further, the proximal end region 210a of the tubular body 210 and hemostasis tube 201 and the proximal end regions 310a, 320a, 330a, and/or 340a of the tube set 305 are at least partially disposed within, and slidable relative to, the housing 380. The switching system of the locator assembly 200 and a switching system 450 of the triggering system 400 can be accessible external to the housing 380 as shown in FIGS. 4A and 4C.

D. Triggering System

Figure 4C:
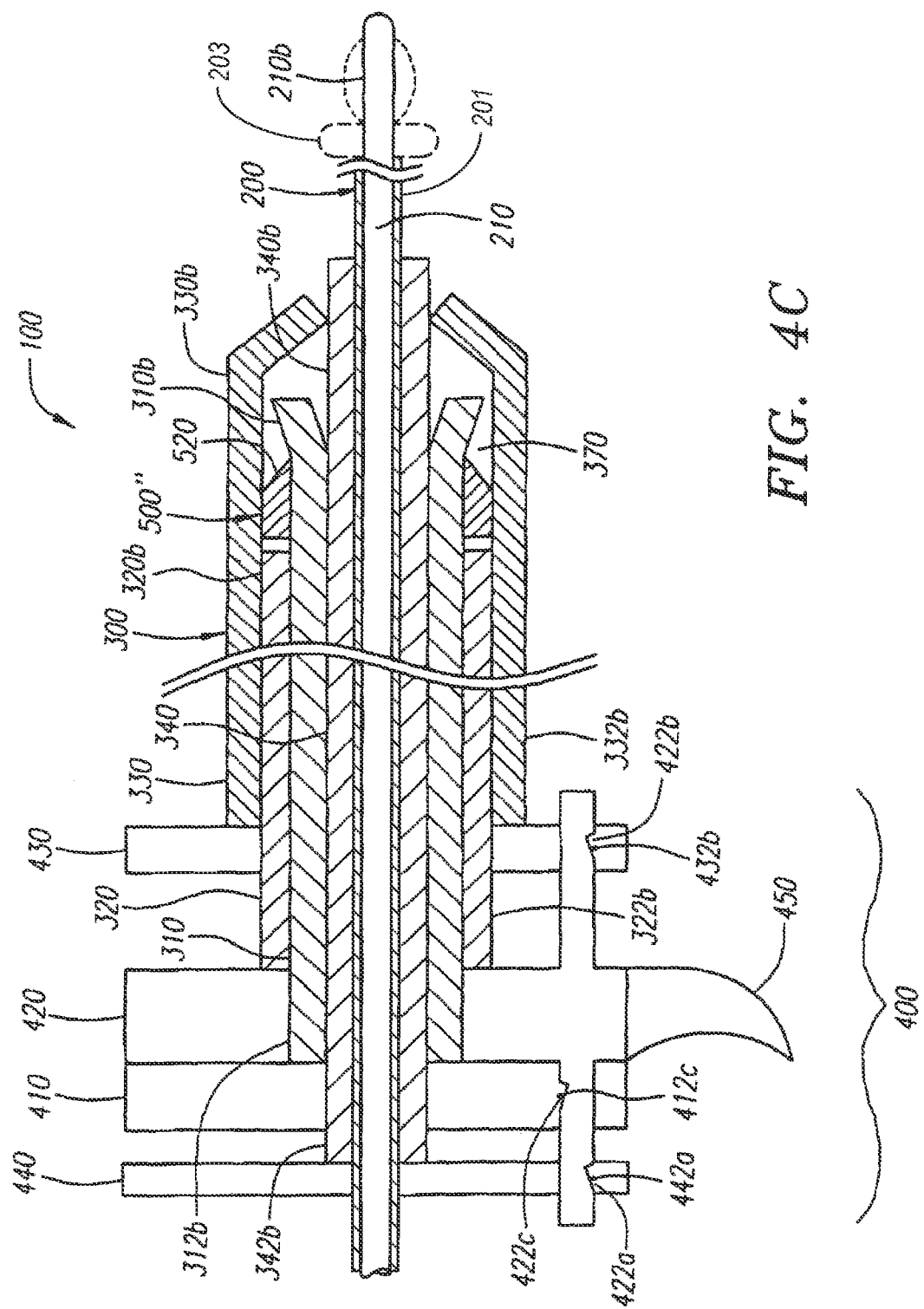
FIG. 4C illustrates a detailed view of the triggering system of FIG. 4B.
Figure 4D:
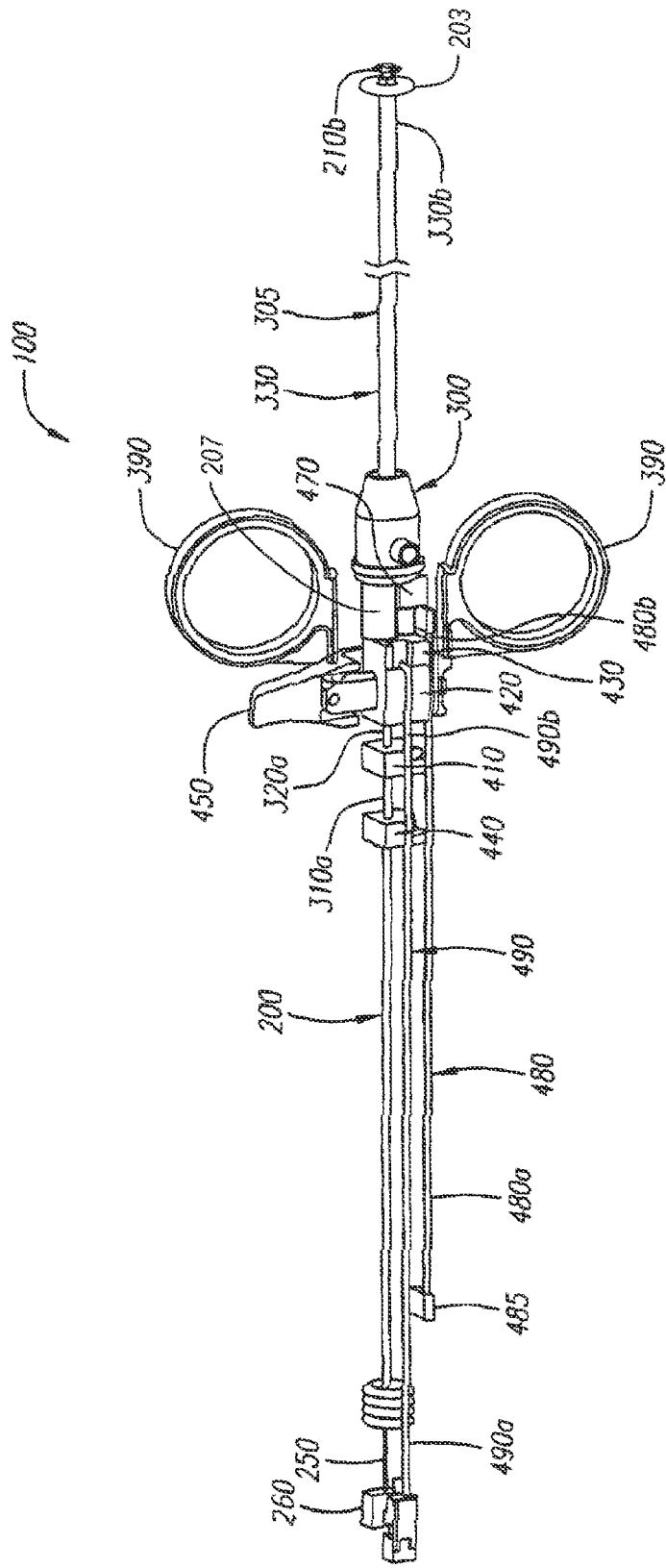
FIG. 4D illustrates a second detailed cross-sectional side view of the triggering system of FIG. 4A.

Turning to FIGS. 4B-4D, a triggering system 400 can be disposed substantially within the housing 380. The triggering system 400 can be configured to control the relative axial movement and/or positioning of the respective distal end regions 310b, 320b, 330b, and 340b of the tube set 305 and/or the distal end region 210b of the locator assembly 200 and the distal end 201b of the hemostasis tube 201. Being coupled with the proximal end regions 201a, 210a, 310a, 320a, 330a, and/or 340a, the triggering system 400 can control the relative axial movement of the distal end regions 201b, 210b, 210b, 310b, 320b, 330b, and/or 340b in any manner, such as by being activated by the switching system 450. As desired, the triggering system 400 can induce axial motion, such as distal motion, with respect to one or more of the distal end regions 201b, 210b, 310b, 320b, 330b, and/or 340b. One or more of the distal end regions 201b, 210b, 310b, 320b, 330b, and/or 340b can be axially moved. Axial motion of one or more of the carrier member 310, the pusher member 320, the cover member 330, and the support member 340 and/or the tubular body 210 can be attained, for example, by applying an axial force to the switching system 450. To facilitate monitoring of the positioning of the carrier assembly 300 and/or the substantially tubular closure element 500", one or more of the distal end regions 201b, 210b, 310b, 320b, 330b, and/or 340b may include radiopaque markers (not shown) or may be wholly or partially formed from a radiopaque material.

The triggering system 400 can be configured to overcome internal resistance such that the relative axial movement and/or positioning of the respective distal end regions 310b, 320b, 330b, and 340b of the tube set 305 and/or the distal end region 210b of the locator assembly 200 and/or distal end region 210b of the hemostasis tube 203 are controlled in accordance with a predetermined manner when the triggering system 400 is activated. Thereby, movement and/or positioning of the distal end regions 310b, 320b, 330b, 340b, and/or 210b can be initiated when at least a predetermined quantity of force is applied to the switching system 450. Stated somewhat differently, a force that is less than the predetermined quantity generally may be insufficient to activate the triggering system 400; whereas, when the force increases to a level that is greater than or substantially equal to the predetermined quantity, the triggering system 400 is configured to activate, move and/or position the distal end regions 310b, 320b, 330b, 340b, and/or 210b in accordance with the predetermined manner. The triggering system 400, once activated, can continue to move and/or position the distal end regions 310b, 320b, 330b, 340b, 201b, and/or 210b in accordance with the predetermined manner until the closure element 500 is deployed.

The triggering system 400, for example, can include one or more sets of cooperating detents for coupling the axial motion of the distal end regions 310b, 320b, 330b, and 340b in accordance with a predetermined manner when the triggering system 400 is activated. The term "detents" refers to any combination of mating elements, such as blocks, tabs, pockets, slots, ramps, locking pins, cantilevered members, support pins, and the like, that may be selectively or automatically engaged and/or disengaged to couple or decouple the carrier member 310, the pusher member 320, the cover member 330, and the support member 340 relative to one another. It will be appreciated that the cooperating detents as illustrated and described below are merely exemplary and not exhaustive. For example, the cooperating detents can include a first set of cooperating blocks and pockets for releasably coupling the support member 340, the carrier member 310, the pusher member 320, and the cover member 330. When the carrier assembly 300 reaches a first predetermined distal position, the support member 340 can be decoupled from the carrier member 310, the pusher member 320, and the cover member 330 and can be substantially inhibited from further axial movement. Thereby, the carrier member 310, the pusher member 320, and the cover member 330 may continue to be directed distally as the support member 340 remains substantially stationary.

As shown in FIGS. 4B-4C, the cooperating detents can include a carrier block 410, a pusher block 420, a cover block 430, and a support block 440, which can be configured to couple and decouple in accordance with the predetermined manner. For example, the carrier block 410 can be disposed on the proximal end region 310a of the carrier member 310 and can include a carrier pin 412c that extends from the carrier block 410; whereas, the proximal end region 330a of the cover member 330 and the proximal end region 340a the support member 340 are respectively coupled with the cover block 430 and the support block 440. A cover pin 432b can extend from the cover block 430, and the support block 440 can have a support pin 442a, which extends from the support block 440. The support pin 442a, the cover pin 432b, and the carrier pin 412c each can be formed from a substantially rigid material, such as an alloy of nickel-titanium.

The pusher block 420 can be disposed on the proximal end region 320a of the pusher member 320 and forms a support slot 422a, a cover slot 422b, and a carrier slot 422c. The support slot 422a can be configured to receive and releasable engage the support pin 442a by which the support member 340 can be coupled with, and decoupled from, the pusher member 320. The cover member 330 can be coupled with, and decoupled from, the pusher member 320 via the cover slot 422b, which is configured to receive and releasable engage the cover pin 432b. The carrier slot 422c can be configured to receive and releasable engage the carrier pin 412c such that the carrier member 310 can be coupled with, and decoupled from, the pusher member 320. The carrier block 410, the pusher block 420, the cover block 430, and the support block 440 can be respectively disposed substantially on the outer peripheries 312b, 322b, 332b, and 342b and can be configured to couple and decouple in accordance with the predetermined manner.

The triggering system 400 can further include one or more stops for engaging the pusher block 420, the cover block 430, and/or the support block 440, respectively. As illustrated in FIG. 4B, a support stop 460a, a cover stop 460b, and a carrier stop 460c each can be formed in the housing 380 and are configured to receive, and substantially inhibit further movement of, the support block 440, the cover block 430, and the carrier block 410, respectively, in accordance with the predetermined manner. For example, when an axial force is applied to the tube set 305 via the switching system 450, the cover block 430 can move distally within the housing 380, and the cover block 430 approaches the cover stop 460b. Upon being received by the cover stop 460b, the cover block 430 can be substantially locked in place, substantially preventing any further motion of the cover block 430.

Resisting the axial force, the cover pin 432b can provide a static load while the axial force is less than the predetermined quantity of force. As the axial force increases to a level that is greater than or substantially equal to the predetermined quantity, the cover pin 432b can be displaced from the cover slot 422b, decoupling the cover member 330 from the carrier member 310, the pusher member 320, and the support member 340. Creating the internal resistance to be overcome by the triggering system 400, the static forces provided by the pins 442a, 432b, and 412c is approximately proportional to a composition and cross-section of the respective pins 442a, 432b, and 412c and/or a depth and a slope of the respective slots 422a, 422b, and 422c. As desired, the pins 442a, 432b, and 412c can be configured to provide static loads that are differing and/or substantially uniform.

Additionally, FIG. 4B shows that the triggering system 400 can further include one or more stops for engaging the hemostasis block 205. The triggering system and hemostasis block 205 cooperate and function so as to selectively extend and/or retract the hemostasis tube 201. As such, the triggering system 400 and hemostasis block 205 can include additional elements not shown such that the hemostasis block 205 can control the hemostasis tube 201.

Turning to FIG. 4D, the triggering system 400 may further include a tube release system 470 for inhibiting inadvertent advancement of the tube set 305. The tube release system 470 is coupled with a tube release member 480, such as a rod, wire, or other elongate member. The tube release member 480 has a proximal end region 480a that is disposed substantially between the pusher block 420 and the housing 380 (shown in FIG. 4A) and a distal end region 480b that is coupled with the tube release system 470. A tab 485 can be coupled with the proximal end region 480a of the tube release member 480, and a pin (not shown) extends from the pusher block 420 and is disposed substantially between the tab 485 and a groove (not shown) formed in the housing 380. The tube release system 470 is configured to release the tube set 305 when the tube release member 480 is moved proximally, freeing the pusher block 420. The tube release system 470 can also function similarly with the hemostasis block 205 and hemostasis tube 201.

A locator release system 490 for permitting the distal end region 210b, the expansion elements 230, and/or the substantially flexible members 230' of the locator assembly 200 to transition from the expanded state to the unexpanded state can be included with the triggering system 400. The locator release system 490 can include a rod, wire, or other elongate member and has a proximal end region 490a and a distal end region 490b. The proximal end region 490a of the locator release system 490 can be coupled with, and configured to activate, the locator control system 240 (shown in FIG. 2D), and the distal end region 490b extends beyond the pusher block 420. Thereby, when the pusher block 420 is advanced during deployment of the closure element 500, the control block 260 can be disengaged such that the distal end region 210b, the expansion elements 230, and/or the substantially flexible members 230' of the locator assembly 200 to transition from the expanded state to the unexpanded state. The locator release system 490 can also function similarly with the hemostasis block 205, hemostasis tube 201, and hemostasis member 203. Alternatively, the hemostasis block 205, hemostasis tube 201, and hemostasis member 203 can be operated by a hemostasis release system (not shown), which functions similarly to the locator release system 490.

Figure 5C:
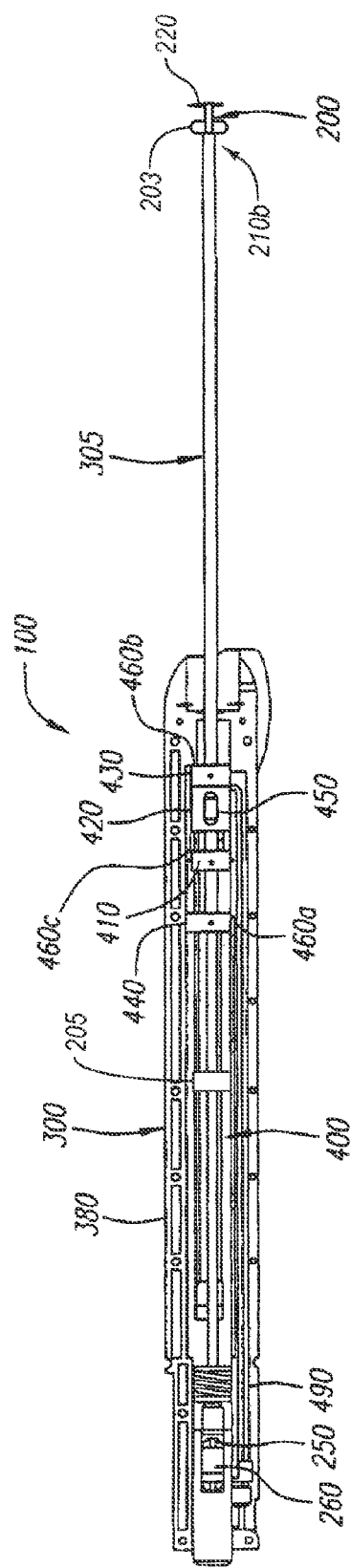
FIG. 5C illustrates the carrier control system of FIGS. 4A-4D as the carrier assembly of FIG. 3A reaches a second predetermined position.

The operation of the triggering system 400 in accordance with one predetermined manner is illustrated in FIGS. 5A-5C with the closure element 500 (shown in FIGS. 6A-6B) disposed substantially within the apparatus 100. As shown in FIG. 5A, the distal end region 210b of the locator assembly 200 has been positioned as desired and the locator member 220 and hemostasis member 203 each has transitioned from the unexpanded state to the expanded state. While the locator control system 240 (shown in FIG. 2D) maintains the locator member 220 and hemostasis member 203 in the expanded state, a distally-directed axial force can be applied to the triggering system 400 via the switching system 450. Once the tube release member 480 (shown in FIG. 4D) has been moved proximally to free the pusher block 420, the tube set 305 can be substantially freely slidable within the housing 380 and responds to the axial force by sliding distally from an initial predetermined position to a first predetermined position.

In the initial predetermined position, the carrier member 310, the pusher member 320, the cover member 330, and the support member 340 can be coupled via the slots 422c, 422b, and 422a (shown in FIG. 4C) and the pins 412c, 432b, and 442a (shown in FIG. 4C). Stated somewhat differently, the support pin 442a, the cover pin 432b, and the carrier pin 412c can be respectively disposed within, and engaged by, the support slot 422a, the cover slot 422b, and the carrier slot 422c such that the carrier block 410, the pusher block 420, the cover block 430, and the support block 440 are coupled as illustrated in FIG. 4C. Therefore, the carrier member 310, the pusher member 320, the cover member 330, and the support member 340 each can slide distally from the initial predetermined position to the first predetermined position in response to the axial force.

FIG. 5B illustrates the positions of the carrier member 310, the pusher member 320, the cover member 330, and the support member 340 upon reaching the first predetermined position. In the first predetermined position, the support block 440 and the cover block 430 can respectively engage the support stop 460a and the cover stop 460b. Thereby, the support stop 460a can receive, and substantially inhibit further movement of, the support block 440 and, therefore, the support member 340; whereas, the cover stop 460b receives, and substantially inhibits further movement of, the cover block 430 and, therefore, the cover member 330. Although the support block 440 and the cover block 430 can engage the support stop 460a and the cover stop 460b in the first predetermined position, it will be appreciated that the support block 440 can engage the support stop 460a and the cover block 430 can engage the cover stop 460b in different predetermined positions. In other words, the predetermined manner can include any number of predetermined positions, each predetermined position being associated with any number of the blocks 410, 420, 430, and 440 engaging any number of relevant stops 460a, 460b, and 460c. The hemostasis tube 201 and/or hemostasis member 203 can be similarly controlled with the hemostasis block 205 and stops (not shown).

To continue distally from the first predetermined position, the carrier member 310 and the pusher member 320 can be decoupled from the cover member 330 and the support member 340 by disengaging the support pin 442a and the cover pin 432b from the support slot 422a and the cover slot 422b, respectively. In the manner described in more detail above with reference to FIGS. 4B-4C, the support pin 442a and the cover pin 432b each resist the axial force. While the axial force is less than the combined static force provided by the support pin 442a and the cover pin 432b, the carrier member 310 and the pusher member 320 remain coupled with the cover member 330 and the support member 340. As the axial force increases to a level that is greater than or substantially equal to the combined static force, the support pin 442a and the cover pin 432b are respectively displaced from the support slot 422a and the cover slot 422b, decoupling the carrier member 310 and the pusher member 320 from the cover member 330 and the support member 340. Thereby, the cover member 330 and the support member 340 can be inhibited from further distal movement and remain substantially stationary; whereas, the carrier member 310 and the pusher member 320 can proceed distally toward a second predetermined position.

The pusher member 320 and the carrier member 310 can continue distally until the second predetermined position is reached as shown in FIG. 5C. In the second predetermined position, the carrier block 410 can engage the carrier stop 460c. Whereby, the carrier stop 460c can receive, and substantially inhibit further movement of, the carrier block 410 and, therefore, the carrier member 310. To continue distally from the second predetermined position, the pusher member 320 can be decoupled from the carrier member 310 by disengaging the carrier pin 412c from the carrier slot 422c. In the manner described in more detail above with reference to FIG. 4B-C, the carrier pin 412c resists the axial force. While the axial force is less than the static force provided by the carrier pin 412c, the pusher member 320 remains coupled with the carrier member 310.

As the axial force increases to a level that is greater than or substantially equal to the static force, the carrier pin 412c can be displaced from the carrier slot 422c, decoupling the pusher member 320 from the carrier member 310. Thereby, the carrier member 310 can be inhibited from further distal movement and remains substantially stationary; whereas, the pusher member 320 proceeds distally to deploy the closure element 500 and to activate the locator release system 490 (shown in FIG. 4D) such that the distal end region 210b, the expansion elements 230, and/or the substantially flexible members 230' of the locator assembly 200 as well as the hemostasis member 203 transition from the expanded state to the unexpanded state. The axial force that is applied to overcome the static force associated with the first predetermined position can be sufficient to overcome the static forces associated with the subsequent predetermined positions, to deploy the closure element 500, and to activate the locator release system 490 such that the triggering system 400 operates in one substantially-continuous motion. When the locator 220 is implantable, the process can release the locator 220 as the closure element 500 penetrates through the vessel wall and grabs the locator 220 to hold it in place.

It will be appreciated that the triggering system 400 can include an energy storing element (not shown), which can be disposed substantially between the housing 380 and the blocks 410, 420, 430, and 440 and which can be configured to store potential energy for moving the tube set 305 from the initial predetermined position through the other predetermined positions, deploying the closure element 500, and/or activating the locator release system 490. The energy-storing element can be configured store the potential energy when the tube set 305 is in the initial predetermined position and to release the potential energy, when activated, such that the tube set 305 travels through the predetermined positions at a substantially constant and continuous rate. For example, the energy-storing element can include one or more springs (not shown). Each of the springs can be in a compressed state when the tube set 305 is in the initial predetermined position and released from the compressed state when the switching system 450 of the triggering system 400 is activated. The triggering system 400 can be similarly configured for the block 205 and hemostasis tube 201 and/or hemostasis member 203.

E. Delivering Closure Element

Figure 7A:
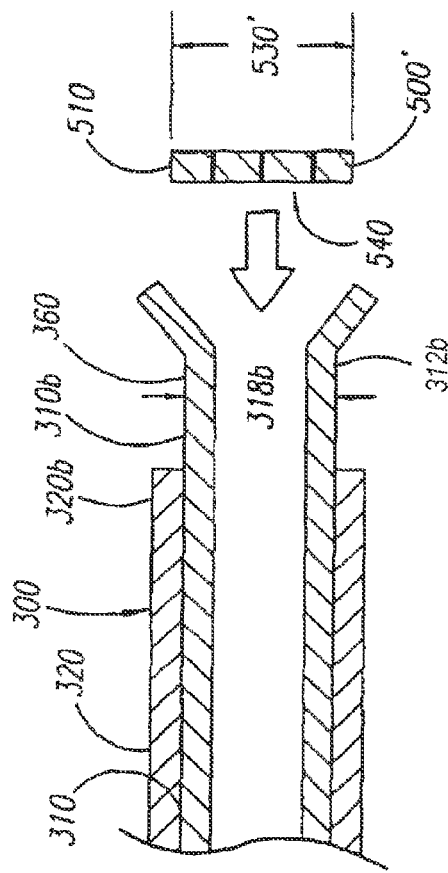
FIG. 7A illustrates the closure element of FIGS. 6A-6G prior to being disposed upon the carrier member of FIG. 3B.
Figure 7B:
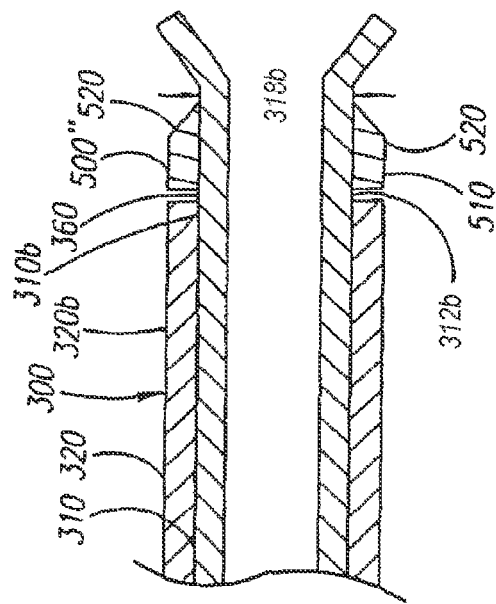
FIG. 7B illustrates the closure element of FIGS. 6A-6G upon being disposed upon the carrier member of FIG. 3B.

In use, the closure element 500 can be disposed within the carrier assembly and adjacent to the distal end of the pusher tube 320. As shown in FIGS. 7A-7B, for example, the reduced closure element 500' can be slidably received over the distally-increasing cross-section 318b of the distal end region 310b of the carrier member 310 and disposed about the periphery 312 of the carrier member 310 adjacent to the space 360. Since the reduced cross-section 530' of the reduced closure element 500' is less than the cross-section 318b of the distally-increasing cross-section 318b, the reduced closure element 500' must be temporarily radially deformed to be received over the distal end region 310b. Also, as the reduced closure element 500' is received over the distal end region 310b, the opposing tines 520 of the reduced closure element 500' engages the distal end region 310b. The reduced closure element 500' thereby can form the substantially tubular closure element 500" in the manner described in more detail above with reference to FIGS. 6E-6G.

After being received over the distal end region 310b, the substantially tubular closure element 500" can be disposed about the space 360, and the tines 520 are directed substantially distally as shown in FIG. 7B. As desired, one or more of the tines 520 can be disposed proximally of the distally-increasing cross-section 318b of the distal end region 310b, as illustrated in FIG. 7B, and/or can be at least partially disposed upon, and contact, the distally-increasing cross-section 318b of the distal end region 310b. To improve the engagement between the closure element 500 (shown in FIGS. 6A-6B) and the blood vessel wall 620 and/or tissue 630 (collectively shown in FIG. 8A), the substantially tubular closure element 500" can be disposed on the carrier member 310 such that the tines 520 define a first plane that is substantially perpendicular to a second plane defined by the switching system 450 and/or the handles 390 (collectively shown in FIG. 5A).

Figure 7C:
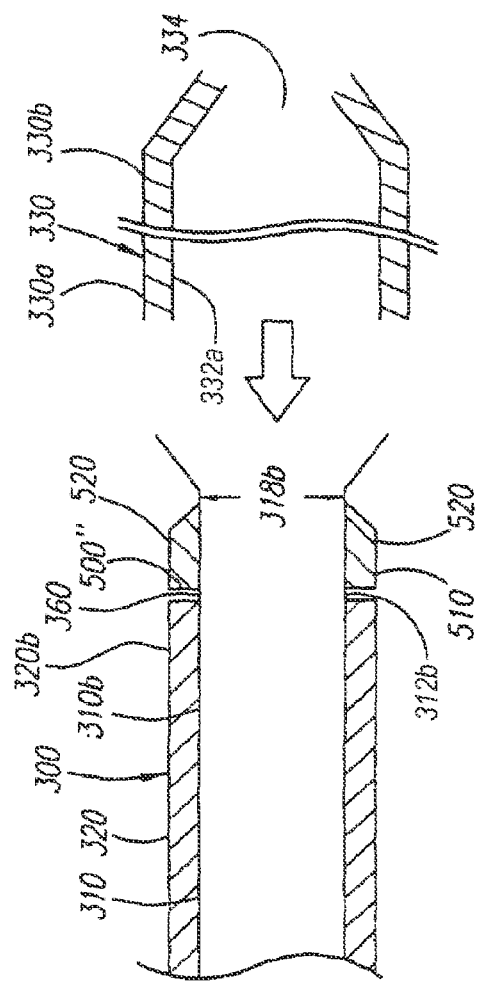
FIG. 7C illustrates the closure element of FIGS. 6A-6G as the cover member of FIG. 3D receives the carrier member of FIG. 3B.
Figure 7D:
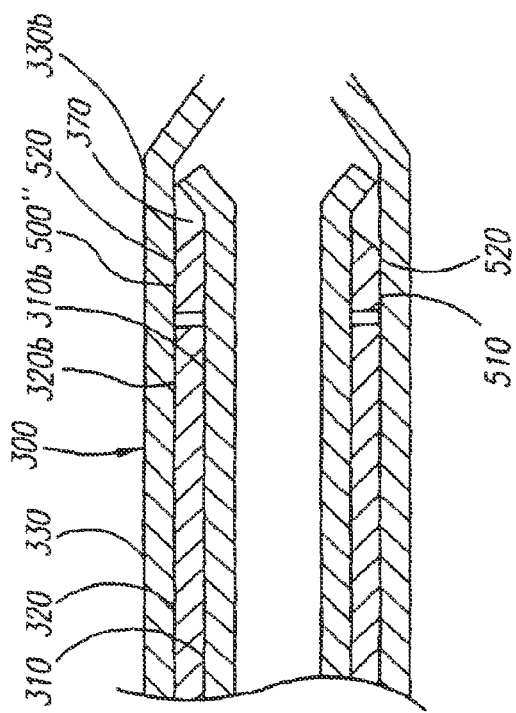
FIG. 7D illustrates the closure element of FIGS. 6A-6G being retained substantially within the carrier assembly of FIG. 3A when the carrier member of FIG. 3B is disposed substantially within the cover member of FIG. 3D.

Once disposed about the space 360, the substantially tubular closure element 500" can be retained on the outer periphery 312b of the carrier member 310 when distal end region 310b of the carrier member 310 and the distal end region 320b of the pusher member 320 are slidably received within the lumen 334 of the cover member 330 as illustrated in FIGS. 7C-7D. When the cover member 330 is properly positioned within the carrier assembly 300, the distal end region 330b of the cover member 330 can extend over the space 360 and defines the annular cavity 370 for retaining the substantially tubular closure element 500". As such, the substantially tubular closure element 500" is disposed substantially between the outer periphery 312b of the carrier member 310 and the inner periphery 332a of the cover member 330 such that the substantially tubular closure element 500" maintains the substantially tubular configuration with the tines 520 being directed substantially distally. As desired, the cover member 330 may radially compress the substantially tubular closure element 500" such that the substantially tubular closure element 500" enters and maintains a compressed tubular configuration. The body 510 of the substantially tubular closure element 500" can be disposed distally of the distal end region 320b of the pusher member 320, as illustrated in FIGS. 7C-7D, or can engage the distal end region 320b, as desired.

Figure 8A:
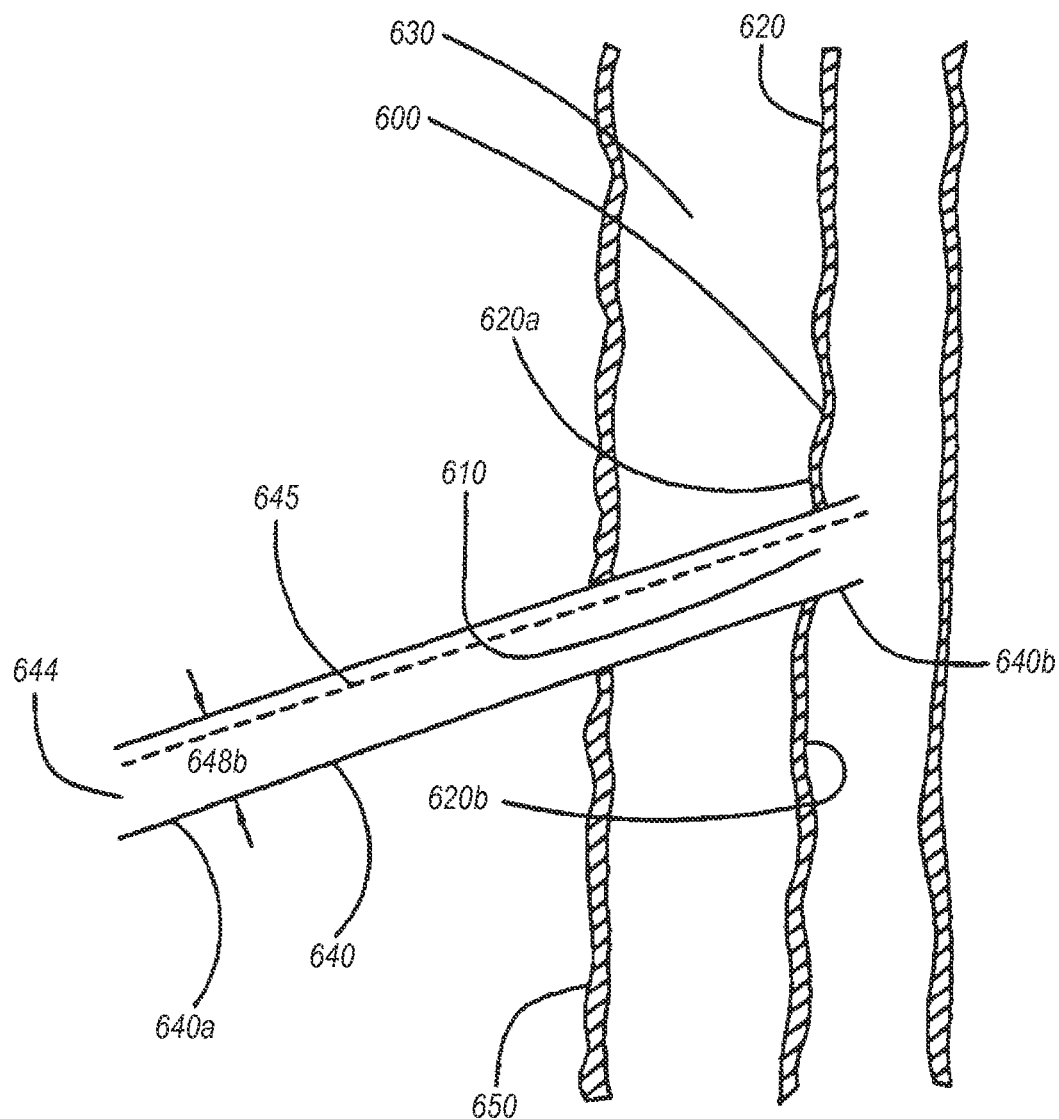
FIG. 8A illustrates a sheath that is positioned through tissue and into an opening formed in a wall of a blood vessel.

Turning to FIG. 8A, a sheath 640 may be inserted or otherwise positioned through skin 650 and tissue 630 and within the blood vessel 600 or other body lumen via the opening 610. The sheath 640 can include a substantially flexible or semi-rigid tubular member. Also, the sheath 640 can have a proximal end region 640a and a distal end region 640b and includes a predetermined length and a predetermined cross-section, both of which can be of any suitable dimension. The sheath 640 also can form a lumen 644 that extends along a longitudinal axis of the sheath 640 and substantially between the proximal and distal end regions 640a, 640b. The lumen 644 can have any suitable internal cross-section 648b and is suitable for receiving one or more devices (not shown), such as a catheter, a guide wire, or the like. The lumen 644 can be configured to slidably receive the tubular body 210 and hemostasis tube 201 of the assembly 200 (shown in FIG. 4A) and/or the tube set 305 of the carrier assembly 300 (shown in FIG. 4A).

Since the internal cross-section 648b of the sheath 640 typically can be less than or substantially equal to the predetermined cross-section 338b of the cover member 330, the sheath 640 may be configured to radially expand, such as by stretching, to receive the tube set 305. Alternatively, or in addition, the sheath 640 can be advantageously configured to split as the tube set 305 is received by, and advances within, the lumen 644 of the sheath 640, thereby permitting the apparatus 100 to access the blood vessel wall 620. To facilitate the splitting, the sheath 640 can include one or more splits 645, such as longitudinal splits, each split being provided in the manner known in the art. Each split 645 can be configured to split the sheath 640 in accordance with a predetermined pattern, such as in a spiral pattern. It will be appreciated that, when the internal cross-section 648b of the sheath 640 is greater than the predetermined cross-section 338b of the cover member 330, it may not be necessary for the sheath 640 to be configured to radially expand and/or split. In addition to, or as an alternative to, the apparatus 100 may include a cutting means that initiates a tear line or split in the sheath when the sheath is engaged with the distal end of the apparatus 100.

The sheath 640 may be advanced over a guide wire or other rail (not shown) which has been positioned through the opening 610 and into the blood vessel 600 using conventional procedures such as those described above. The blood vessel 600 can be a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, hemostatic assembly, or the like, may be inserted through the sheath 640 and advanced to a preselected location within the patient's body. For example, the devices may be used to perform a therapeutic or diagnostic procedure, such as angioplasty, atherectomy, stent implantation, and the like, within the patent's vasculature.

Figure 8B:
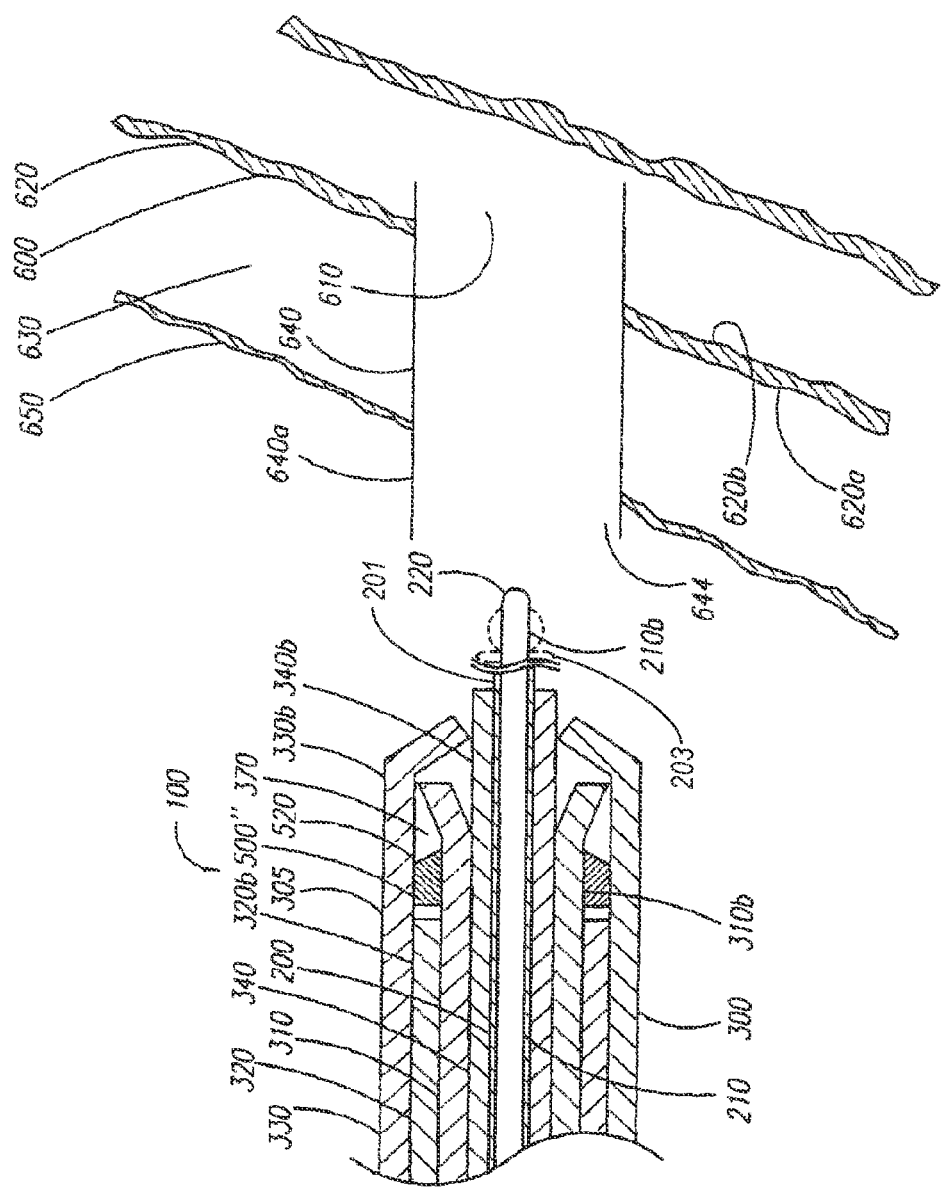
FIG. 8B illustrates the apparatus of FIG. 1 as prepared to be received by the sheath of FIG. 8A.
Figure 8C:
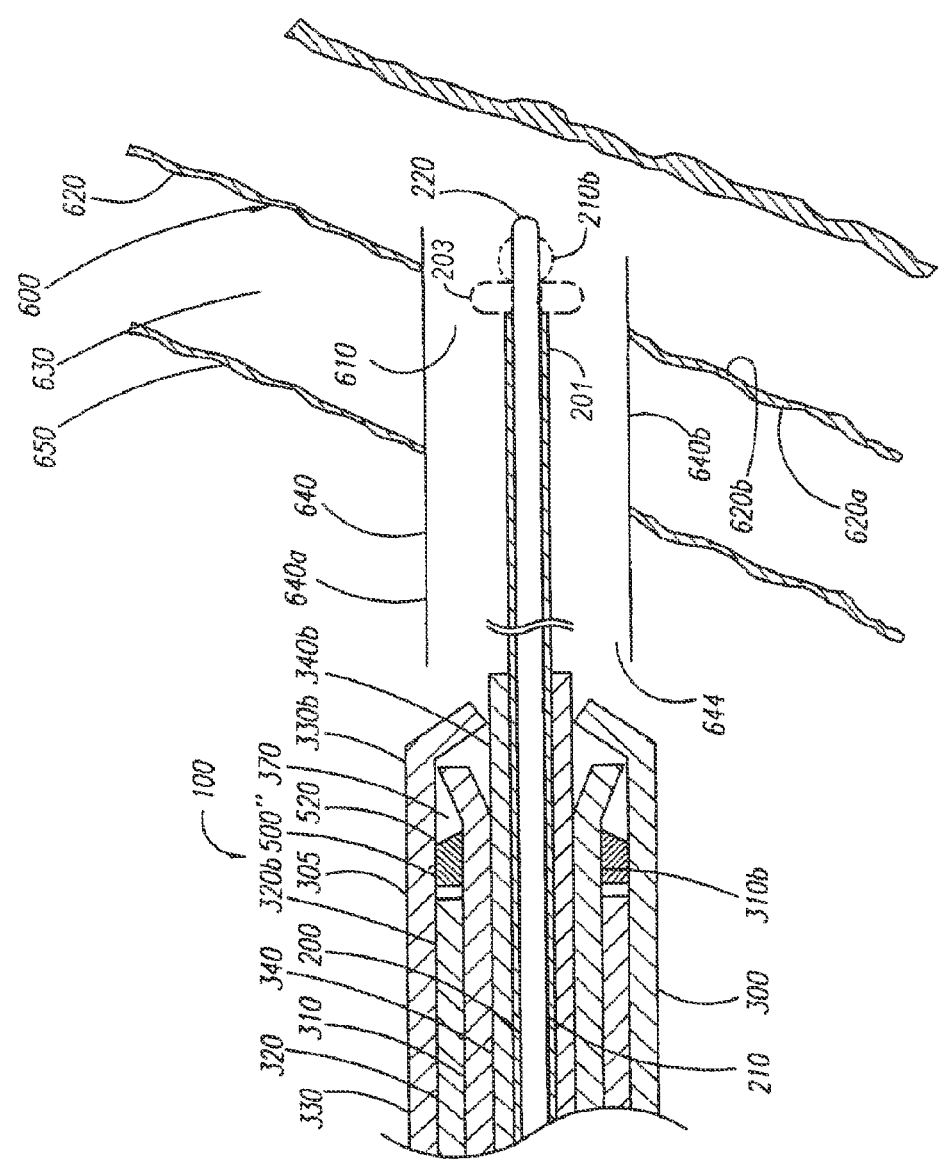
FIG. 8C illustrates a locator assembly of the apparatus of FIG. 8B being advanced distally into the blood vessel.
Figure 8D:
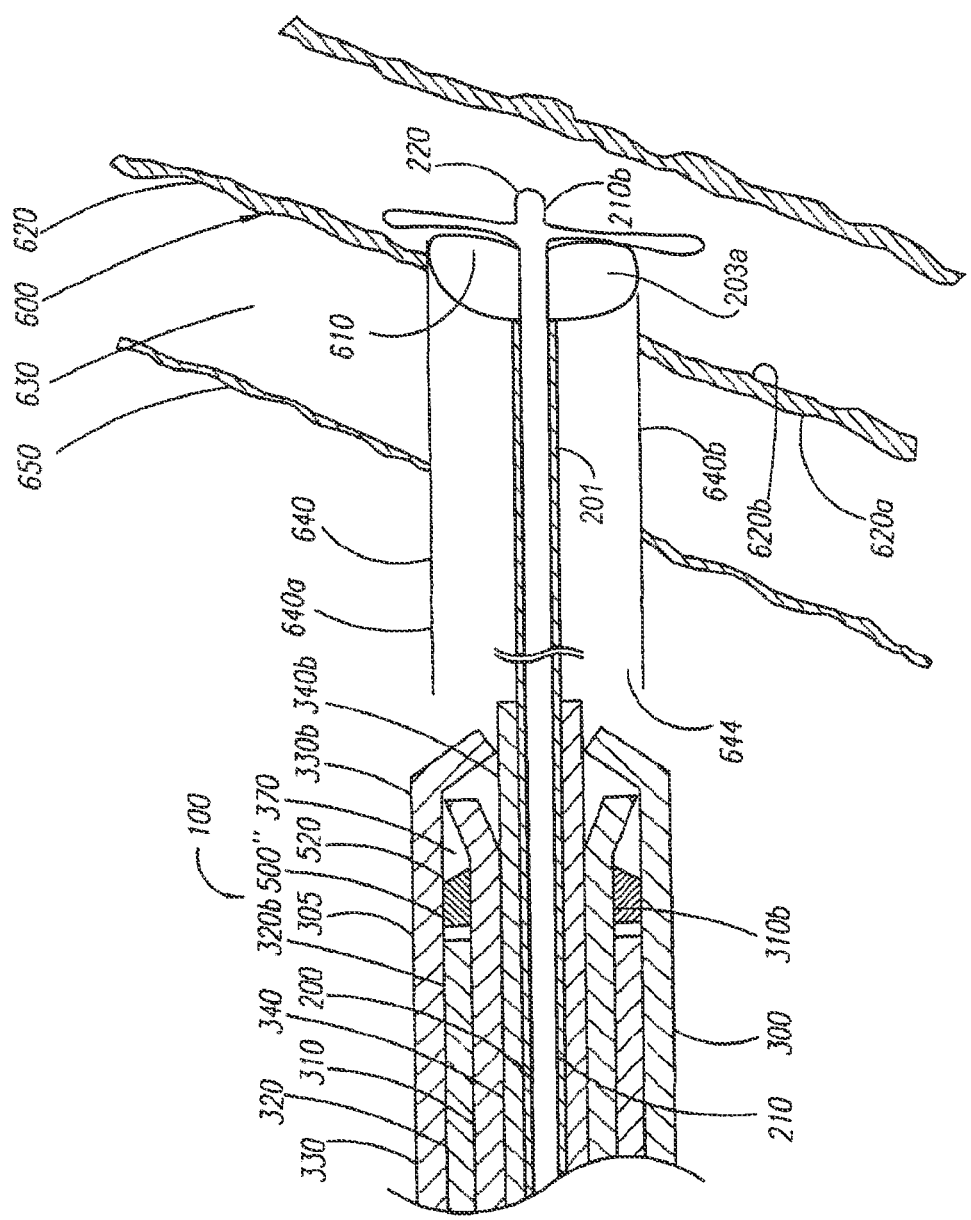
FIG. 8D illustrates a distal end region of the locator assembly of FIG. 8C extending into the blood vessel and being transitioned into an expanded state.

After the procedure is completed, the devices are removed from the sheath 640, and the apparatus 100 is prepared to be received by the lumen 644 of the sheath 640 as shown in FIG. 8B. Being in the unexpanded state, the distal end region 210*b* of the tubular body 210 and the hemostasis tube 201 and/or hemostasis member 203 of the assembly 200 can be slidably received by the lumen 644 and atraumatically advanced distally into the blood vessel 600 as illustrated in FIGS. 8B-C. Once the distal end region 210*b* of the tubular body 210 extends into the blood vessel 600, the distal end region 210*b* (e.g., locator 220) and hemostasis member 203 can transition from the unexpanded state to the expanded state as shown in FIG. 8D by activating the switching system of the locator assembly 200 or similarly configured hemostasis assembly. However, it may be desirable to expand one of the locator 220 and hemostasis member 203 individually from each other. On one example, it may be advantageous to expand the hemostasis member 203 after the locator 220 is fully expanded.

Figure 8E:
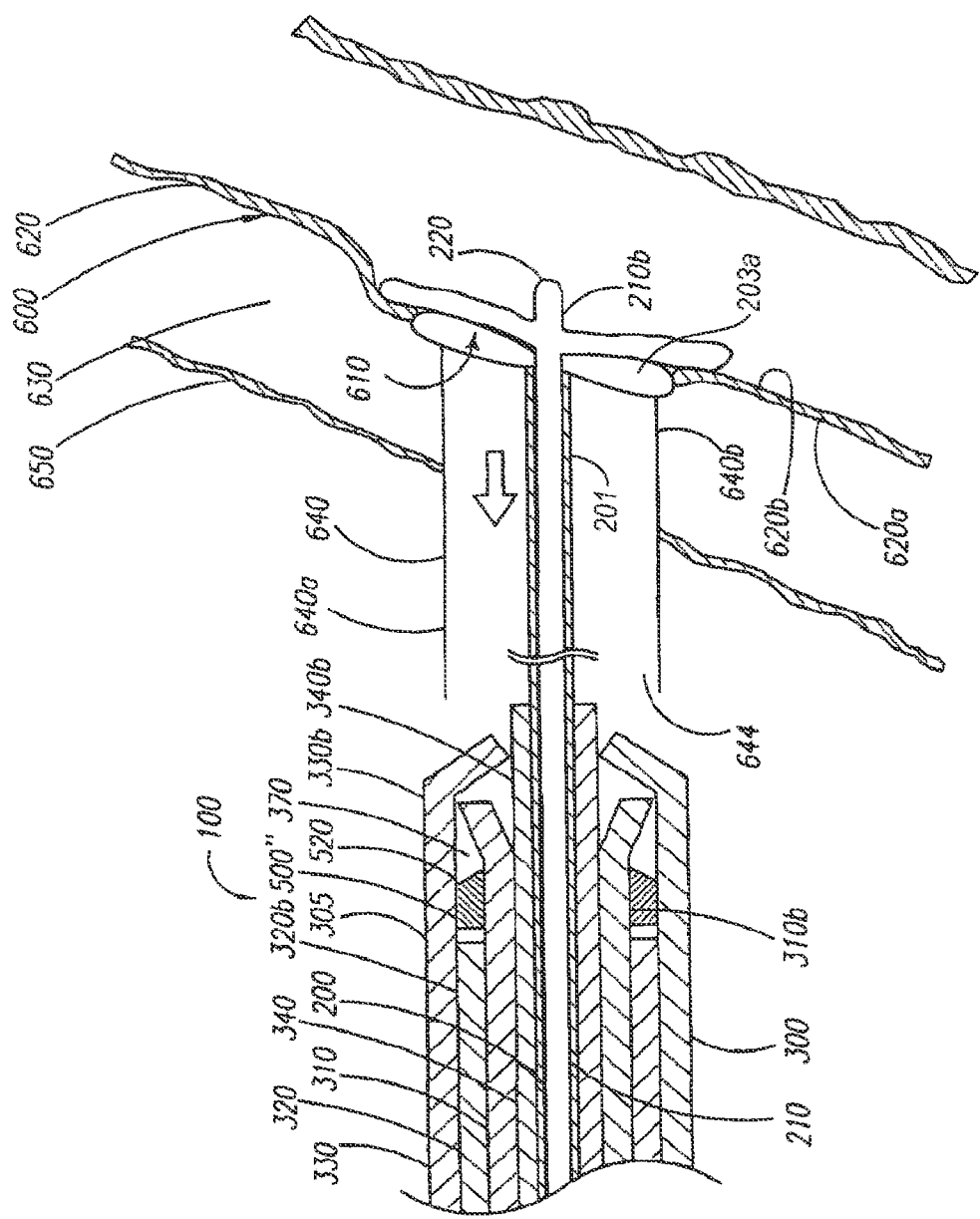
FIG. 8E illustrates the distal end region of FIG. 8D being retracted proximally to engage an inner surface of the blood vessel wall.

Turning to FIG. 8E, the apparatus 100 and the sheath 640 then can be refracted proximally until the distal end region 210*b* is substantially adjacent to an inner surface 620*b* of the blood vessel wall 620. The distal end region 210*b* thereby can draw the blood vessel wall 620 taut and maintains the proper position of the apparatus 100 as the blood vessel 600 pulsates. Since the expanded cross-section of the distal end region 210*b* or locator 220 can be greater than or substantially equal to the cross-section of the opening 610 and/or the cross-section of the lumen 644, the distal end region 210*b* or locator 220 remains in the blood vessel 600 and engages the inner surface 620*b* of the blood vessel wall 620. The distal end region 210*b* can frictionally engage the inner surface 620*b* of the blood vessel wall 620, thereby securing the apparatus 100 to the blood vessel 600. The sheath 640 can be retracted proximally such that the distal end region 640*b* of the sheath 640 is substantially withdrawn from the blood vessel 600, as shown in FIG. 8E, permitting the apparatus 100 to access the blood vessel wall 620. Such withdrawal can cause blood flow or ooze from the opening 610. As such, the hemostasis member 203 can be activated to expand radially or laterally to inhibit blood flow or ooze.

While the locator 220 of the distal end region 210*b* is being placed adjacent to the inner surface 620*b* of the blood vessel wall 620, the hemostasis member 203 can be selectively expanded so as to fill or plug the opening 610 or form a seal or partial seal with the outer surface of the vessel wall 620*b* around the opening 610 in the blood vessel 620. This can be especially advantageous as the sheath 640 is retracted from the opening 610 such that a gap forms between the walls of the opening 610 and the apparatus 100. Such a gap can allow for blood to ooze from the opening and potentially into the lumen 644 of the sheath 640. The expanded hemostasis member 203 can have an expanded cross-section that is substantially the same as, or slightly larger than, the opening 610 so that it plugs or seals the opening 610. The expanded hemostasis member 203 can thereby plug or seal the opening 610 so as to prevent blood oozing or otherwise leaking. While not shown, the radial or circumferential dimension of the hemostasis member 203 can be selectively changed and adapted to fit within or over the opening 610 and can further widen to plug or seal the opening in the tissue 630 as needed.

As the apparatus 100 is being retracted, the apparatus 100 also can be axially rotated such that the first plane defined by the tines 520 of the substantially tubular closure element 500" is substantially parallel with a third plane defined by the blood vessel 600. Thereby, the engagement between the substantially tubular closure element 500" and the blood vessel wall 620 and/or tissue 630 can be improved because the tines 520 are configured to engage the blood vessel wall 620 and/or tissue 630 at opposite sides of the opening 610. If the substantially tubular closure element 500" is disposed on the carrier member 310 such that the first plane defined by the tines 520 is from 45 degrees to substantially perpendicular to the second plane defined by the switching system 450 and/or the handles 390 (collectively shown in FIG. 5A), for example, the apparatus 100 can be positioned such that the second plane defined by the switching system 450 and/or the handles 390 is substantially perpendicular to the third plane defined by the blood vessel 600.

Figure 8F:
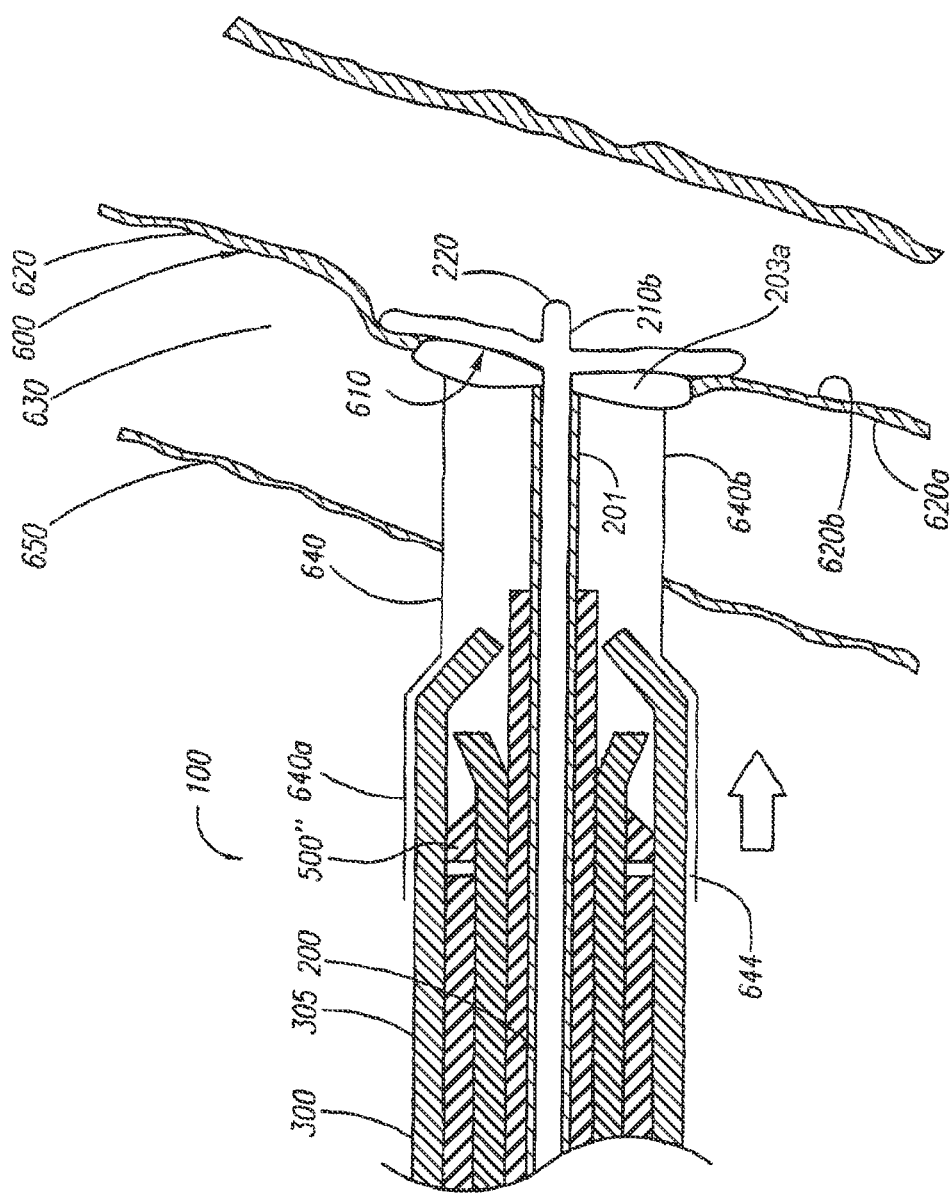
FIG. 8F illustrates a carrier assembly of the apparatus of FIG. 8B being advanced distally into the sheath of FIG. 8A once the distal end region of FIG. 8D has engaged the inner surface of the blood vessel wall.
Figure 8G:
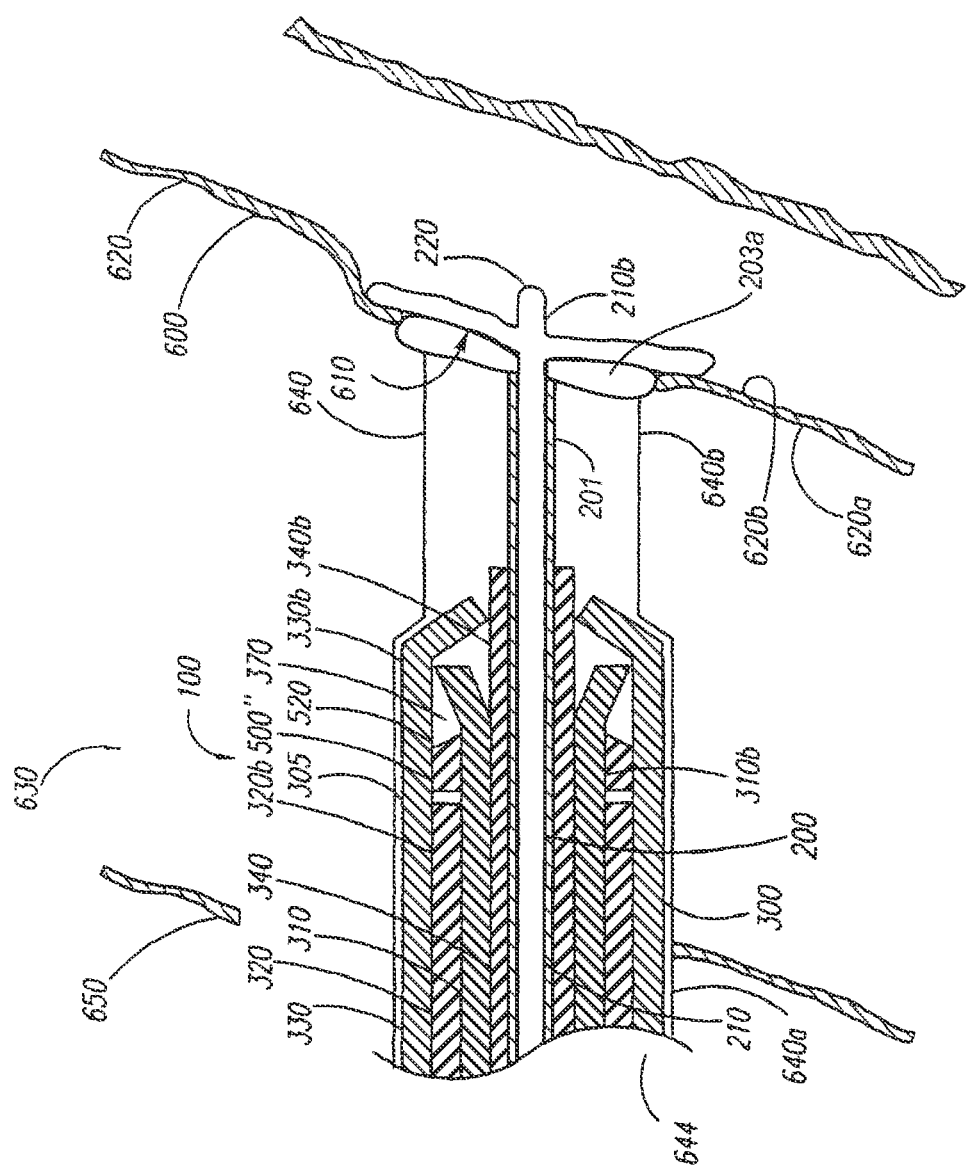
FIG. 8G illustrates relative positions of a tube set of the carrier assembly of FIG. 8F upon reaching a first predetermined position.

Once the distal end region 210*b* or locator 220 of the locator assembly 200 contacts the inner surface 620*b* of the blood vessel wall 620, and the hemostasis member 203 seals the opening 610 from oozing blood, the tube set 305 can then be advanced distally and received within the lumen 644 of the sheath 640 as illustrated in FIG. 8F. In the manner described in more detail above with reference to FIG. 8A, the sheath 640 can radially expand and/or split in accordance with the predetermined pattern as the tube set 305 advances because the internal cross-section 648*b* of the sheath 640 is less than or substantially equal to the predetermined cross-section 338*b* of the cover member 330. Being coupled, the carrier member 310, the pusher member 320, the cover member 330, and the support member 340 each advance distally and approach the first predetermined position as illustrated in FIG. 8G.

Upon reaching the first predetermined position, the tube set 305 can be disposed substantially adjacent to the outer surface 620*a* of the blood vessel wall 620 adjacent to the opening 610 and hemostasis member 203 such that the blood vessel wall 620 adjacent to the opening 610 is disposed substantially between the expanded distal region 210*b* of the locator 220 and the tube set 305. The cover member 330 and the support member 340 can each decouple from the carrier member 310 and the pusher member 320 in the manner described in more detail above with reference to FIG. 5A-5C when the tube set 305 is in the first predetermined position. Thereby, the cover member 330 and the support member 340 can be inhibited from further axial movement and remain substantially stationary as the carrier member 310 and the pusher member 320 each remain coupled and axially slidable.

As shown in FIG. 8H, the cover member 330 and the support member 340 can remain substantially stationary while the carrier member 310 and the pusher member 320 can continue distally and approach the second predetermined position. As the carrier member 310 and the pusher member 320 distally advance toward the second predetermined position, the annular cavity 370 can move distally relative to the substantially-stationary cover member 330 such that the distal end region 330b of the cover member 330 no longer encloses the annular cavity 370. Thereby, the substantially tubular closure element 500" may not be completely enclosed by the annular cavity 370 formed by the distal end regions 310b, 320b, and 330b of the carrier member 310, the pusher member 320, and the cover member 330.

Although not completely enclosed by the annular cavity 370, the substantially tubular closure element 500" can be advantageously retained on the outer periphery 312b of the carrier member 310 by the distal end region 330b of the cover member 330 as illustrated in FIG. 8H. For example, by retaining the substantially tubular closure element 500" between the distal end region 330b of the cover member 330 and the distal end region 310b the carrier member 310, the apparatus 100 can be configured to provide better tissue penetration. The timing between the deployment of the substantially tubular closure element 500" by the tube set 305 and the retraction and transition to the unexpanded state by the locator 220 and/or hemostasis member 203 likewise is facilitated because the substantially tubular closure element 500" is retained between the distal end region 330b and the distal end region 310b. Further, the carrier member 310 and the cover member 330 can operate to maintain the substantially tubular closure element 500" in the tubular configuration. Alternatively, the timing of deployment can be coordinated with release of the locator 220 as an implantable locator 220.

Figure 8I:
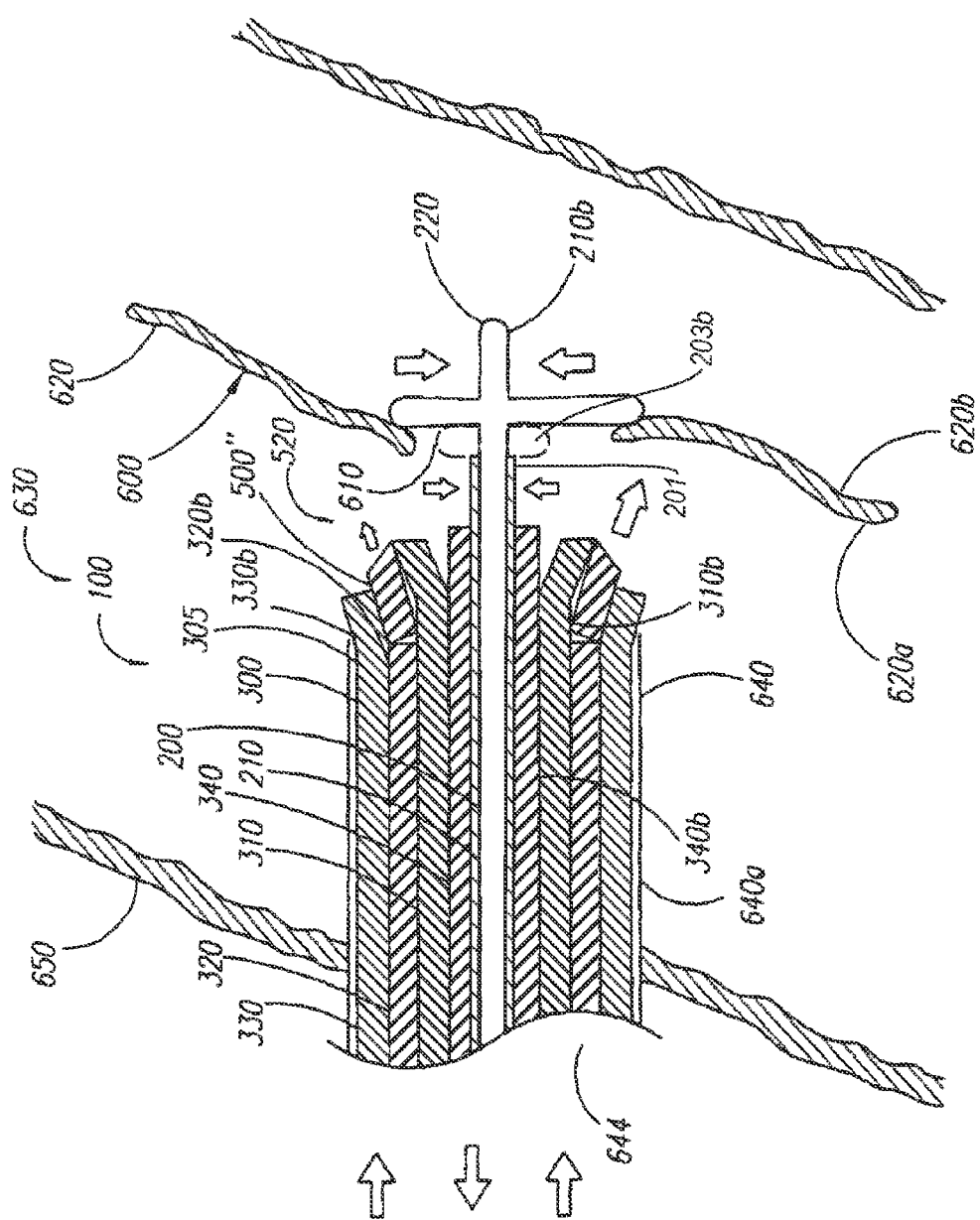
FIG. 8I illustrates a position of a pusher member of the tube set of FIG. 8H moving distally from the second predetermined position and beginning to distally deploy a closure element.

As shown in FIG. 8I, the locator 220 and hemostasis member 203b begin to retract toward the unexpanded state. This is shown by the arrows pointing inwardly adjacent to the locator 220 and the hemostasis member 203b. Alternatively, the locator 220 can be released so that the closure element 500 can grab the locator 220 and hold it against the inner wall 620a of the blood vessel.

When the tube set 305 is in the second predetermined position, the carrier member 310 can decouple from the pusher member 320 in the manner described in more detail above with reference to FIG. 5A-5C. Therefore, the carrier member 310, the cover member 330, and the support member 340 can be inhibited from further axial movement and remain substantially stationary; whereas, the pusher member 320 remains axially slidable. As the pusher member 320 continues distally, the distal end region 320b of the pusher member 320 can contact the substantially tubular closure element 500" and displaces the substantially tubular closure element 500" from the space 360 as shown in FIG. 8I. Since the space 360 is substantially radially exposed, the pusher member 320 can direct the substantially tubular closure element 500" over the distally-increasing cross-section of the distal end region 310b of the substantially-stationary carrier member 310 such that the cross-section 530' (shown in FIGS. 6F-6G) of the substantially tubular closure element 500" begins to radially expand, optionally in a substantially uniform manner. As the substantially tubular closure element 500" traverses the distally-increasing cross-section of the distal end region 310b, the cross-section 530' of the substantially tubular closure element 500" radially expands beyond natural cross-section 530 (shown in FIGS. 6A-6B) of the closure element 500.

During this period of function, the locator 220 and hemostasis member 203c continue to retract toward an unexpanded state. Also, the locator 220 and hemostasis member 203c are being withdrawn from the opening 610 so as to allow the closure element 500 to better engage the blood vessel 620 without being impaired by contacting the locator 220 or hemostasis member 203c. Alternatively, the locator 220 can be released so that it can be grabbed by the closure element 500.

Figure 8J:
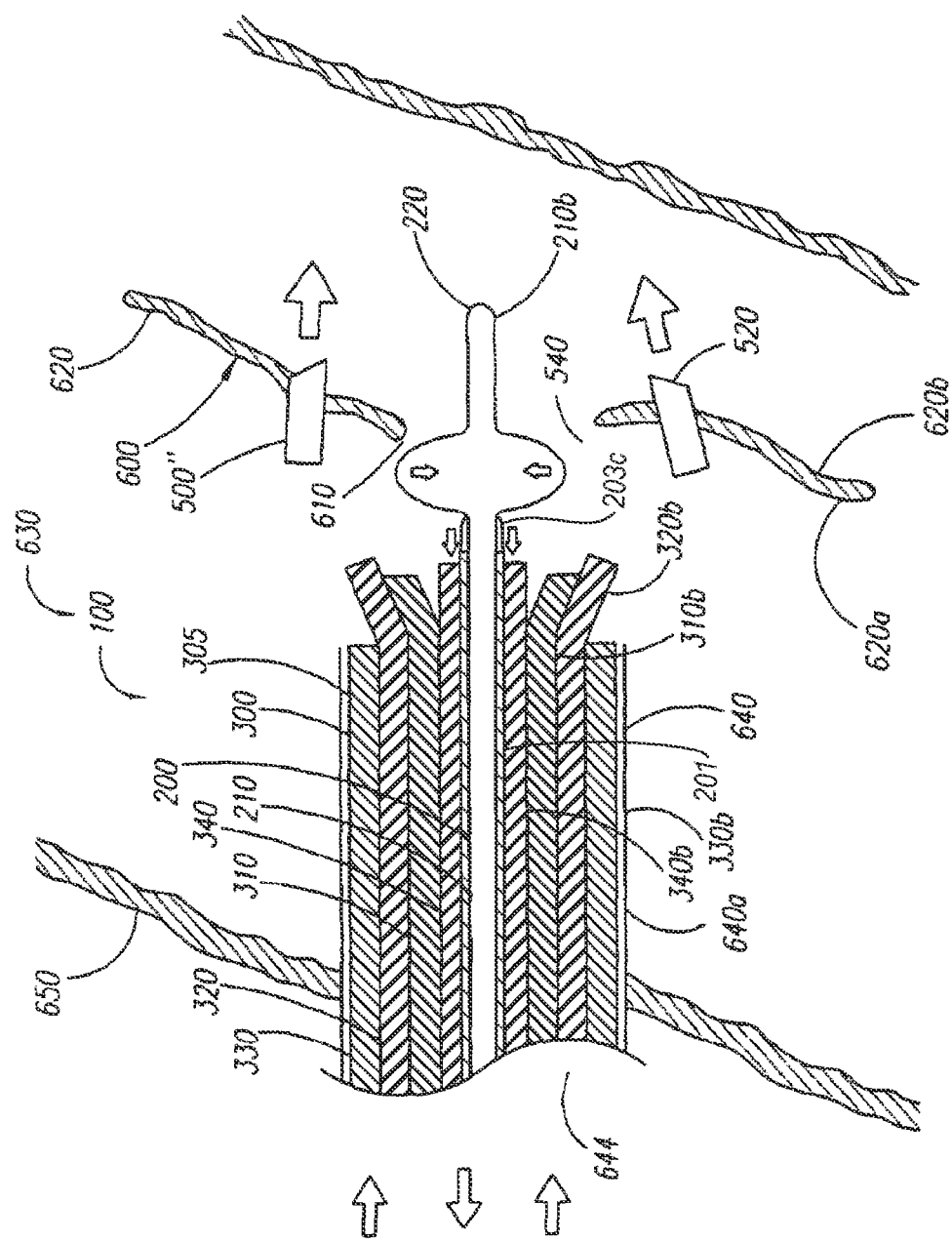
FIG. 8J illustrates the closure element of FIG. 8I upon being deployed and engaging tissue adjacent to the opening in the blood vessel wall.

Upon being directed over the distally-increasing cross-section of the distal end region 310b by the pusher member 320, the substantially tubular closure element 500" can be distally deployed as illustrated in FIG. 8J. When the substantially tubular closure element 500" is deployed, the tines 520 can pierce and otherwise engage significant amount of the blood vessel wall 620 and/or tissue 630 adjacent to the opening 610. For example, the tines 520 can engage a significant amount of the blood vessel wall 620 and/or tissue 630 because the cross-section 530' of the substantially tubular closure element 500" is expanded beyond natural cross-section 530 of the closure element 500 during deployment.

As the closure element is being deployed from the space 360, the locator 220 and hemostasis member 203c also retract proximally and the locator release system 490 (shown in FIG. 4D) and hemostasis release system (not shown) can be activated to transition the locator 220 and hemostasis member 203c from the expanded state to the unexpanded state as the substantially tubular closure element 500" is deployed as shown in FIG. 8J. The locator 220 and hemostasis member 203c each retracts proximally and transitions from the expanded state to the unexpanded state substantially simultaneously with the deployment of the substantially tubular closure element 500". As desired, the locator 220 may be configured to draw the blood vessel wall 620 and/or tissue 630 adjacent to the opening 610 proximally and into the channel 540 defined by the substantially tubular closure element 500". The tines 520 of the substantially tubular closure element 500" thereby can pierce and otherwise engage the drawn blood vessel wall 620 and/or tissue 630. Since the cross-section 530' of the substantially tubular closure element 500" is expanded beyond natural cross-section 530 of the closure element 500, a significant amount of the blood vessel wall 620 and/or tissue 630 can be drawn into the channel 540 and engaged by the tines 520.

Figure 8K:
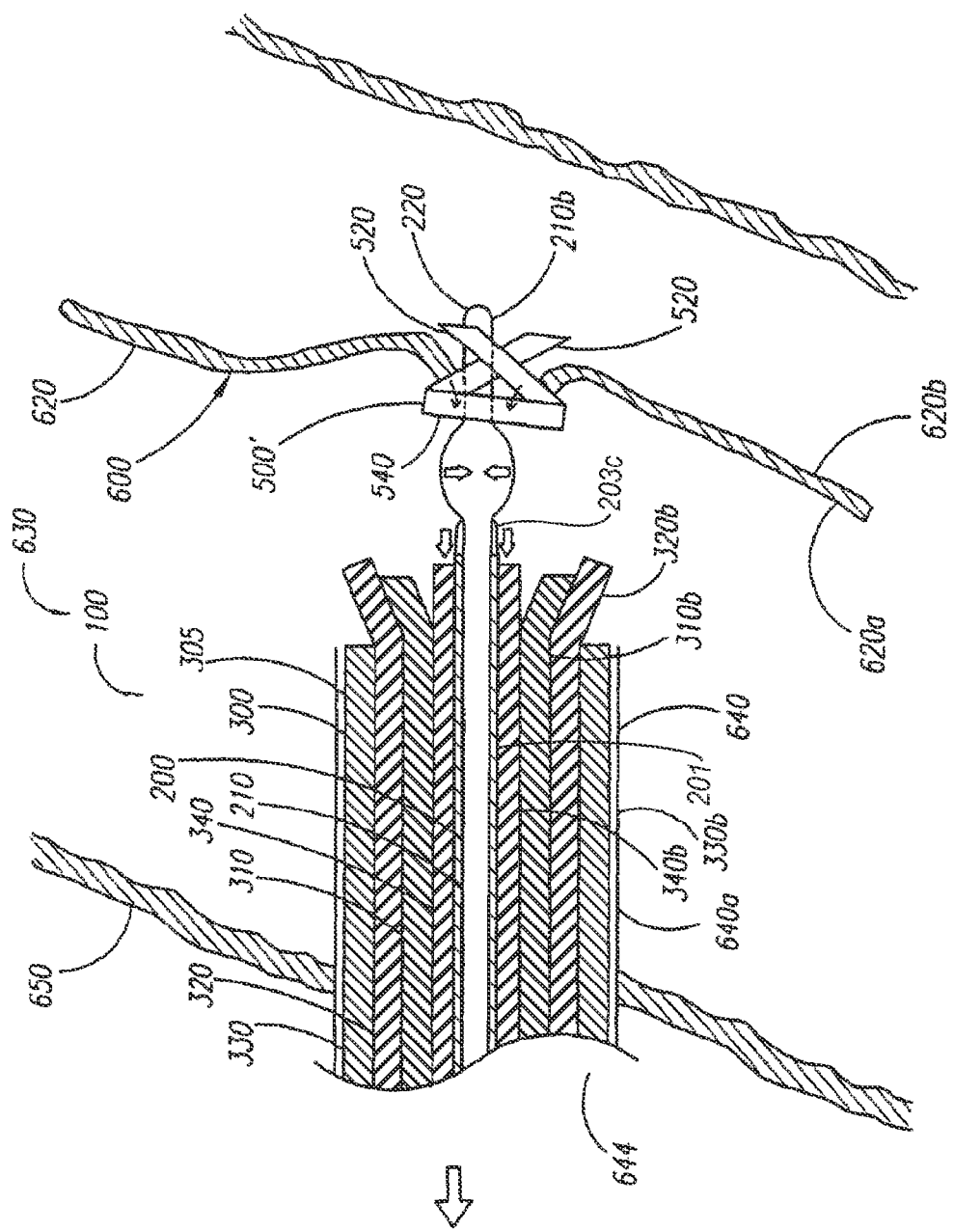
FIG. 8K illustrates the closure element of FIG. 8J transitioning from the substantially tubular configuration to the natural, planar configuration while engaging the engaged tissue.
Figure 8L:
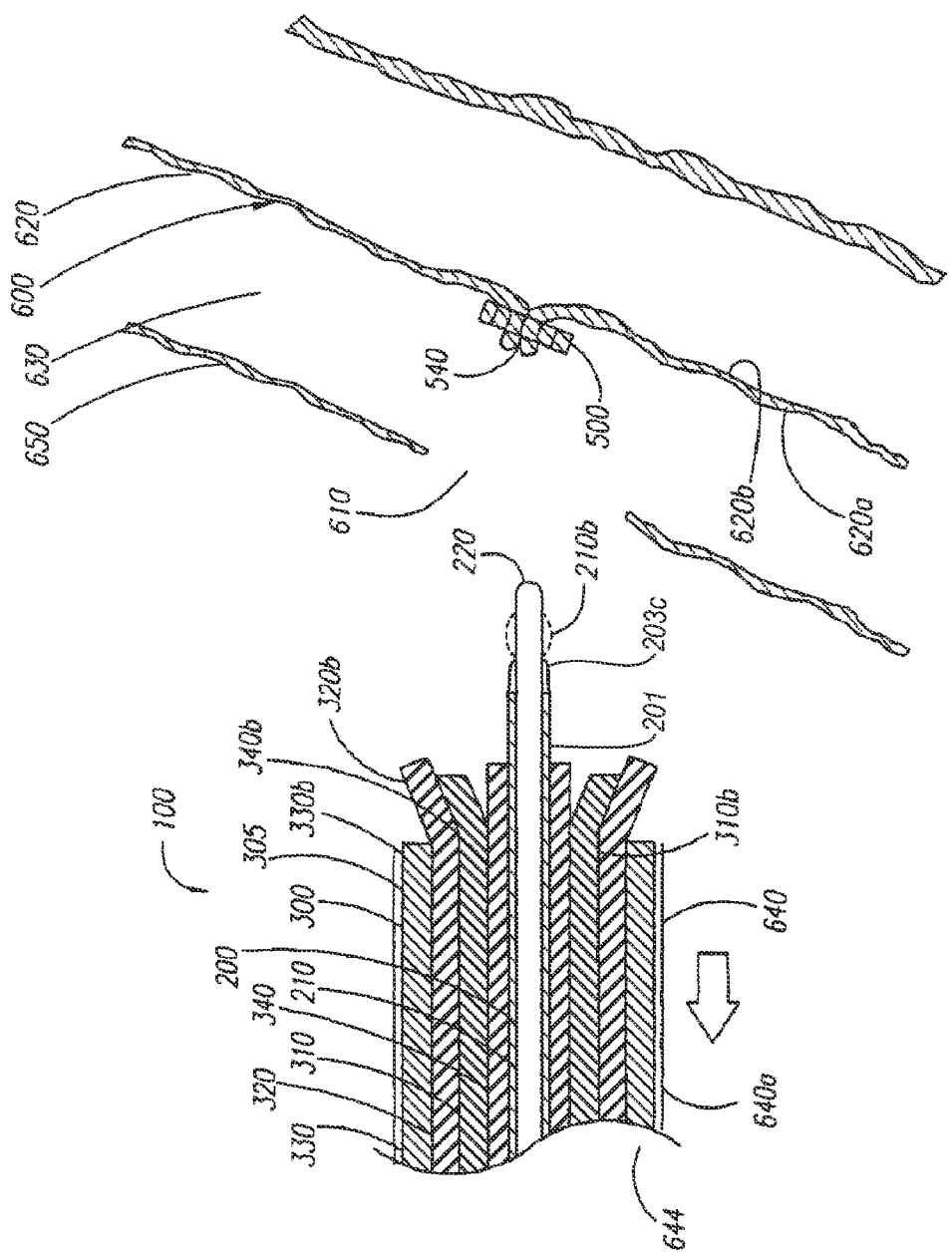
FIG. 8L illustrates the closure element of FIG. 8K drawing the engaged tissue substantially closed and/or sealed.

Turning to FIG. 8K, the substantially tubular closure element 500', once deployed, can begin to transition from the tubular configuration, returning to the natural, planar configuration with opposing tines 520 and a natural cross-section 530 of the closure element 500. As shown, the substantially tubular closure element 500" substantially uniformly transitions from the tubular configuration to the natural, planar configuration. Rotating axially inwardly to form the opposing tines 520 of the closure element 500, the tines 520 draw the tissue 630 into the channel 540 as the substantially tubular closure element 500" forms the closure element 500. Also, the tissue 630 can be drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500 as illustrated in FIG. 8L.

During the process of FIG. 8M, an alternative process can provide for the locator 220 being released so that the ties 520 can grab the locator 220 and pull it against the blood vessel 620. As such, the locator 220 can provide for improved hemostasis upon deployment of the closure element 500.

It will be appreciated that the closure element 500 may be constructed of other materials, that it may include alternative shapes, and that it may adopt alternative methods of operation such that the closure element 500 achieves closure of openings in blood vessel walls or other body tissue. In an additional non-limiting example, the closure element 500 is constructed of materials that use a magnetic force to couple a pair of securing elements in order to close an opening in the lumen wall or tissue. In this alternative embodiment, the closure element 500 may be of a unitary or multi-component construction having a first securing element positionable at a first position adjacent the opening, and a second securing element positionable at a second position adjacent the opening. The first and second securing elements can be provided having a magnetic force biasing the first and second securing elements together, thereby closing the opening, or they are provided having a magnetic force biasing both the first and second securing elements toward a third securing element positioned in a manner to cause closure of the opening. The magnetic closure element 500 may be provided without tines 520, provided the magnetic force coupling the closure elements is sufficient to close the opening. Alternatively, the closure element 500 may be provided with a combination of the magnetic securing elements and tines 520 to provide a combination of coupling forces. Those skilled in the art will recognize that other and further materials, methods, and combinations may be utilized to construct the closure element 500 to achieve the objectives described and implied herein.

F. Housing and Introducer

Figure 9:
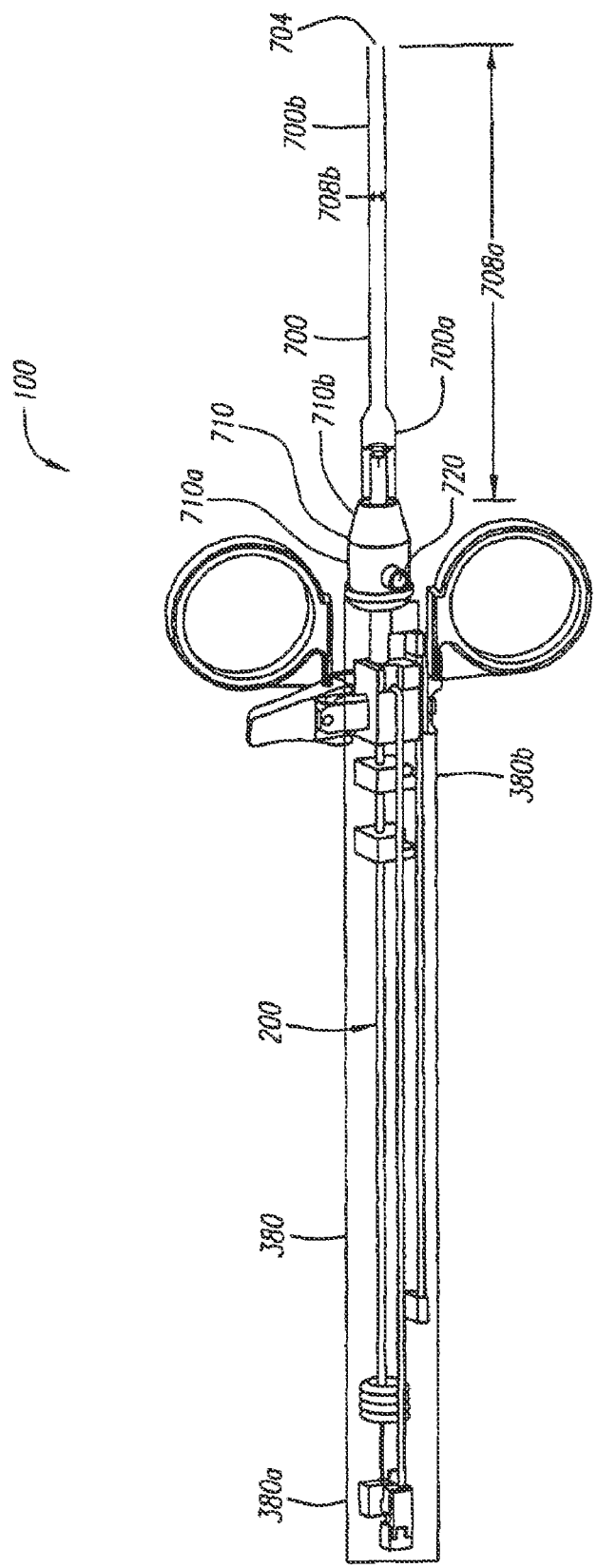
FIG. 9 illustrates one embodiment of an introducer sheath for the apparatus of FIG. 1.

It will be appreciated that the distal end region 380b of the housing 380 can be configured to couple with an introducer sheath 700 as shown in FIG. 9. The introducer sheath 700 can include a substantially flexible or semi-rigid tubular member. Also, the introducer sheath 700 can have a proximal end region 700a and a distal end region 700b and includes a predetermined length and a predetermined cross-section, both of which can be of any suitable dimension. The distal end region 700b can be configured to facilitate insertion of the introducer sheath 700 through tissue and/or into the opening 610 (shown in FIG. 8A) formed in and/or adjacent to the wall 620 (shown in FIG. 8A) of the blood vessel 600 (shown in FIG. 8A) or other body lumen. For example, the distal end region 430b can have a tapered tip (not shown) for facilitating substantially atraumatic introduction of the introducer sheath 700 through a passage formed in the tissue 630 and/or at least partially into the blood vessel wall 620, which is accessible via the passage.

The introducer sheath 700 can also form a lumen 704 that extends along a longitudinal axis of the introducer sheath 700 and substantially between the proximal and distal end regions 700a, 700b. The lumen 704 can have any suitable length 708a and internal cross-section 708b and is configured to slidably receive the tubular body 210 of the locator assembly 200 (shown in FIG. 4A) and/or the tube set 305 of the carrier assembly 300 (shown in FIG. 4A). Since the internal cross-section 708b of the introducer sheath 700 typically can be less than or substantially equal to the predetermined cross-section 338b of the cover member 330, the introducer sheath 700 may be configured to radially expand, such as by stretching, to receive the tube set 305. Alternatively, or in addition, the introducer sheath 700 can be advantageously configured to split as the tube set 305 is received by, and advances within, the lumen 704 of the introducer sheath 700 in the manner described in more detail above with reference to the sheath 640 (shown in FIG. 8A). To facilitate the splitting, the introducer sheath 700 can include one or more splits (not shown), such as longitudinal splits, each split being provided in the manner known in the art. Each split is configured to split the introducer sheath 700 in accordance with a predetermined pattern, such as in a spiral pattern. It will be appreciated that, when the internal cross-section 708b of the introducer sheath 700 is greater than the predetermined cross-section 338b of the cover member 330, it may not be necessary for the introducer sheath 700 to be configured to radially expand and/or split.

The introducer sheath 700 can be coupled with the housing 380 via one or more cooperating connectors (not shown) such that the lumen 704 is substantially axially aligned with the tubular body 210 of the locator assembly 200 and/or the tube set 305 of the carrier assembly 300 and, as desired, may be removably and/or substantially permanently coupled with the housing 380. For example, a hub assembly 710 can be coupled with the proximal end region 700a of the introducer sheath 700. The proximal end region 700a of the introducer sheath 700 can be coupled with, or otherwise provided on, a distal end region 710b of the hub assembly 710, such as via an adhesive, one or more cooperating connectors, and/or a thermo-mechanical joint.

The hub assembly 710 can also include a proximal end region 710a, which provides the one or more mating connectors for coupling the introducer sheath 700 with the housing 380 and forms a lumen (not shown), which extends substantially between the proximal end region 710a and the distal end region 710b. The lumen of the hub assembly 710 can have an internal cross-section or size that is greater than the internal cross-section or size of the lumen 704 of the introducer sheath 700. When the proximal end region 710a of the lumen 704 is properly connected with the hub assembly 710, the lumen of the hub assembly 710 can be configured to communicate with the lumen 704 of the introducer sheath 700. As desired, the proximal end region 700a of the introducer sheath 700 may be flared to facilitate the connection between the introducer sheath 700 and the hub assembly 710.

When properly assembled, the hub assembly 710 can be substantially fluid tight such that the one or more devices can be inserted into the lumen 704 of the introducer sheath 700 without fluid passing proximally through the lumen 704. The hub assembly 710 can be made to be watertight, such as via one or more seals (not shown) and/or valves (not shown) in the manner known in the art. For example, the hub assembly 710 can include a thrust washer and/or valve, a guide for directing the devices into the lumen 704 of the introducer sheath 700, and/or a seal (collectively not shown). The various seals and/or guides can be coupled with the hub assembly 710 via, for example, one or more spacers and/or end caps (also collectively not shown).

As desired, the hub assembly 710 further can include one or more side ports 720. The side ports 720 can communicate with the lumen of the hub assembly 710 and/or the lumen 704 of the introducer sheath 700. At least one of the side ports 720 can be configured to be connected with, and to communicate with, tubing (not shown) to, for example, infuse fluids into the lumen 704 and through the introducer sheath 700. Alternatively, or in addition, at least one of the side ports 720 can provide a "bleed back" indicator, such as in the manner disclosed in the co-pending application Ser. No. 09/680,837. The disclosures of this reference and any others cited therein are expressly incorporated herein by reference.

II. Second Clip Applier

Another alternative embodiment of a clip applier for sealing openings through tissue is shown in FIGS. 10-15. The embodiment of FIGS. 10-15, as described below, has many identical or similar structures that perform identical or similar functions to the embodiments described above and in reference to the preceding Figures. Accordingly, the description below should be considered in view of the descriptions above of the preceding embodiments. Furthermore, those of ordinary skill in the art will appreciate that one or more of the components and/or features of the embodiment shown in FIGS. 10-15 may also be incorporated in the previously described embodiments, as those components and/or features of the previously described embodiments may optionally be incorporated in the embodiment described below and in reference to FIGS. 10-15. In the description of the alternative embodiment below, and in FIGS. 10-15, components of the apparatus that are identical or substantially correspond to those previously described will bear the same reference numerals identified above with the addition of the prime (') identifier.

A. Locator Assembly

Turning to FIGS. 10A-B and 11A-B, the locator and hemostasis assembly 200' can be substantially similar to the structure described above in reference to FIGS. 2A-2D, including a flexible or semi-rigid tubular body 210' (such as an elongate rail) with a longitudinal axis. The tubular body 210' can have a proximal end region 210a' and a distal end region 210b' and includes a predetermined length and a predetermined outer cross-section, both of which can be of any suitable dimension. The distal end region 210b' of the locator assembly 200' can include a substantially rounded, soft, and/or flexible distal end or locator 220' to facilitate atraumatic advancement and/or refraction of the distal end region 210b' into the blood vessel 600. As desired, a pigtail (not shown) may be provided on the distal end 220' to further aid atraumatic advancement of the distal end region 210b'. Additionally, the distal end region 210b' can include a selectively expandable hemostasis member 203' (shows as expanded) as described herein.

The distal end region 210b' of the locator assembly 200' can be selectably controllable between an unexpanded state and an expanded state, in the manner described above in relation to FIGS. 2A-2D. This includes the locator 220' and/or hemostasis member 203' being selectively expanded/unexpanded. In the alternative embodiment shown in FIGS. 10A-10B, the locator 220' and hemostasis member 203' are shown in its expanded state, wherein the substantially flexible members 230' of the expansion elements 230' are flexed outward.

A control member 250', such as a rod, wire, or other elongate member, can be moveably disposed within a lumen (not shown) formed by the tubular body 210' and extending substantially between the proximal end region 210a' and the distal end region 210b'. The control member 250' can have a proximal end region 250a' that is coupled with a control block 260', and a distal end region that is coupled with the distal end region 210b' of the locator assembly 200', the expansion elements 230', and/or the movable end regions 230c' of the substantially flexible expansion members 230'. The control block 260' can be a tubular shape and formed of a metal or rigid plastic, and is adapted to be retained in a control block cavity 265' (see FIG. 10B) formed on the internal surface of the housing bottom half 380d', to thereby maintain the control block 260' in a substantially fixed position relative to the housing 380'. The locator control system can selectively transition the distal end region 210b', the expansion elements 230', and/or the substantially flexible members 230' between the unexpanded and expanded states by moving the tubular body 210' axially relative to the control member 250'. The control system can similarly operate with the hemostasis block 205' so as to control the expansion/retraction of the hemostasis member 203'.

Formed on the proximal end 210a' of the tubular body 210' can have a tubular body block 270' having a proximal groove 271'. The tubular body block 270' can be formed of metal, rigid plastic, or other substantially rigid material and is sometimes formed integrally with or attached securely to the tubular body 210'. The proximal groove 271' and the proximal end of the tubular body block 270' can have a shape adapted to cooperate with a pair of tabs 281a'-b' formed on a locator assembly block 280' whereby the tubular body block 270' is maintained in a fixed axial relationship with the locator assembly block 280'. In this way, the tubular body block 270' and tubular body 210' can be advanced distally by distal advancement of the locator assembly block 280'.

A locator assembly spring 290' can be located coaxially with and substantially surrounds a portion of the tubular body block 270'. The locator assembly spring 290' can be located between and contacts the distal side of two of the tabs 281a formed on the locator assembly block 280', and the proximal side of a locator assembly spring stop 381' formed on the inner surface of the housing bottom half 380d' (see FIG. 10B). The locator assembly spring 290' so located can provide a force biasing the locator assembly block 280' in the proximal direction relative to the housing 380'.

The locator assembly block 280' can be formed of metal, plastic, or other rigid material. A function of the locator assembly block 280' can allow the user to apply a force causing distal movement of the tubular body 210' relative to the control member 250' to cause the locator 220' and/or hemostasis member 203' to transition from the unexpanded state to the expanded state. The proximal end of the locator assembly block 280' can have a slot 281' formed therein, the slot 281' can have a size sufficient to accommodate the control block 260' and the control block cavity 265', and to allow the locator assembly block 280' to travel axially relative to the housing 380'. The distal end of the locator assembly block 280' can have a pair of distally extending forks 282a-b, with each of the forks 282a-b having a ramp 283a-b on its inward facing surface. Finally, the locator assembly block 280' can have a pair of distally extending release tabs 284a-b, with each of the release tabs 284a-b having a detent 285a-b.

As shown in FIG. 11A-11B, the locator assembly block 280' can be slidably received and retained within grooves formed in the proximal end of the housing 380', with the proximal end of the locator assembly block extending from the proximal end of the housing. The control block 260' and control block cavity 265' can be located in the slot 281' formed in the proximal end of the locator assembly block 280'.

Figure 10A:
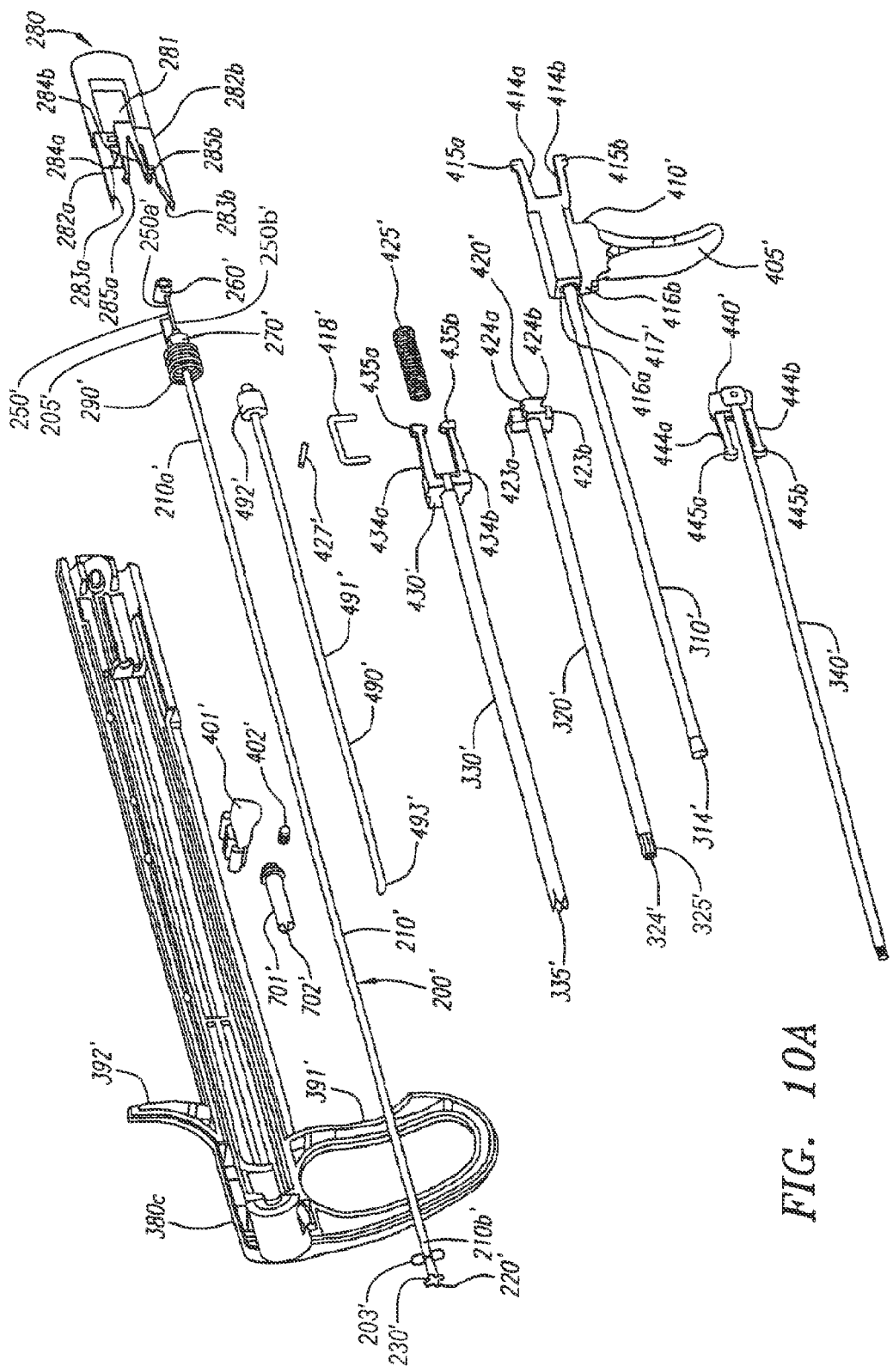
FIG. 10A illustrates an assembly view of the components included in an alternative embodiment of the apparatus for closing openings formed in blood vessel walls.
Figure 10B:
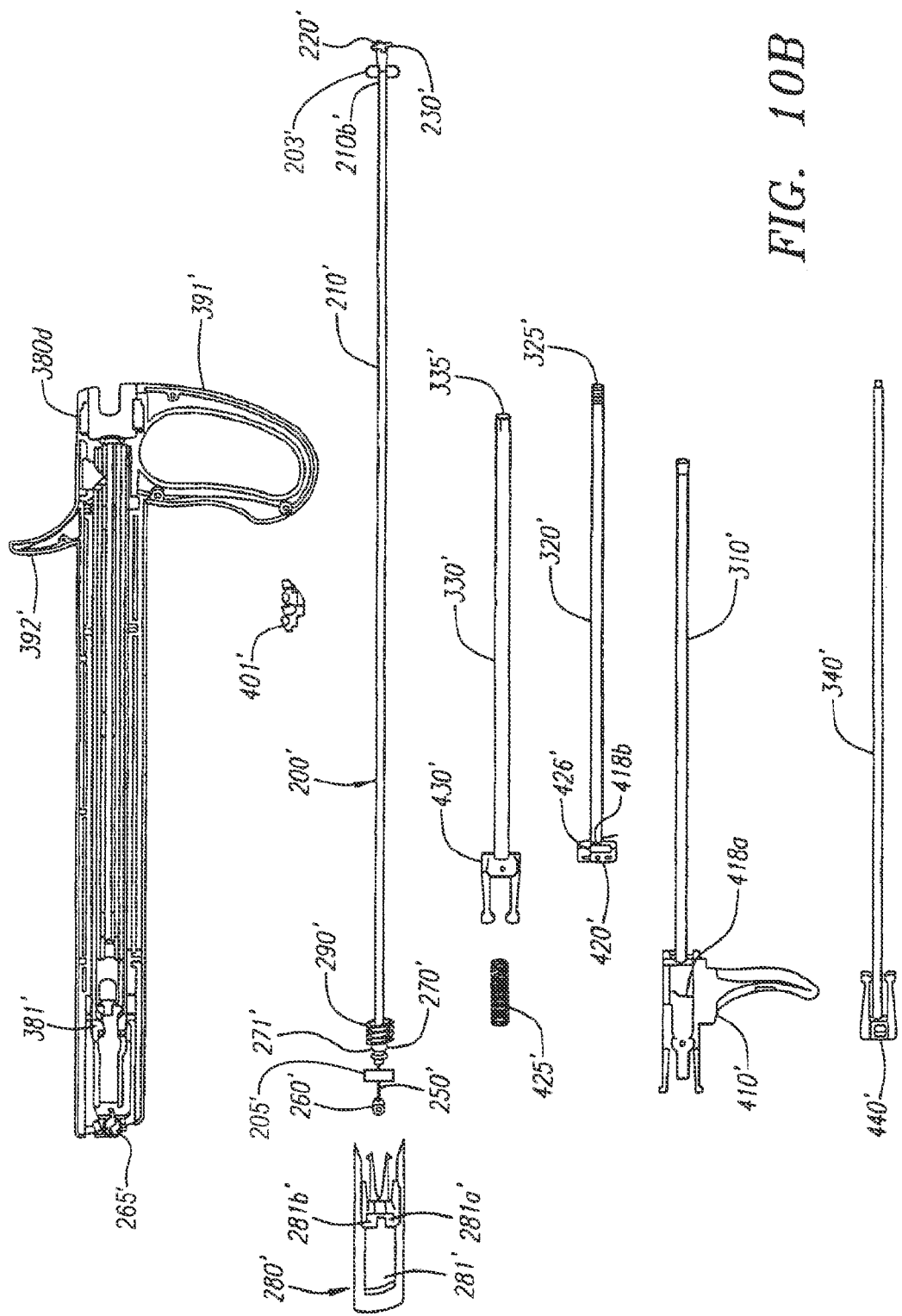
FIG. 10B illustrates an assembly view of the components shown in FIG. 10A, showing the reverse view of that shown in FIG. 10A.
Figure 15:
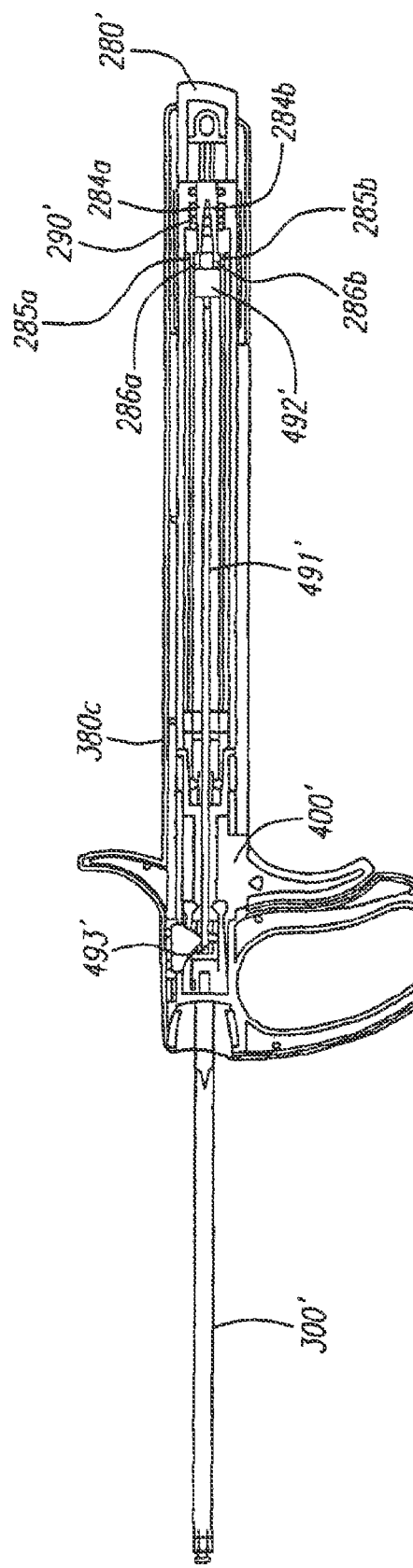
FIG. 15 illustrates a reverse view of the apparatus of FIG. 11-14D, showing the locator release system.

The locator release system 490' can perform the function of releasing the locator assembly 200', thereby allowing the locator 220' and/or hemostasis member 203' to transition from an expanded state to an unexpanded state. Alternatively, it can release the locator 220' when configured to be implanted. Turning to FIGS. 10A-10B and FIG. 15, the locator release system 490' of the alternative embodiment of the apparatus can include locator release rod 491' having a release tab spacer block 492' formed on its proximal end. The locator release rod 491' and release tab spacer block 492' can be received and retained in a groove formed on the interior surface of the housing bottom half 380d. The release tab spacer block 492' can be integrally formed with or attached to the proximal end of the locator release rod 491', and is formed of metal, plastic, or other rigid material. As shown in FIG. 15, the release tab spacer block 492' can have a shape and size adapted to fit between the release tabs 284a-b formed on the locator assembly block 280', thereby biasing the release tabs 284a-b outward and causing the outward facing detents 285a-b to engage a pair of retaining grooves 286a-b formed on the interior of the housing 380'. As long as the detents 285a-b are thus engaged with the retaining grooves 286a-b of the housing 380', the locator assembly block 280' can be held in its axial position against the spring force imparted in the proximal direction by the locator assembly spring 290'. The distal end of the locator release rod 491' can have an engagement member 493' that, in one configuration, includes an inward bend on the distal end of the locator release rod. As described more fully below, the engagement member 493' on the locator release rod 491' can be positioned within the apparatus such that, when the closure element 500 is delivered, the engagement member 493' is engaged and caused to move axially in the distal direction, thereby disengaging the release tab spacer block 492' from the locator assembly block 280' and causing the locator assembly simultaneously to transition from its expanded state to the unexpanded state.

The alternative embodiment of the apparatus 100' can include a carrier assembly 300' that is coupled with, and slidable relative to, the locator assembly 200'. The carrier assembly 300' can be configured to receive and retain the closure element 500 (shown in FIGS. 6A-6B), which can be disposed substantially within the carrier assembly 300'. When the locator assembly 200' engages the inner surface 620b (shown in FIG. 8A) of the blood vessel wall 620 (shown in FIG. 8A), the carrier assembly 300' can be further configured to position the closure element 500 substantially adjacent to the opening 610 and to deploy the closure element 500, as described elsewhere herein.

B. Tube Set

Turning to FIGS. 10A-10B, the carrier assembly 300' can include a tube set can include a carrier member 310', a pusher member 320', a cover member 330', and a support member 340'. The carrier member 310', pusher member 320', cover member 330', and support member 340' can be provided as a plurality of nested, telescoping members with a common longitudinal axis. The carrier member 310' can be configured to receive and support the closure element 500. While being disposed on the carrier member 310', the closure element 500 can be deformed from the natural, planar configuration to form the substantially tubular closure element 500" (shown in FIGS. 6F-6G) as described herein. As before, the support member 340' can be configured to include the hemostasis member 203.

The carrier member 310' can include a proximal end region 310a' and a distal end region 310b'. The carrier member 310' can also define a lumen 314' that extends substantially between the proximal end region 310a' and the distal end region 310b' and that is configured to slidably receive at least a portion of the tubular body 210' of the locator assembly 200' and/or the support member 340'. Although the exterior cross-section of the carrier member 310' is substantially uniform, the distal end region 310b' of the carrier member 310' can have a cross-section that increases distally, as illustrated in FIGS. 10A-B, for substantially uniformly expanding the substantially tubular closure element 500" beyond the natural cross-section 530 of the closure element 500 when the substantially tubular closure element 500" is deployed. Alternatively, the distal end region 310b' may be formed with a uniform cross-section to deploy the closure element 500 without cross-sectional expansion.

The pusher member 320' can have a proximal end region 320a' and a distal end region 320b' and is coupled with, and slidable relative to, the carrier member 310'. The pusher member 320' can include a predetermined length and a predetermined cross-section, both of which can be of any suitable dimension and can be configured to slidably receive the carrier member 310' such that the distal end region 320b' of the pusher member 320' is offset proximally from the distal end region 310b' of the carrier member 310'. As desired, the predetermined length of the pusher member 320' can be greater than or substantially equal to the predetermined length of the carrier member 310'. The predetermined length of the pusher member 320' can be less than the predetermined length of the carrier member 310' such that the carrier member 310' and the pusher member 320' at least partially define a space 360' distal to the distal end region 320b' of the pusher member 320' and along the periphery of the carrier member 310'.

The pusher member 320' can be substantially tubular and can define a lumen 324' that extends substantially between the proximal end region 320a' and the distal end region 320b' and that is configured to slidably receive at least a portion of the carrier member 310'. The cross-section of the pusher member 320' can be substantially uniform, and the distal end region 320b' of the pusher member 320' can include one or more longitudinal extensions 325', which extend distally from the pusher member 320' and along the periphery of the carrier member 310'. The longitudinal extensions 325' can be biased such that the longitudinal extensions 325' extend generally in parallel with the common longitudinal axis of the carrier assembly tube set. The longitudinal extensions 325' can be sufficiently flexible to expand radially, and yet sufficiently rigid to inhibit buckling, as the distal end region 320b' is directed distally along the carrier member 310' and engage the distally-increasing cross-section of the distal end region 310b' of the carrier member 310' to deploy the substantially tubular closure element 500".

The cover member 330' can be configured to retain the substantially tubular closure element 500" substantially within the carrier assembly 300' prior to deployment. Being coupled with, and slidable relative to, the pusher member 320', the cover member 330' can have a proximal end region 330a' and a distal end region 330b' and includes a predetermined length and a predetermined cross-section, both of which can be of any suitable dimension. When formed as a substantially rigid, semi-rigid, or flexible tubular member, the cover member 330' can have an inner periphery and an outer periphery and can define a lumen 334'. The lumen 334' can extend substantially between the proximal and distal end regions 330a', 330b' of the cover member 330' and can be configured to slidably receive at least a portion of the pusher member 320'. When the cover member 330' is properly positioned within the carrier assembly 300', the distal end region 330b' can be configured to extend over the space 360', thereby defining an annular cavity 370' for receiving and retaining the substantially tubular closure element 500".

The cross-section of the cover member 330' can be substantially uniform, and the distal end region 330b' of the cover member 330' can include one or more longitudinal extensions 335', which extend distally from the cover member 330' and along an outer periphery of the pusher member 320' (see FIG. 3D). Although the longitudinal extensions 335' can extend generally in parallel with common longitudinal axis 350', the longitudinal extensions 335' can be biased such that the plurality of longitudinal extensions 335' extend substantially radially inwardly as illustrated in FIGS. 3A and 3D. Thereby, the longitudinal extensions 335' can at least partially close the lumen 334' substantially adjacent to the distal end region 330b' of the cover member 330'. To permit the substantially tubular closure element 500" to be deployed from the annular cavity 370', the longitudinal extensions 335' can be sufficiently flexible to expand radially to permit the distal end region 310b' of the carrier member 310' to move distally past the cover member 330' to open the annular cavity 370' such that the distal end region 330b' no longer extends over the space 360'.

If the carrier assembly 300' is assembled as the plurality of nested, telescoping members as shown in FIG. 3A, the carrier member 310' can be at least partially disposed within, and slidable relative to, the lumen 324' of the pusher member 320'.

The support member 340' can be slidable relative to the pusher member 310'. The pusher member 320', in turn, can be at least partially disposed within, and slidable relative to, the lumen 334' of the cover member 330'. To couple the carrier assembly 300' with the locator assembly 200', the tubular body 210' of the locator assembly 200' can be at least partially disposed within, and slidable relative to, the lumen 314' of the carrier member 310'. The longitudinal axis of the locator assembly 200' can be substantially in axial alignment with the common longitudinal axis of the carrier member 310', the pusher member 320', and the cover member 330'.

The tube set 305 can also include a support member 340' as shown in FIGS. 10A-B. The support member 340' can be configured to slidably receive the tubular body 210' of the locator assembly 200' and to provide radial support for the distal end region 210b' of the tubular body 210' when the locator assembly 200' is coupled with the carrier assembly 300'. The carrier assembly 300' can advantageously include the support member 340', for example, if the tubular body 210' is not sufficiently rigid or under other circumstances in which support for the tubular body 210' might be desirable. It also will be appreciated that the support member 340' also can be configured to inhibit the plurality of longitudinal extensions 335', which extend from the distal end region 330b' of the cover member 330', from expanding prematurely when the closure element 500 is deployed. If the longitudinal extensions 335' were to expand prematurely, they may become hung up on the introducer sheath 640 or other delivery member (in an introducer sheath or delivery member is used), the tissue 630, or the wall 620 of the blood vessel. This may interfere with the proper advancement or other movement of the cover member 330' and the carrier assembly 300'. Also, the support member 340' can include the features of the hemostasis member 203'.

When formed as a substantially rigid, semi-rigid, or flexible tubular member, the support member 340' can include a proximal end region 340a' and a distal end region 340b'. Having an outer periphery, the support member 340' can define a lumen 344' that extends substantially between the proximal end region 340a' and the distal end region 340b' and that is configured to slidably receive and support at least a portion of the tubular body 210' of the locator assembly 200'. The support member 340', in turn, can be at least partially slidably disposed within the lumen 314' of the carrier member 310' such that the tubular body 210' of the locator assembly 200' is coupled with, and slidable relative to, the carrier member 310' in the manner described in more detail above. The support member 340' can have a predetermined length and a predetermined cross-section, both of which can be of any suitable dimension, and the cross-section can be substantially uniform. Although shown and described as being substantially separate for purposes of illustration, it will be appreciated that the carrier member 310', the pusher member 320', the cover member 330', and/or the support member 340' can be provided, in whole or in part, as one or more integrated assemblies.

The carrier assembly 300' also can include a housing 380', the top half 380c of which is illustrated in FIG. 10A, and the bottom half 380d of which is shown in FIG. 10B. When formed as an elongate member with a longitudinal axis, the housing 380' can have an outer periphery and includes a proximal end region 380a' and a distal end region 380b'. Thereby, when the apparatus 100' is properly assembled, the tubular body 210' of the locator assembly 200' can be at least partially disposed within, and slidable relative to, the tube set 305 such that the distal end region 210b' of the tubular body 210' extends beyond the distal end regions 310b', 320b', 330b', and/or 340b'. The tubular body 210', the carrier member 310', the pusher member 320', the cover member 330', and, if provided, the support member 340' can be at least partially disposed within, and slidable relative to, the housing 380', and the respective distal end regions 210b', 310b', 320b', 330b', and 340b' extend from the distal end region 380b' of the housing 380' such that the common longitudinal axis 350' of the tube set 305 is substantially axially aligned with the longitudinal axis 386' of the housing 380'. Being configured to slidably retain the respective proximal end regions 210a', 310a', 320a', 330a', and 340a', the housing 380' can support the tube set 305 and can have one or more handles 391', 392' to facilitate use of the apparatus 100'. The handles 391', 392' can extend substantially radially from the outer periphery of the housing 380' and can be provided in the manner known in the art.

When the apparatus 100' is properly assembled, the tubular body 210' of the locator assembly 200' can be at least partially disposed within, and slidable relative to, the tube set 305 of the carrier assembly 300' such that the distal end region 210b' of the tubular body 210' extends beyond the distal end regions 310b', 320b', 330b', and/or 340b'. Further, the proximal end region 210a' of the tubular body 210' and the proximal end regions 310a', 320a', 330a', and/or 340a' of the tube set 305 can be at least partially disposed within, and slidable relative to, the housing 380'. The switching system of the locator assembly 200' and a switching system of the triggering system 400' can be accessible external to the housing 380' as shown in FIGS. 11-15.

C. Triggering System

As shown in FIGS. 10-15, the triggering system 400' of the alternative embodiment of the apparatus 100' can be disposed substantially within the housing 380'. The triggering system 400' can be configured to control the relative axial movement and/or positioning of the respective distal end regions 310b', 320b', 330b', and 340b' of the tube set 305 and/or the distal end region 210b' of the locator assembly 200'. Axial motion of one or more of the carrier member 310', the pusher member 320', the cover member 330', and the support member 340' and/or the tubular body 210' can be attained, for example, by applying an axial force to the switching system 405".

The triggering system 400' can include a set of block members—a carrier block 410', a pusher block 420', a cover block 430', and a support block 440'—each of which is formed integrally with or securely attached to its respective member of the carrier assembly 300'. The block members can be adapted to selectably couple and decouple the carrier member 310', the pusher member 320', the cover member 330', and the support member 340' relative to one another in order to provide axial movement of those components in a predetermined manner intended to deliver the closure element 500 in the manner described herein. For example, when the carrier assembly 300' reaches a first predetermined distal position, the support member 340' can be decoupled from the carrier member 310', the pusher member 320', and the cover member 330' and is thereafter substantially inhibited from further axial movement. Thereby, the carrier member 310', the pusher member 320', and the cover member 330' may be directed distally as the support member 340' remain substantially stationary. Subsequently, the carrier member 310' and the cover member 330' can be decoupled from the pusher member 320' and thereafter inhibited from further axial movement. Thereby, the pusher member 320' may be directed distally as the support member 340', carrier member 310', and cover member 330' remain substantially stationary, as described more fully herein.

The carrier block 410' can be disposed on the proximal end region 310a' of the carrier member 310' and can include a trigger extension 405' that extends through a slot in the housing 380' to the exterior of the housing 380' to be accessible to the user. The carrier block 410' can include a pair of grooves 413a-b formed on a peripheral surface of the carrier block 410', the grooves 413a-b being adapted to receive and retain a pair of tabs 445a-b formed on a pair of forks 444a-b extending distally from the support block 440', thereby selectably coupling the support block 440' to the carrier block 410'. The carrier block 410' can also include a pair of distal tabs 416a-b extending from the distal end of the carrier block 410', and adapted to engage a pair of slots 423a-b formed on the proximal end of the pusher block 420'.

The carrier block 410' can also include a pair of forks 414a-b extending in the proximal direction from the proximal end of the carrier block, each of the forks having an outward directed tab 415a-b at its proximal end. The tabs 415a-b can be adapted to selectably engage a pair of slots 387a-b (not shown) formed on the interior surface of the housing 380' near its proximal end and, when so engaged, to fix the axial position of the carrier block 410' and, with it, the carrier assembly 300' relative to the housing 380'. The tabs 415a-b can be disengaged from the slots in the housing when the locator assembly block 280' is moved axially in the distal direction in the following manner (see FIG. 11B). As the locator assembly block 280' is advanced distally, the interior surfaces of the ramps 283a-b on the locator assembly block forks 282a-b can engage the exterior surfaces of the tabs 415a-b and cause the carrier block forks 414a-b to flex inward, releasing the tabs 415a-b from the slots in the housing, thereby freeing the carrier block 410' and the carrier assembly 300' to move axially. Thus, axial movement of the carrier block 410' within the apparatus can be inhibited until the locator assembly block 280' is advanced to transition the locator assembly 200' to the expanded condition, simultaneously releasing the tabs 415a-b on the carrier block 410'.

The pusher block 420' can be disposed on the proximal end region 320a' of the pusher member 320'. As described above, the pusher block 420' can include a pair of slots 423a-b formed on its proximal end that are adapted to selectably engage the pair of distal tabs 416a-b extending from the distal end of the carrier block 410'. The pusher block 420' can also include a pair of grooves 424a-b formed on its peripheral surface, the grooves 424a-b being adapted to engage a pair of tabs 435a-b formed on a pair of forks 434a-b extending from the proximal side of the cover block 430' to selectably couple the cover block 430' to the pusher block 420'.

The cover block 430' can be disposed on the proximal end region 330a' of the cover member 330'. As described above, the cover block 430' can include a pair of forks 424a-b extending from the proximal end of the cover block 430', each of the forks having an inward directed tab 435a-b that are adapted to engage the grooves 424a-b on the peripheral surface of the pusher block 420' to selectably couple the cover block 430' to the pusher block 420'.

The support block 440' can be disposed on the proximal end region 340a' of the support member 340'. As described above, the support block 440' can include a pair of forks 444a-b extending from the distal end of the support block 440', each of the forks having an inward directed tab 445a-b that are adapted to engage the grooves 413a-b formed on the surface of the carrier block 410' to selectably couple the support block 440' to the carrier block 410'.

Figure 12:
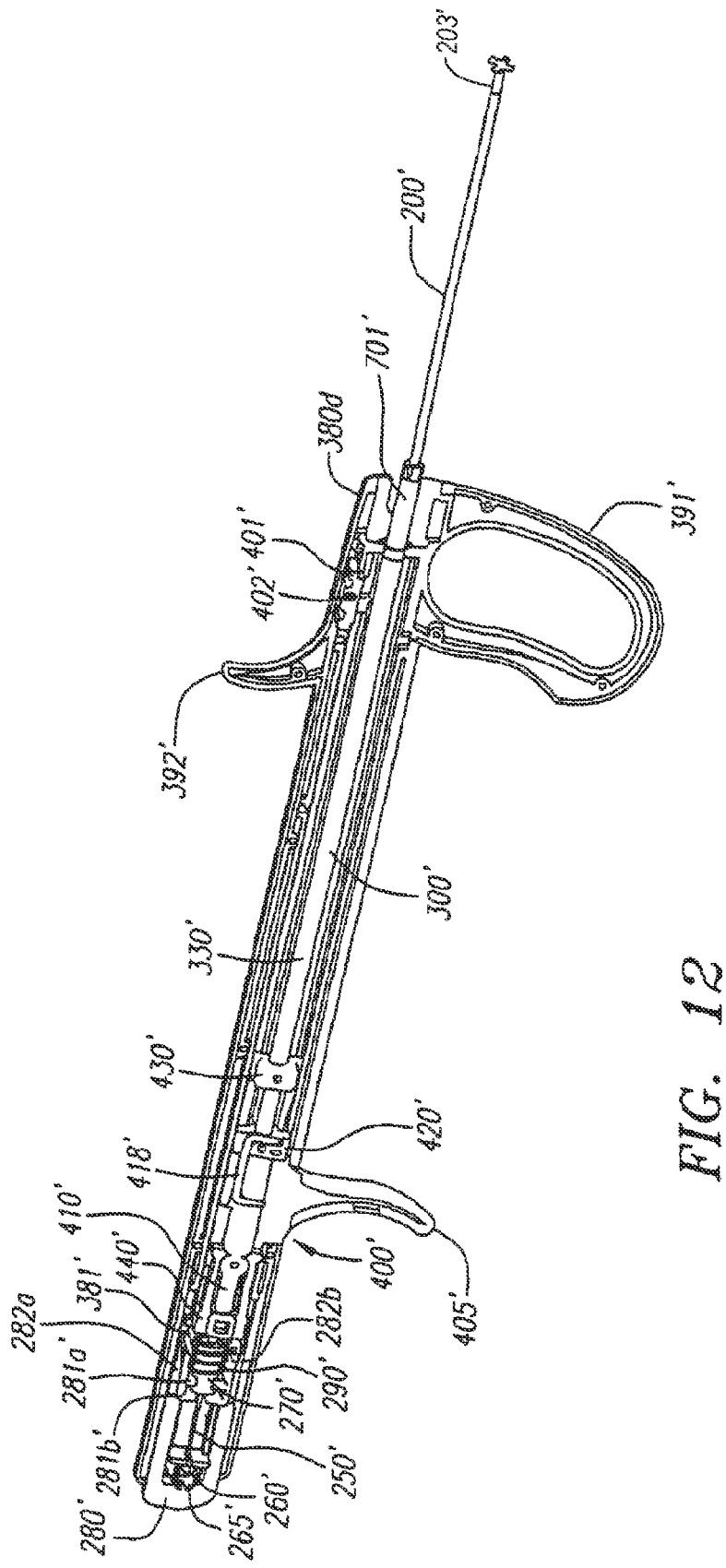
FIG. 12 illustrates the apparatus of FIG. 11A after advancement of the locator assembly block.
Figure 13:
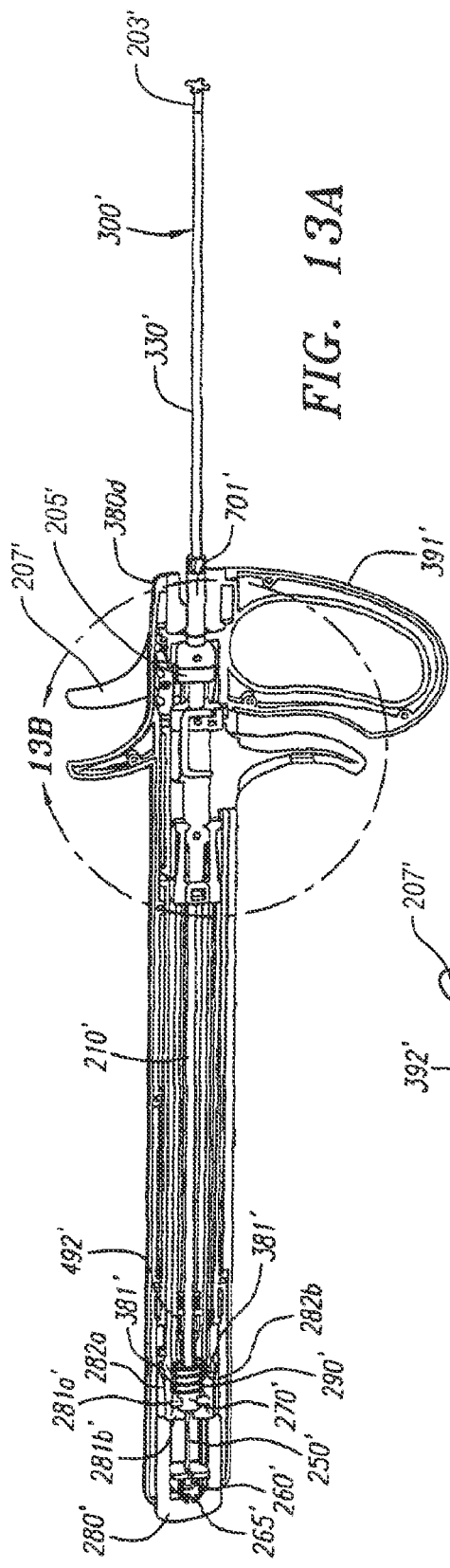
FIG. 13A illustrates the apparatus of FIG. 12 after distal advancement of the triggering system and carrier assembly.
FIG. 13B illustrates a close-up view of the distal end of the housing and internal components of the apparatus shown in FIG. 13A.
Figure 14:
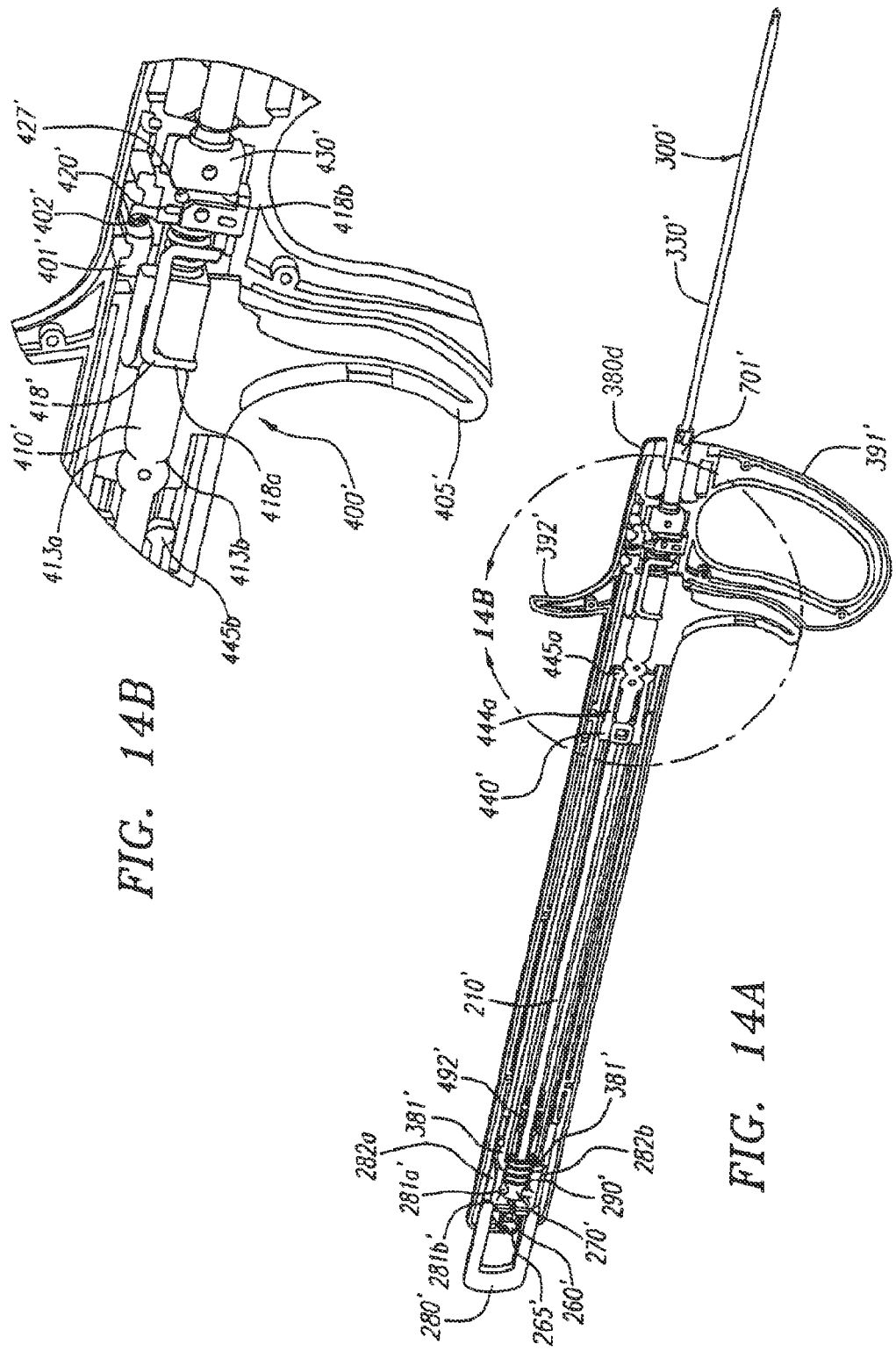
FIG. 14A illustrates the apparatus of FIG. 13 after further distal advancement of the triggering system and carrier assembly.
FIG. 14B illustrates a close-up view of the distal end of the housing and internal components of the apparatus shown in FIG. 14A.

The carrier block 410', pusher block 420', cover block 430', and support block 440' are shown in FIGS. 11-13 in their fully coupled state, with the support block 440' coupled to the carrier block 410', the pusher block 420' coupled to the carrier block 410', and the cover block 430' coupled to the pusher block 420'. In this arrangement, the carrier assembly 300' can include a coaxial set of tubes (as shown, for example, in FIG. 3A), with the support member 340' slidably retained substantially within the carrier member 310', which is in turn slidably retained substantially within the pusher member 320', which is in turn slidably retained substantially within the cover member 330'.

The triggering system 400' of the alternative embodiment of the apparatus can include an energy storing element that is used in the final stage of the closure element 500 delivery process. The energy storing element, such as a spring like the pusher spring 425' shown in FIGS. 10A-10B, can be substantially retained in a spring cavity 417' formed in the carrier block 410' and coaxially surrounds a proximal portion 310a' of the carrier member 310'. The pusher spring 425' can be capable of expanding and contracting, storing potential energy as it is contracted and releasing energy as it expands. In its fully expanded state, the pusher spring 425' can have a length that is greater than the length of the spring cavity 417'. The cross-sectional dimension of the pusher spring 425' can be such that it backs up against and contacts the proximal end of the pusher block 420'. Thus, when the pusher spring 425' is in place between the carrier block 410' and the pusher block 420', the pusher spring 425' can be capable of imparting a force biasing the carrier block 410' away from the pusher block 420'.

Prior to delivery of the closure element 500, the distal end of the carrier block 410' can be in physical contact with the proximal end of the pusher block 420'. In this pre-delivery condition, the pusher spring 425' can be in a contracted state and can be maintained fully within the spring cavity 417' formed in the carrier block 410'. A catch member 418' can serve the function of maintaining the carrier block 410' and pusher block 420' in the pre-delivery condition against the spring force of the pusher spring 425', the force of which would otherwise force apart the carrier block 410' from the pusher block 420'. The catch member 418' can be a U-shaped piece of metal, plastic, or other rigid material that engages a first groove 418a formed on the surface of the carrier block 410' and a second groove 418b formed on the surface of the pusher block 420'. The pusher block 420' can include a hole 426' extending through a portion thereof, with one end of the hole 426' opening into the groove 418b. The hole 426' can be adapted to receive a trip pin 427'. During the closure element deployment process, the trip pin 427' can be advanced through the hole 426', where it can encounter the catch member 418' that is retained in the groove 418b. Further advancement of the trip pin 427' can cause the catch member 418' to become disengaged from the groove 418b, thereby releasing the restraining force on the pusher spring 425'.

The operation of the triggering system 400' of the alternative embodiment of the apparatus 100' is illustrated in FIGS. 11-14 with the closure element 500 (shown in FIGS. 6A-6B) disposed substantially within the apparatus 100'. As shown in FIGS. 11A-11B, the apparatus can have an initial position in which the locator assembly block 280' is extended proximally and the triggering system 400' is in its most proximal position. Accordingly, the locator control system 200' is in its unexpanded state, as shown. At a point in time that the distal end region 210b' of the locator assembly 200', and thereby the hemostasis member 203', has been positioned as desired (for example, within the blood vessel 600), the locator assembly block 280 is depressed distally, as shown in FIG. 12, thereby transitioning the locator assembly to the expanded state and, simultaneously, releasing the triggering system 400' from the initial position (in the manner described above) such that the triggering system can be advanced distally within the housing 380'.

The triggering system 400' can be advanced distally within the housing 380', thereby advancing the tube set 305 into position adjacent the blood vessel. At a first predetermined position, shown in FIG. 13, the support block 440' can encounter a support stop (not shown) on the interior surface of the housing bottom half 380*d* that inhibits the support block 440' from advancing further distally. As a result, an application of additional distal force to the triggering system 400' can cause the support block 440' to decouple from the carrier block 410', as shown in FIG. 13. More specifically, the tabs 445*a-b* on the forks 444*a-b* of the support block 440' can disengage from the grooves 413*a-b* on the carrier block 410'. Thus, the support block 440' can remain in the position shown in FIG. 13, while the carrier block 410' is able to advance further distally upon application of force to the triggering system 400'.

Turning to FIGS. 14A-14B, as the triggering system 400' can be advanced further distally, the cover block 430' engages a cover stop on the interior surface near the distal end of the housing 380', thereby inhibiting additional distal advancement of the cover block 430'. In addition, the trigger extension 405' can engage the handle 391' on the exterior of the apparatus, thereby inhibiting additional distal advancement of the carrier block 410'. At this point, the distal end of the tube set corresponds generally to the state illustrated in FIG. 8G, prior to deployment of the closure element 500.

The closure element 500 can be deployed by releasing the pusher spring 425', which causes the pusher block 420' (and, thus, the pusher member 320') to advance distally, deploying the closure element in the manner described above. The pusher spring 425' can be released by disengaging the catch member 418' from the groove 418*b* on the pusher block 420', thereby releasing the pusher spring 425' to force the pusher block 420' and, thus, the pusher member 320'—distally relative to the carrier block 410'. This action can cause the pusher member 320' to deploy the closure element 500, as shown, for example, in FIGS. 8H-8L. The catch member 418' can be disengaged from the groove 418*b* by applying a force to the trigger 401', which, in the deployment position, is aligned with the trip pin 427' retained in the pusher block 420'. A trigger spring 402' can bias the trigger outward relative to the housing 380'. The user can apply an inward directed force to the trigger 401' to counteract the biasing force of the trigger spring 402' and force the trigger 401' against the trip pin 427'.

In addition to deploying the closure element 500, the distal advancement of the pusher block 420' can also cause the locator release system 490' to activate, thereby transitioning the locator 220' and/or hemostasis member 203' from the expanded state to the unexpanded state. As the pusher block 420' advances distally to deploy the closure element 500' in the manner described above, the pusher block 420' can also engage the engagement member 493' of the locator release system 490' and advances the locator release rod 491' distally. This action can cause the release tab spacer block 492' to disengage from the release tabs 284*a-b* on the locator assembly block 280' (see FIG. 15), thereby releasing the locator assembly block 280', which returns to its proximal position, causing the locator 220' and/or hemostasis member 203' to return to the unexpanded state.

D. Delivering Closure Element

The closure element 500 deployment and locator 220 and hemostasis member 203 release actions can occur nearly simultaneously, as illustrated in FIGS. 8I-8M. As described previously, the apparatus 100 can be brought into contact with the blood vessel 600 by inserting and advancing the distal end of the apparatus through an introducer sheath 640 to the blood vessel location. The use of an introducer sheath 640 is optional, as the apparatus can be used to deploy the closure element 500 without the use of an introducer sheath 640. Furthermore, as describe above, when an introducer sheath 640 is used, the locator assembly 200, 200', hemostasis tube 201, and the carrier assembly 300, 300' may have cross-sectional dimensions that allow them to be received within the introducer sheath 640 either without causing radial expansion or splitting of the sheath, or with causing radial expansion or splitting of the sheath. If the relative cross-sectional dimensions of the introducer sheath 640 and carrier assembly 300, 300' are such that the introducer sheath 640 is intended to be split during advancement of the carrier assembly 300, 200', a sheath cutter 701' having a pointed tip 702' may be utilized to initiate a split at the proximal end of the introducer sheath 640. The sheath cutter 701' can be advantageously placed coaxially over the cover member 330' and can be attached to the distal end of the housing 380' (FIGS. 11A-11B), whereby it will initiate a split in the introducer sheath 640. Distal advancement of the carrier assembly 300, 300' causes the initial split at the proximal end of the sheath to advance as the carrier assembly 300, 300' advances, as will be understood by those skilled in the art.

III. Third Clip Applier

Another alternative embodiment of a clip applier for sealing openings through tissue is shown in FIGS. 16-19. The embodiment of FIGS. 16-19, as described below, has many identical or similar structures that perform identical or similar functions to the embodiments described above and in reference to the preceding Figures. Accordingly, the description below should be considered in view of the descriptions above of the preceding embodiments. Furthermore, those of ordinary skill in the art will appreciate that one or more of the components and/or features of the embodiment shown in FIGS. 16-19 may also be incorporated in the previously described embodiments, as those components and/or features of the previously described embodiments may optionally be incorporated in the embodiment described below and in reference to FIGS. 16-19.

A. Locator Assembly

Figure 16:
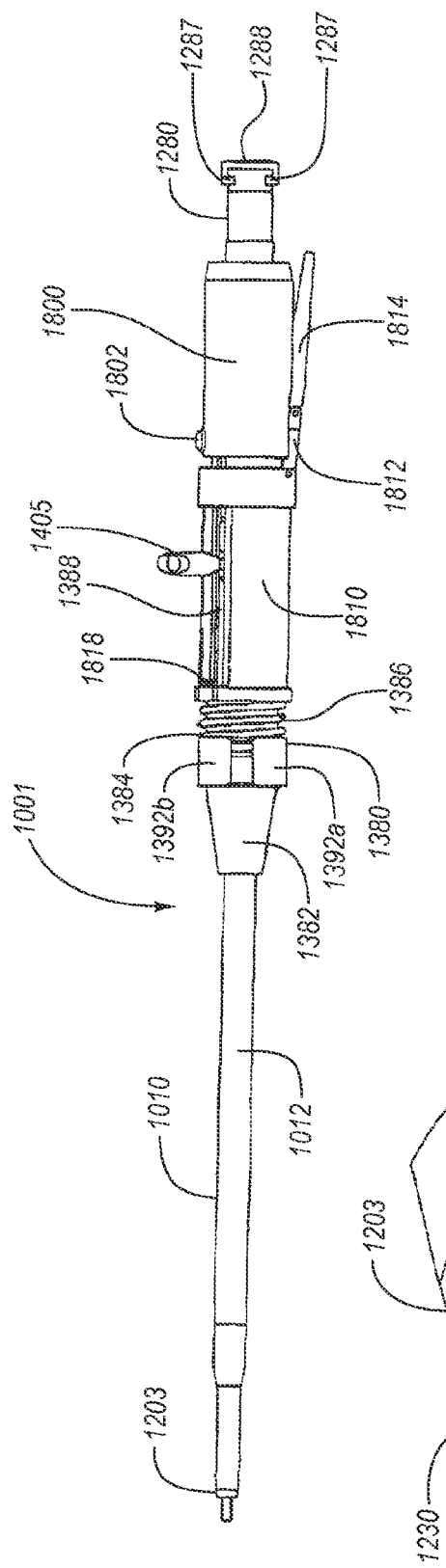
FIG. 16 illustrates a side view of another alternative embodiment of an apparatus for closing openings formed in blood vessel walls.
Figure 16A:
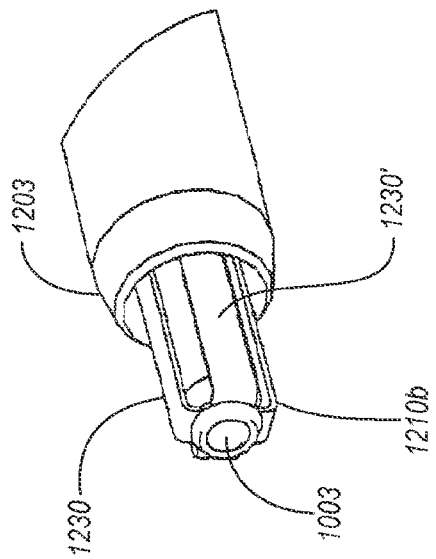
FIG. 16A illustrates a close-up view of the distal end of the device shown in FIG. 16.

Turning to FIGS. 16 and 16A, the device 1001 can be adapted for use in conjunction with a guidewire in an over the wire deployment method described below. The device 1001 can have a generally elongated body that includes, beginning at its proximal end, an actuator cap 1280, a generally cylindrical actuator housing 1800, a generally cylindrical release barrel 1810, a generally cylindrical main housing 1380, and a distal extension 1010, with locator elements 1230 and a hemostasis member 1203 disposed at the distal end. Several components of a locator assembly, a carrier assembly, and a triggering system can be contained within the main housing 1380, as described more fully below in relation to FIGS. 18 and 19. The distal extension 1010 of the device can include an external protective sheath 1012 that covers the distal portions of the locator assembly and carrier assembly. The distal end region 1210*b* of the locator assembly can extend out of the distal end of the protective sheath 1012.

With particular reference to FIG. 16A, the distal end region 1210*b* of the locator assembly can include expansion elements 1230 that include substantially flexible members 1230' and include an expandable hemostasis member 1203. The substantially flexible members 1230' and expandable hemostasis member 1203 can be selectively controllable between and unexpanded state (as shown in FIG. 16A) and an expanded state, generally in the manner described above in relation to FIGS. 2A-2D. As shown in FIG. 16A, the locator assembly of the alternative embodiment of the device 1001 can be provided with a central lumen 1003, which is illustrated with a diameter sufficient to accommodate a standard guidewire or other structure, as appropriate. As described below, the central lumen 1003 can extend through the length of the locator assembly and, thus, through the length of the device 1001.

Turning again to FIG. 16, the main housing 1380 can include a pair of grips 1392a-b integrally formed on opposite sides of the main housing 1380. The distal end of the main housing 1380 can be gradually tapered 1382, with the protective sheath 1012 extending out of its distal end. A cylindrical counter spring 1386 can be located coaxially on the external surface of the main housing 1380 and rests, at its distal end, against a shoulder 1384 formed in the main housing just proximal to the section of the main housing upon which the grips 1392a-b are formed. The proximal end of the counter spring 1386 can rest against the release barrel 1810, biasing the release barrel 1810 proximally in relation to the shoulder 1384 formed on the main housing 1380. The release barrel 1810 is generally cylindrical and coaxially surrounds the main housing 1380. A mechanical linkage 1812 can connect the release barrel 1810 to a release lever 1814 that cooperates with an actuator block 1282, as described more fully below in reference to FIGS. 18 and 19. A longitudinal slot 1388 can be formed on each of the main housing 1380 and the release barrel 1810, through which extends a lever 1405 that, as described below, is used to advance the carrier assembly in the distal direction to operate the device 1001.

A calibration set screw 1818 can be located on the release barrel 1810 near the distal end of the slot 1388. As the user advances the lever 1405 distally to deploy the closure element 500 similar to that described above and shown in FIGS. 6A-6G, the lever 1405 will eventually engage the calibration set screw 1818. As described below, further distal advancement of the lever 1405 can cause the actuator block 1282 to release, thereby causing the locator assembly to release the expansion elements 1230 and 1230' from the expanded state to the unexpanded state. The lever 1405 can also cause the hemostasis member 1203 to similarly retract to an unexpanded state. Thus, the setting of the calibration set screw 1818 can allow the user to fine tune the synchronization of the release and retraction to an unexpanded state of the locator assembly and hemostasis member 1203 with the deployment of the closure element 500, as described below.

Figure 19:
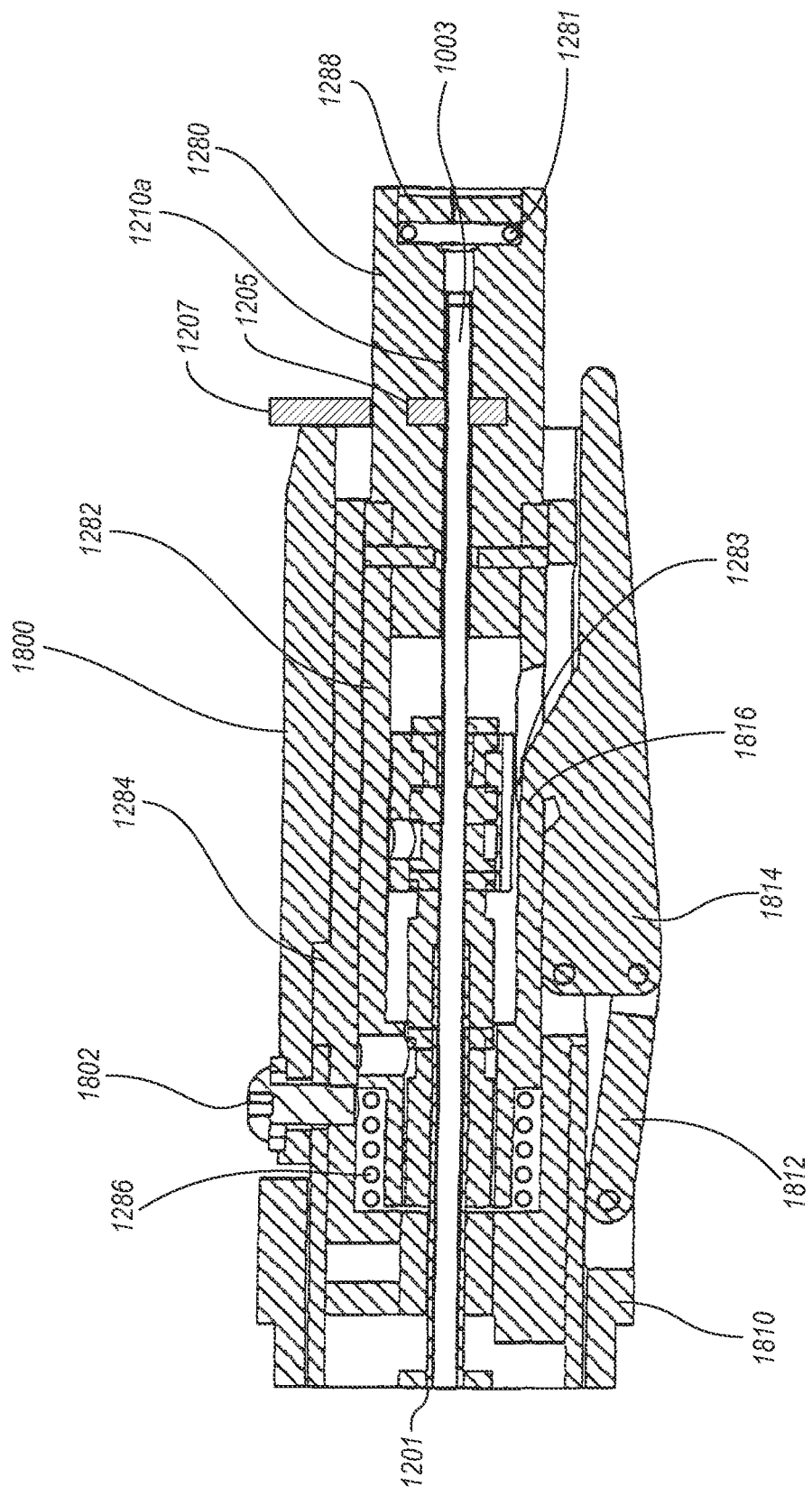
FIG. 19 illustrates a close-up cross-sectional view of the proximal end of the device shown in FIG. 16.

The actuator housing 1800 can be attached by a screw 1802 to the proximal end of the main housing 1380, and extends proximally from the main housing 1380. A longitudinal slot 1804 can be formed in the actuator housing 1800 to accommodate the release lever 1814 and the linkage 1812 (FIG. 18-19). The actuator cap 1280 can extend out from the proximal end of the actuator housing 1800. The actuator cap 1280 can be a generally cylindrical body that is coaxial with and generally internal of the actuator housing 1800. The actuator cap 1280 can include a slide seal 1288 at its proximal end that is slidable and that provides a fluid-tight seal, as described in more detail below. Additional details concerning the actuator are described below in reference to FIGS. 18 and 19.

Figures 17, 17A:
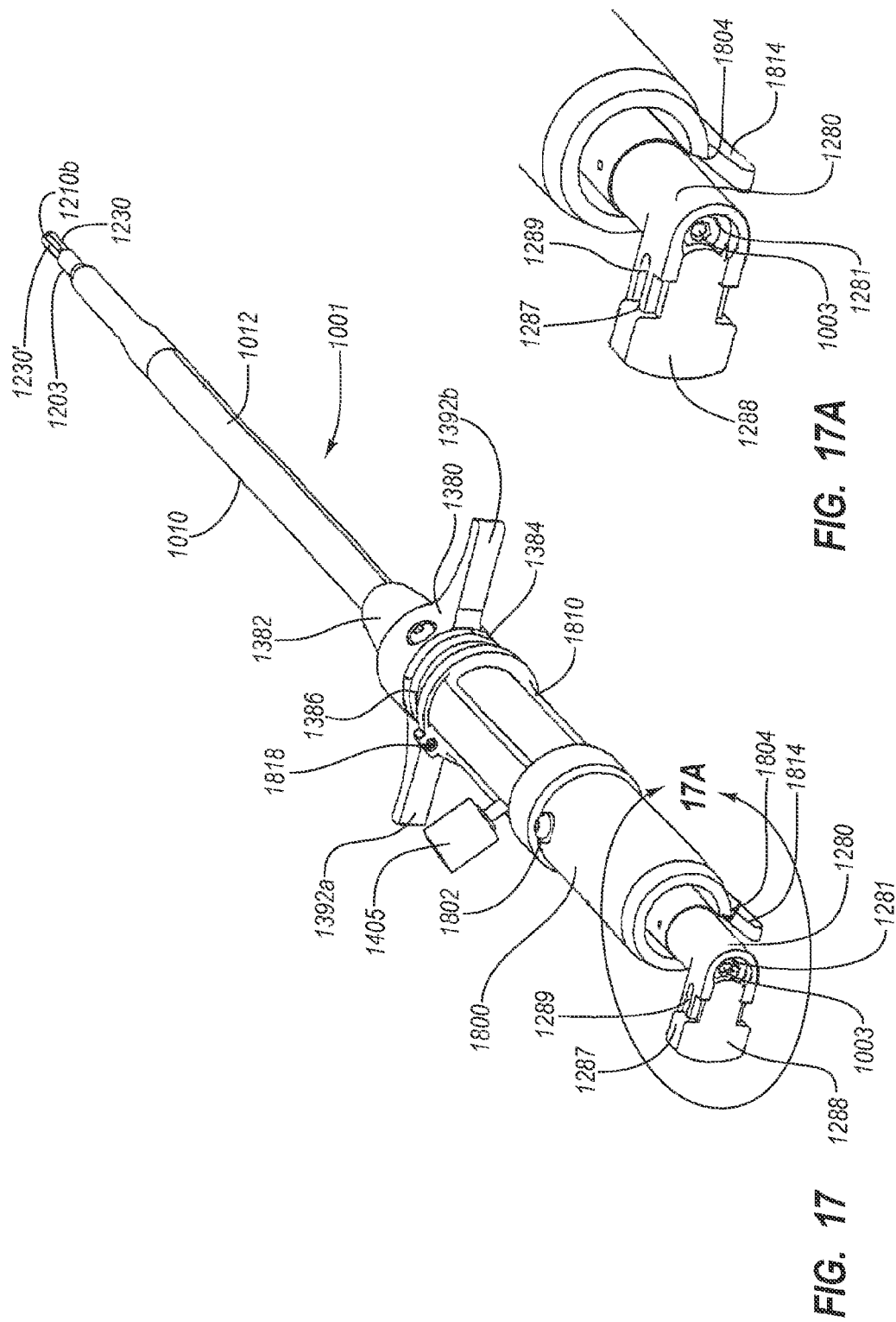
FIG. 17 illustrates a perspective view of the proximal end of the device shown in FIG. 16.
FIG. 17A illustrates a close-up view of the proximal end of the device shown in FIG. 17.

Turning to FIGS. 17 and 17A, the proximal end of the device is shown in more detail. As shown, the slide seal 1288 on the actuator cap 1280 has been slid to an open position to expose the interior of the actuator. The slide seal 1288 can be provided with a pair of tabs 1287 that cooperate with a pair of slots 1289 formed on the proximal end of the actuator cap 1280 to allow the slide seal 1288 to slide in relation to the actuator cap 1280. The actuator cap 1280 can include a seal 1281, such as an o-ring, that provides a fluid tight seal with the slide seal 1288.

As described above and as shown in FIGS. 17 and 17A, the central lumen 1003 can extend longitudinally through the center of the device and is accessible at the proximal end of the actuator cap 1280 when the slide seal 1288 is in the open position. Additional details concerning the central lumen 1003 are described below in relation to the additional Figures.

FIG. 17 provides additional detail concerning the shape and orientation of the grips 1392 formed on the main housing. As shown, the grips 1392 can extend radially outward on opposite sides of a point near the distal end of the main housing 1380, and provide the user with the ability to grip the housing with two fingers while operating the lever 1405 with the user's thumb. Also shown in FIGS. 17 and 17A is the slot 1804 formed in the actuator housing 1800 to accommodate the release lever 1814.

FIGS. 18, 18A, and 18B show a cross-section of the proximal portion of the device 1001, including the previously described main housing 1380, the release barrel 1810 located coaxially in a slidable relation on the external surface of the main housing, the counter spring 1386 that biases the release barrel proximally relative to the shoulder 1384 formed on the main housing, the actuator housing 1800 extending proximally from the proximal end of the main housing, the linkage 1812 and release lever 1814 connected to the release barrel 1810, and the actuator cap 1280 extending proximally from the proximal end of the actuator housing 1800. The actuator cap 1280 can be attached to, or formed integrally with, an actuator block 1282 that is generally cylindrical and that is adapted to slide longitudinally within an actuator base 1284. The actuator base 1284, in turn, can be attached by the screw 1802 to the proximal end of the main housing 1380 and the distal end of the actuator housing 1800, as shown in FIG. 18.

The central lumen 1003 is shown extending through the length of the device along its longitudinal axis. The central lumen 1003 can be defined by the interior diameter of the tubular body 1210 of the locator assembly 1200, which extends from the proximal end region 1210a to a distal end region 1210b (FIG. 16A). The proximal end region 1210a of the tubular body 1210 can be attached or otherwise connected to the actuator block 1282 such that when the actuator block 1282 is advanced distally the tubular body 1210 is also advanced distally, thereby causing the flexible members 1230' to buckle and/or expand transversely outwardly, (in the manner described above, for example, in relation to FIGS. 2A-2D), thereby transitioning the distal end region 1210b of the locator assembly 1200 from the unexpanded state to the expanded state. For example, in FIG. 18, the actuator cap 1280 is shown in the extended position, consistent with the locator assembly 1200 being in the unexpanded state. In FIG. 19, the actuator cap 1280 is shown in the depressed position, consistent with the locator assembly 1200 and optionally the hemostasis member (not shown) being in the expanded state. An actuator spring 1286 can be located in a chamber 1285 formed within the interior of the device between the distal end of the actuator block 1282 and the actuator base 1284 attached to the proximal end of the main housing 1380 and the distal end of the actuator housing 1800. The actuator spring 1286 can bias the actuator block 1282 in the proximal direction. Depressing the actuator cap 1280 can cause the actuator spring 1286 to compress within the chamber 1285. Once the actuator cap is fully depressed, the release lever 1814 can be rotated inwardly such that a catch 1816 formed on the release lever engages a slot 1283 formed on the actuator block 1282, thereby holding the actuator block 1282 in place in the depressed position against the spring force of the actuator spring 1286. The release lever 1814 may be disengaged, thus transitioning the locator assembly 1200 and/or the hemostasis member from the expanded state to the unexpanded state, either by manually releasing the release lever 1814 from the actuator block 1282 and allowing the actuator block to extend proximally, or by advancing the carrier assembly lever 1405 distally to engage the calibration set screw 1818 on the release barrel 1810 and applying additional distal force to the lever 1405 (and, thus, the release barrel 1810) to cause the release lever 1814 to disengage from the actuator block 1282. For example, the release lever 1814 may have two stages, one for the locator assembly 1200 and one for the hemostasis member.

Also, the device 1001 can include a hemostasis block 1205 that is controlled by a hemostasis actuator 1207. The hemostasis actuator 1207 can operate with the hemostasis block 1205 so as to control the hemostasis tube 1201 and/or hemostasis member as described herein. For example, the hemostasis actuator 1207 can function similarly to the release lever 1804 and/or to the lever 1405.

B. Tube Set

A carrier assembly 1300 can include a tube set 1305 that can be located within the interior of the main housing 1380, extending distally through the distal extension 1010. The tube set 1305 shown in FIG. 18 includes a carrier tube 1310, a pusher tube 1320, and a cover tube 1330, each located in a coaxial orientation with each other and with the tubular body 1210 of the locator assembly 1200 and/or hemostasis tube 1201 and hemostasis member. The tube set 1305 can have a structure otherwise substantially identical to that described above in relation to FIGS. 3A-3E. The cover tube 1330 can be connected or otherwise attached at its proximal end to a cover block 1430. The pusher tube 1320, similarly, can be connected or otherwise attached at its proximal end to a pusher block 1420. Finally, the carrier tube 1310 can be connected or otherwise attached at its proximal end to a carrier block 1410. The lever 1405 can be attached to the pusher block 1420. Thus, any movement of the lever 1405 may cause the pusher block 1420 to move as well.

C. Clip Applier Components

A leaf spring 1418 can connect the carrier block 1410 to the pusher block 1420, as shown in FIG. 18B. The leaf spring 1418 can be generally flat and can extend longitudinally parallel to the central axis of the device. A lip 1419 can be formed on the distal end of the leaf spring 1418, the lip 1419 oriented such that it engages the distal end of the pusher block 1420, effectively locking the pusher block 1420 to the carrier block 1410 until the leaf spring 1418 is disengaged from the pusher block 1420, as described below. As long as the pusher block 1420 is thereby locked to the carrier block 1410, advancement of the lever 1405 may cause advancement of the combination of the carrier block 1410 and the pusher block 1420.

A guide pin 1900 can be located and fixed on the interior of the main housing 1380, and can extend proximally from the distal wall of the interior of the main housing. The guide pin 1900 can be received within a slot 1902 formed in the pusher block 1420 and cover block 1430, and can prevent the pusher block 1420 and cover block 1430 from rotating inside the main housing 1380.

A grooved pin 1910 can be located and fixed on the interior of the main housing 1380, and can extend proximally from the distal wall of the interior of the main housing 1380. The grooved pin 1910 can be located on an opposite side of the interior of the main housing from the guide pin 1900. The grooved pin 1910 can have a taper 1912 formed on its proximal end and a transverse groove 1914 formed just distally from the beginning of the taper 1912. The location and orientation of the grooved pin 1910 can be such that the taper 1912 formed on the grooved pin 1910 engages and lifts the leaf spring 1418 from its engagement with the pusher block 1420 as the pusher block 1420 and carrier block 1410 are advanced distally within the device. As the pusher block 1420 and carrier block 1410 are advanced still further, the lip 1419 formed on the leaf spring 1418 can engage and lock in place in the transverse groove 1914 formed on the grooved pin 1910, thereby preventing the carrier block 1410 (and, thus, the carrier tube 1310) from advancing any further distally. This position of the device also corresponds to the engagement of the lever 1405 with the calibration set screw 1818 (FIG. 16). Any additional distal movement of the lever 1405 may cause the pusher block 1420 to move further distally while the carrier block 1410 remains stationary, thus causing the pusher tube 1320 to deploy the closure element 1500, in the manner described above in relation to FIGS. 8A-8L. This additional distal movement of the lever 1405 may simultaneously cause the release barrel 1810 to move distally and to disengage the release lever 1814 from the actuator block 1282, thereby releasing the actuator block 1282 and causing the locator assembly 1200 to transition from the expanded state to the unexpanded state.

D. Closure Element Delivery

Referring now to FIGS. 20A-20G, methods of use of the device 1001 (see FIGS. 16-19) in accordance with the present invention will be described. As previously described above and shown in FIGS. 16-19, the device 1001 can be configured to deploy a closure element 1500 over a wire 1950, wherein the over the wire deployment method utilizing the device 1001 described herein may for example include the following steps, though methods of use associated with the apparatus should not be limited to those described herein or shown in the appended drawings. Additionally, the device 1001 can include a clip carrier assembly 1300 having the tube set 1305 that has the following: a support tube 1340 with a distal end 1340*b*; a carrier tube 1310 with a distal end 1310*b*; a pusher tube 1320 with a distal end 1320*b*; a cover tube 1330 with a distal end 1330*b*; and a clip 1500" having tines 1520 disposed in a cavity 1370. A locator assembly 1200 having a locator tube 1210 with locator member 1220 disposed at a distal end 1210*b* is included within the carrier assembly 1300. A hemostasis tube 1201 for controlling the expandable hemostasis member 1203 is also included. It should be recognized that the hemostasis tube 1201 and hemostasis member 1203 can be integrated together or separate components that operate together for providing improved hemostasis.

Figure 20A:
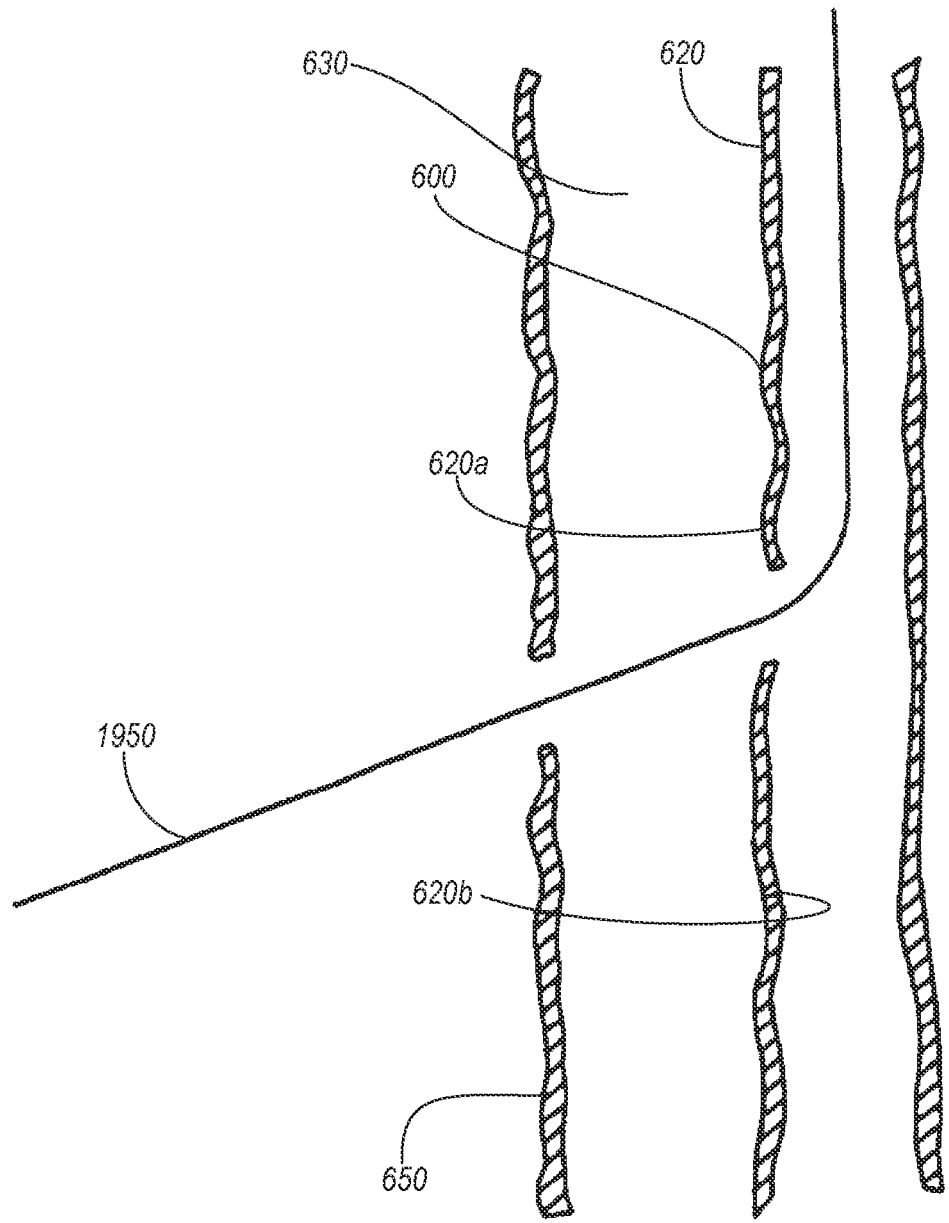
FIG. 20A is a cross-sectional side view illustrating an opening formed in a vessel, wherein a guidewire is shown disposed within the opening.

Referring now to FIG. 20A, there is shown a vessel 620 disposed below a patient's tissue 630 and skin 650, wherein a guidewire 1950 is shown disposed through an opening formed in the vessel and tissue as described above. The guidewire 1950 may be introduced into the blood vessel for the sole purpose of using the device 1001 to deploy the closure element 1500, or the guidewire may have already been present from a previously completed interventional procedure. If an introducer sheath is in place, it should be removed prior to use of the apparatus 1001, thereby leaving the guidewire 1950 in place extending into the blood vessel.

Figure 20B:
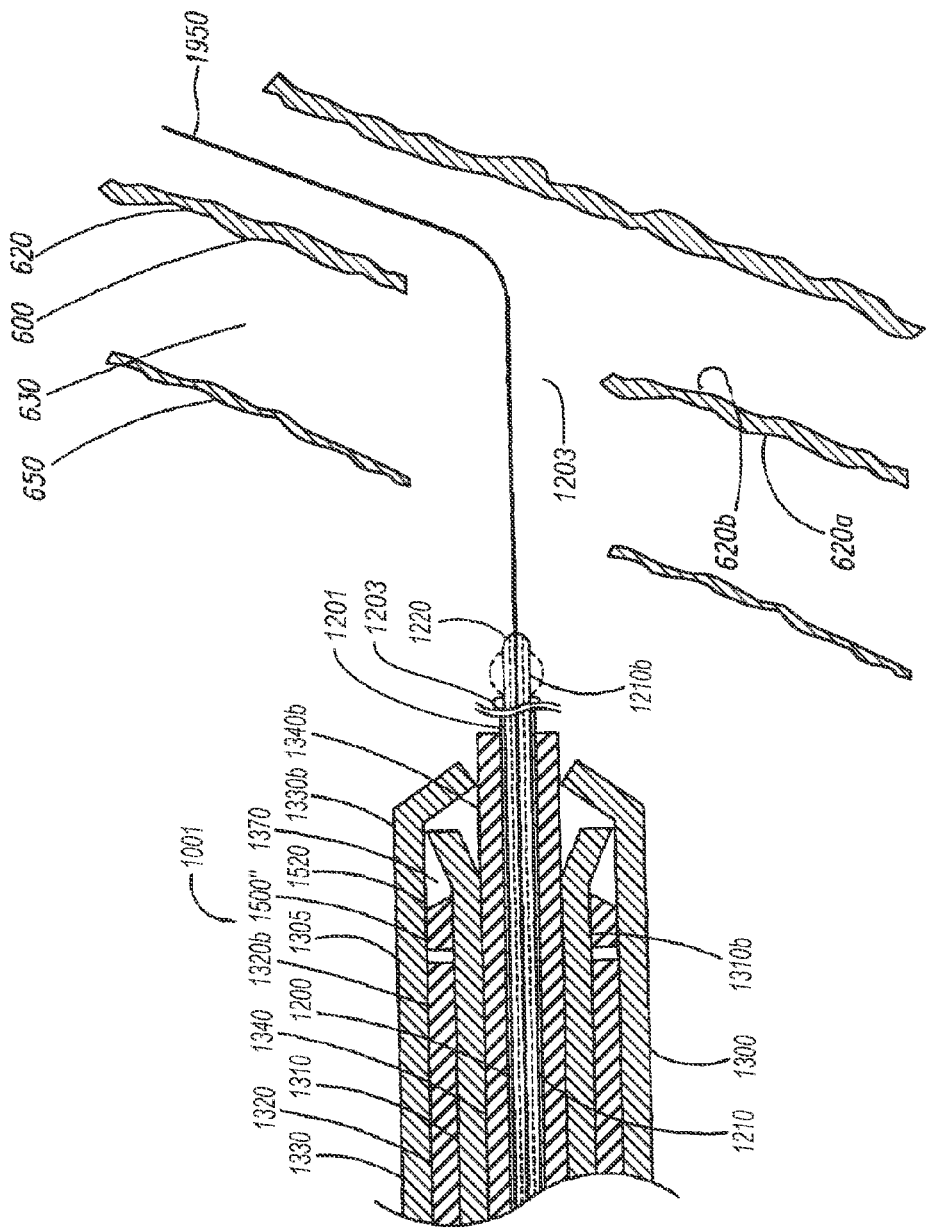
FIG. 20B-20F are partial cross-sectional views illustrating the alternative embodiment of the closure device in accordance with the present invention wherein the device is illustrated being disposed over a guidewire.
Figure 20C:
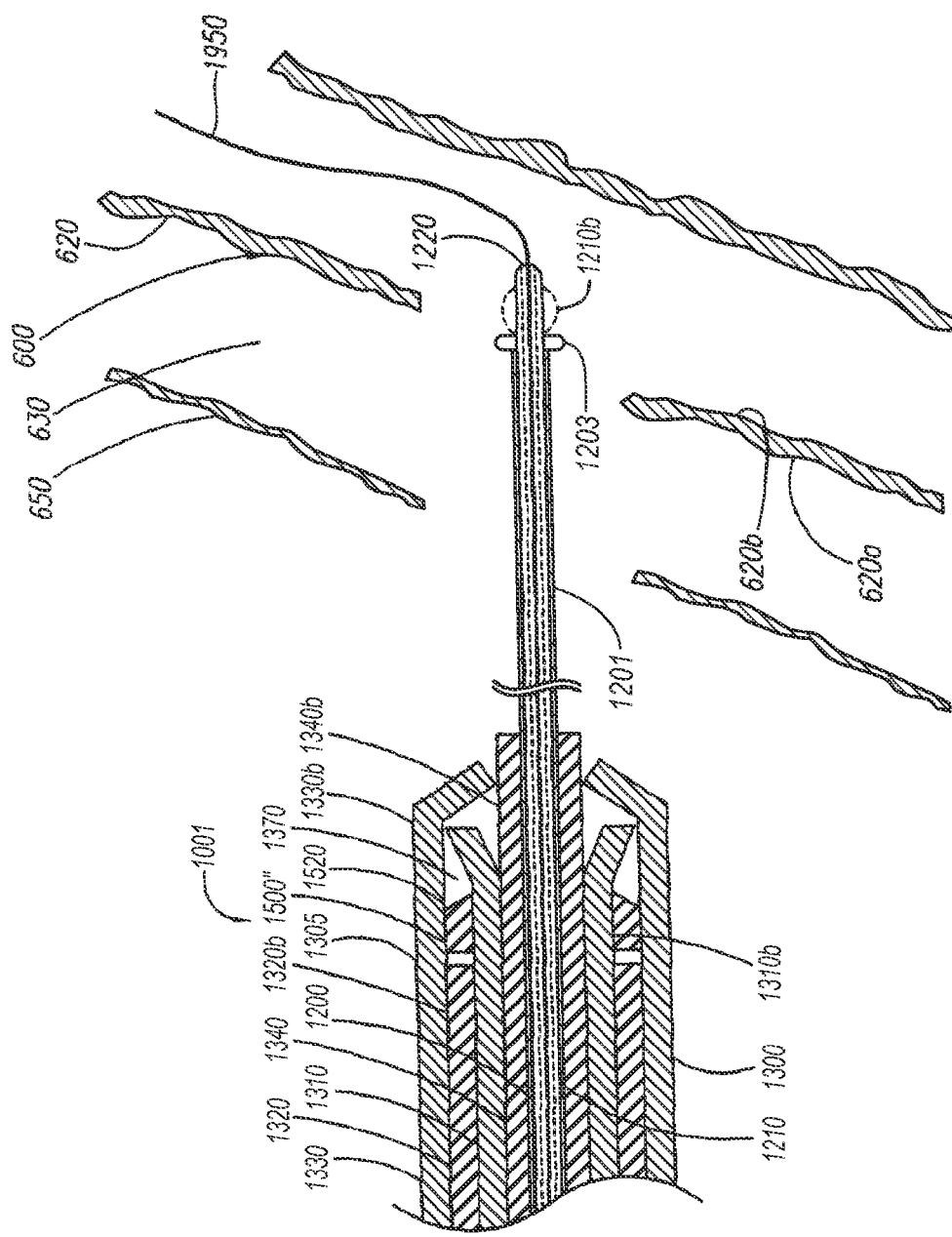

As shown in FIG. 20B, the device 1001 can be threaded over the guidewire 1950 by inserting the proximal end of the guidewire 1950 into the central lumen of the device 1001 at the distal end of the device, the guidewire is disposed through the device and exits at the proximal end of the device. The device 1001 can be advanced along the guidewire until the distal end 1210*b* (e.g., locator 1220) and the hemostasis tube 1201 and hemostasis member 1203 are disposed through the opening 610 formed in the blood vessel 620 as shown in FIG. 20C, whereby the correct position of the device 1001 is confirmed by observing a slight flow of blood out of the proximal end of the device, through the open slide seal 1288 on the actuator cap 1280.

Figure 20D:
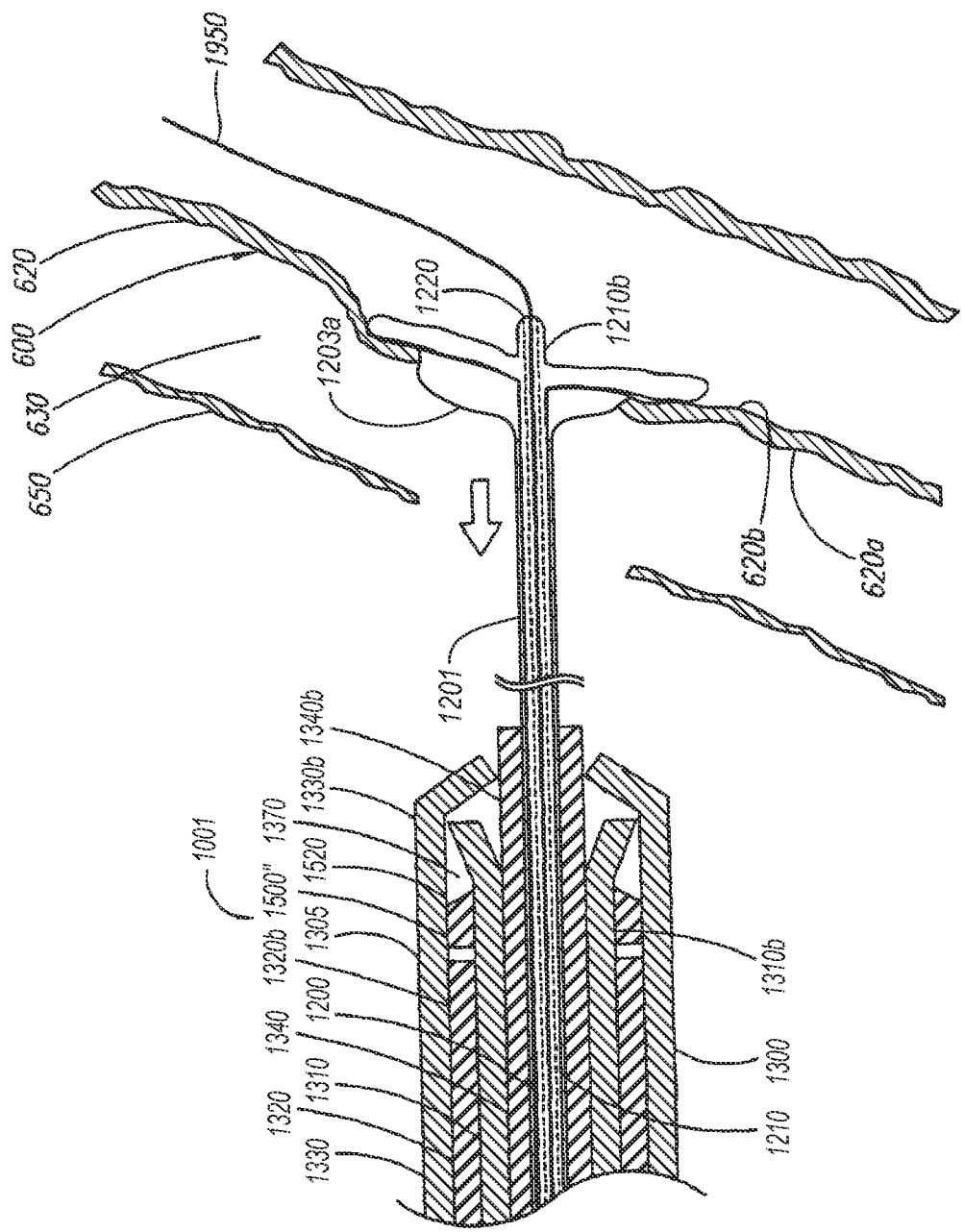
Figure 20E:
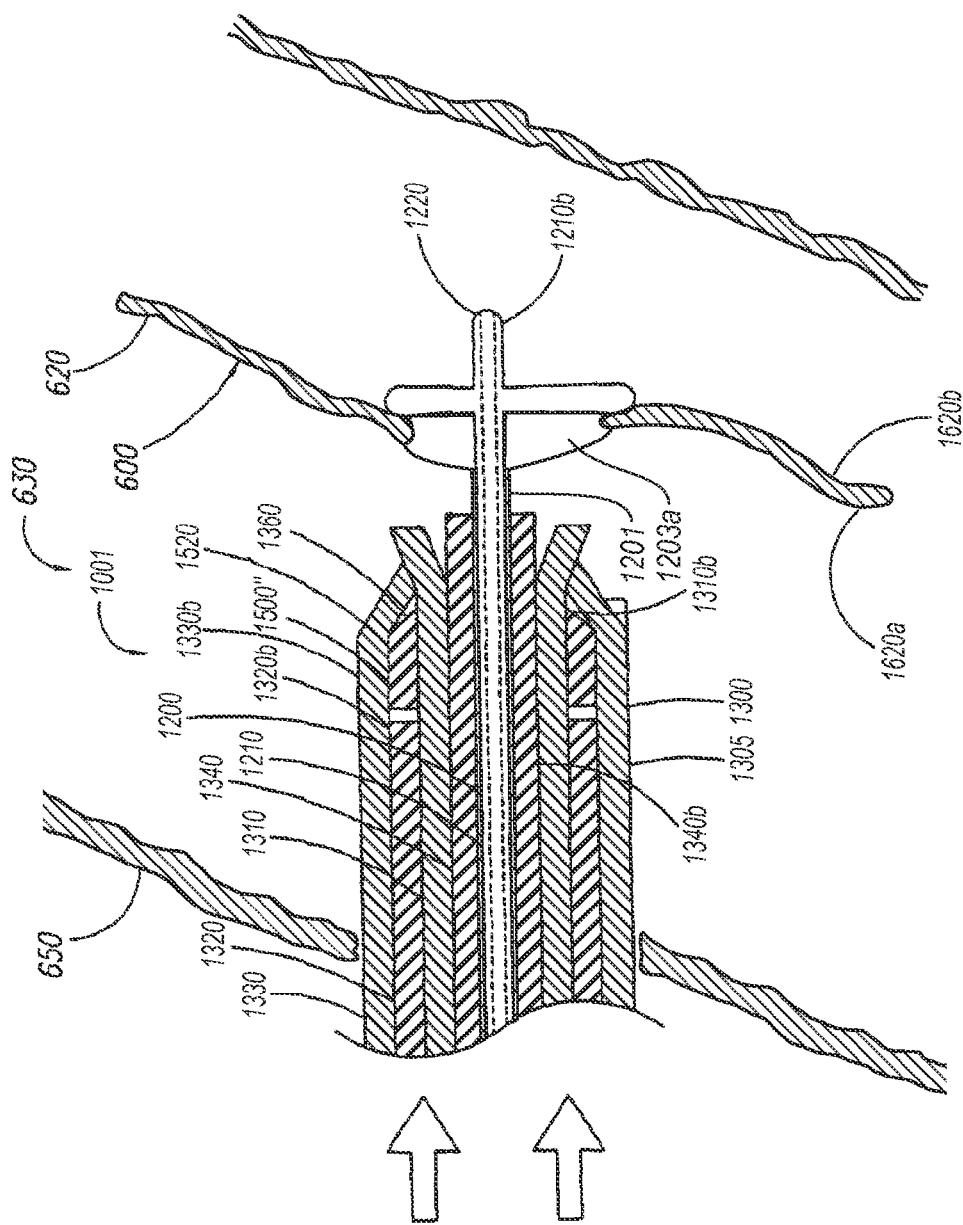

Once the correct position of the device 1001 is confirmed, the actuator cap 1280 can be depressed (i.e., the actuator block 1282 is advanced distally) to deploy the flexible members on the distal end 1210b of the locator 1220, i.e., to transition the locator 1220 from the unexpanded state to the expanded state. Either the actuator cap 1280 or a similar actuator (not shown) can be similarly actuated so as to selectively expand the hemostasis member 1203. In the expanded state, the flexible members of the locator 1220 can engage the inside of the vessel wall 620a at the location of the opening 610 in the blood vessel as shown in FIG. 20D. The correct position of the device 1001 at this point may be confirmed by gently pulling on the device to feel the resistance of the vessel wall 620a against the flexible members of the locator 1220 in the expanded state as shown in FIG. 20E. After verifying the correct position in this manner, the guidewire may be removed from the vessel 620 and from the device by withdrawing the guidewire through the proximal end of the device. Once the guidewire 1950 is removed, the slide seal 1288 on the actuator cap 1280 may be closed to prevent further flow of blood through the device.

At any point before, during, or after the locator 1220 is correctly positioned, the hemostasis tube 1201 can induce the hemostasis member 1203 to expand while being disposed within the opening 610 of the vessel 620. In some instances, it can be advantageous to expand the hemostasis member 1203 before the locator 1220 is expanded, which allows for improved hemostasis before any blood leaks through the opening. Similarly, the hemostasis member 1203 can be expanded as the locator 1220 is being positioned or shortly thereafter. In any event, the hemostasis member 1203 selectively expands within the opening 610 so as to provide a plug to the vessel 620. Depending on the length of the hemostasis member 1203 and/or expandability of the hemostasis tube 1201, hemostasis and the prevention of oozing from the tissue 630 can also be achieved. Alternatively, the hemostasis member 1203' can expand around the opening 610 and form a seal with the outer surface 620a of the vessel 620 as shown by the dashed lines.

Figure 20F:
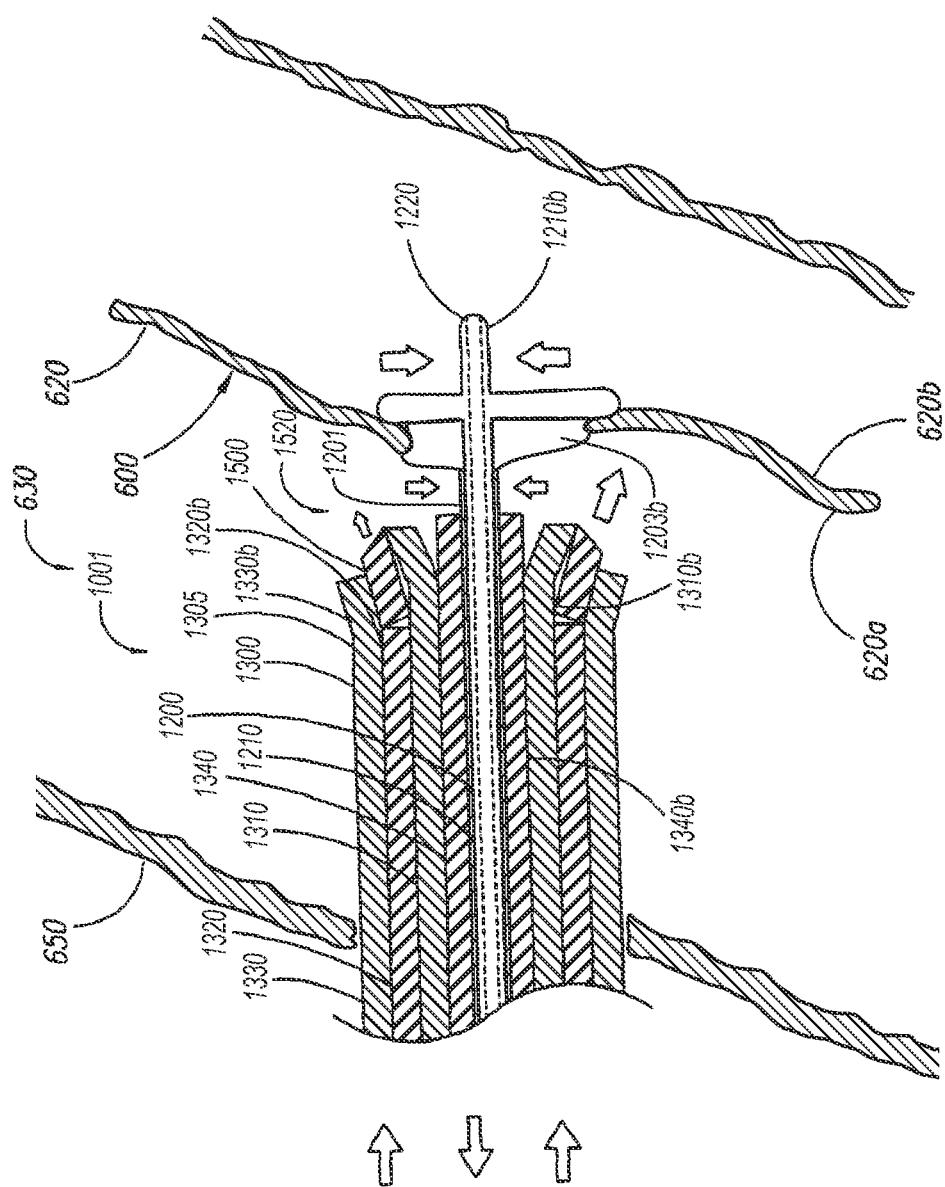
Figure 20G:
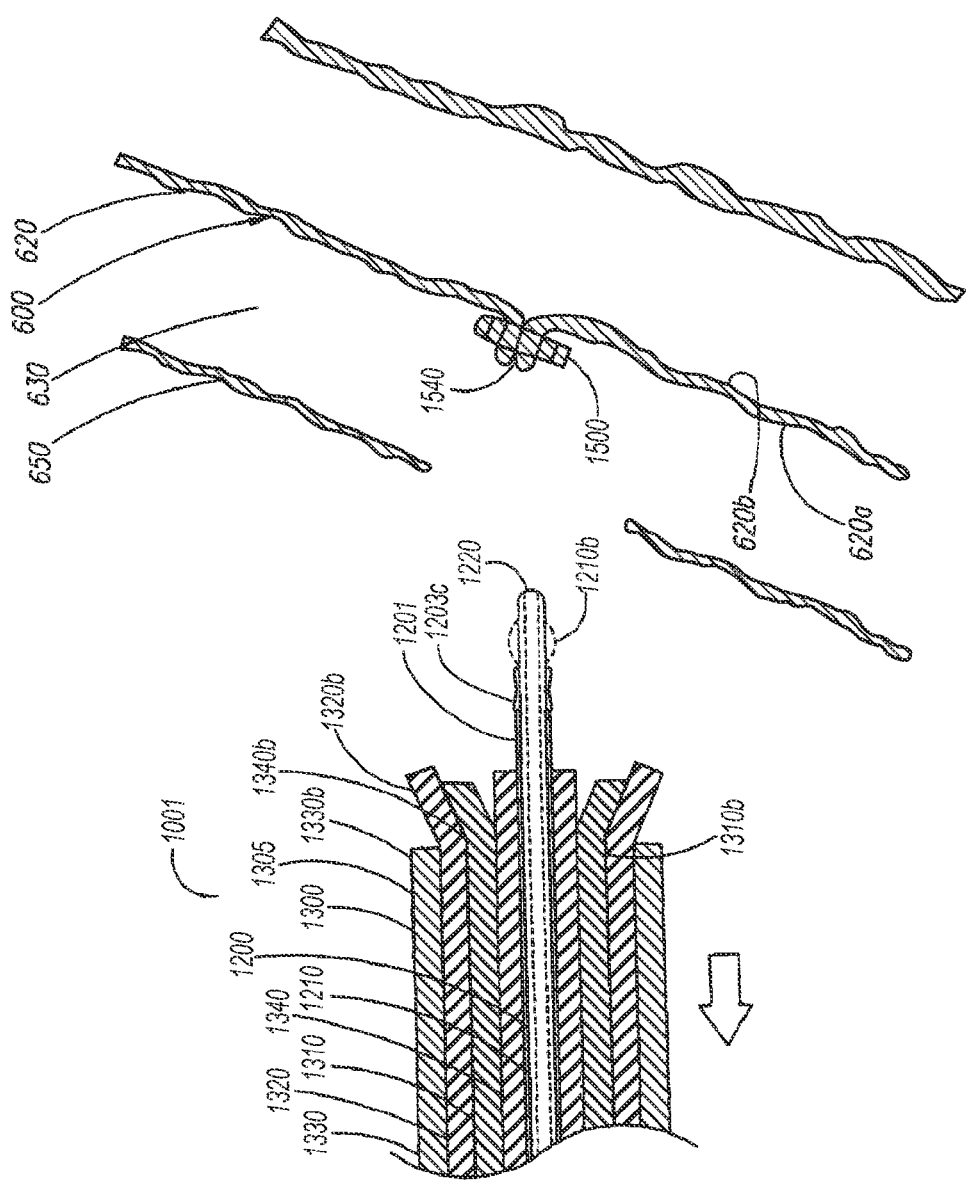
FIG. 20G is a partial cross-sectional view illustrating the placement of a closure element in accordance with the device illustrated in FIG. 20B-20F.

Referring now to FIGS. 20F and 20G, the device 1001 is in proper position to deploy the closure element 1500. The closure element 1500" can be deployed by advancing the lever 1405, which advances the carrier block 1410, pusher block 1420, and cover block 1430 until further distal advancement of the carrier block 1410 and cover block 1430 are prevented by the interaction of the leaf spring 1418 engaging and locking in place in the transverse groove 1914 formed on the grooved pin 1910, thereby preventing the carrier block 1410 (and, thus, the carrier tube 1310) from advancing any further distally. Further distal advancement of the lever 1405 thereafter can cause advancement only of the pusher block 1420, which causes deployment of the closure element 500 in the identical manner described above, for example, in relation to FIGS. 8H-L. In addition, further distal advancement of the lever 1405 can cause the lever 1405 simultaneously to engage the release barrel 1810, which in turn pulls the release lever 1814 and frees the actuator block 1282 to spring back proximally, transitioning the locator 1220 and hemostasis member 1203 from the expanded state to the unexpanded state. The closure element deployment and locator/hemostasis member release actions can occur nearly simultaneously, as illustrated, for example, in FIGS. 8I-8K. The hemostasis member can transition from an unexpanded state 1203 to an expanded state 1203a to a retracting state 1203b to a fully retracted and unexpanded state 1203c.

As shown in FIG. 20G, the closure element 1500 is shown in a deployed position, wherein the closure element has been engaged with the vessel wall to effectively close the opening formed therein. As previously described and shown in FIGS. 20F and 20G, the closure element 1500 can be expanded as it is deployed from the device 1001, wherein by increasing the diameter of the closure element 1500, the closure element may engage tissue adjacent the opening in the tissue. It is contemplated that the closure element may be configured to penetrate the vessel wall to effect a closure, or partially penetrate the vessel wall to effect closure.

FIG. 20H shows that the locator 1220 has been released so that it can be implanted by the closure element 1500 which grabs the locator 1220 as it is returning to the deployed position.

IV. Improving Hemostasis

Additionally, methods of using the improved hemostasis system described herein are shown in FIGS. 21A-21E. The methods can utilize embodiments of the hemostasis systems as shown in the various figures. As such, the use of a hemostasis member during the process of delivering a closure element to close an opening in a body lumen can be used as shown, and can have many identical or similar structures that perform identical or similar functions to the embodiments of the invention described herein in reference to the figures. Accordingly, the description below should be considered in view of the descriptions herein of the different embodiments of hemostasis systems and methods of using the same. Furthermore, those of ordinary skill in the art will appreciate that one or more of the uses, components, and/or features of the embodiment shown in FIGS. 21A-21E may also be incorporated in the other embodiments described herein, and vice versa.

Referring now to FIGS. 21A-21E, methods of using a hemostasis system 2201 will be described. The hemostasis system 2201 can be used with closure element applying devices described herein, and may include various features of such closure element applying devices as described herein. However, FIGS. 21A-21E only show the hemostasis system 2201 for purposes of clarity, and it should be understood that the hemostasis system 2201 is employed so as to provide improved hemostasis during the process of applying a closure element to seal a blood vessel 2600.

Figure 21A:
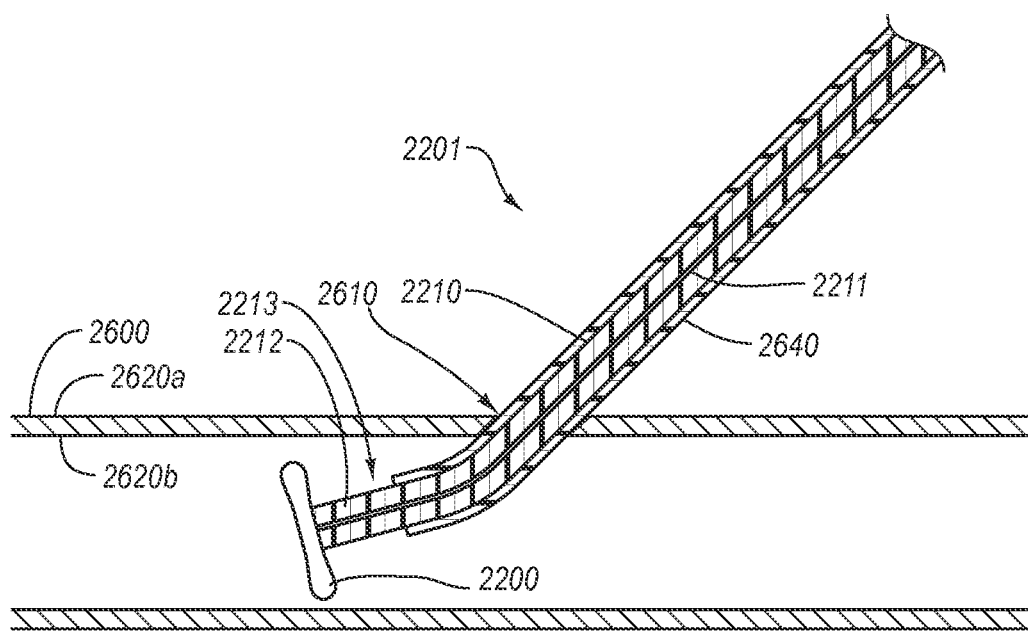
FIG. 21A-21E are partial cross-sectional views illustrating the luminal placement of a medical device for closing openings formed in blood vessel walls with improved hemostasis.

Referring now to FIG. 21A, there is shown a vessel 2620 having an external surface 2620a and an internal surface 2620b. The vessel 2620 includes an opening 2610 disposed therein where a medical device, such as a catheter, can be inserted for performing a medical procedure. As described above, a guidewire (not shown) can be inserted through the opening 2610 of the vessel 2620 such that the hemostasis system 2201 can be inserted into the opening 2610 by being traversed over the guidewire.

The hemostasis system 2201 is illustrated to include a sheath 2640 through which the components of the locator assembly, hemostasis components, and tube set, described herein, can be deployed into and/or adjacent to the opening 2610 in the vessel 2620. As illustrated in FIG. 21A, the sheath 2640 is disposed through the opening 2610 such that locator 2200 extends therefrom and into the vessel 2620. The hemostasis tube 2212 is also shown to extend from the sheath 2640 so as to form a gap 2213 between the sheath 2640 and the locator 2200. A wire 2211, or other suitable mechanism for operation of the locator 2200 and/or hemostasis system 2201 is disposed within a lumen in the hemostasis system 2201, such as within the hemostasis tube 2212.

Figure 21B:
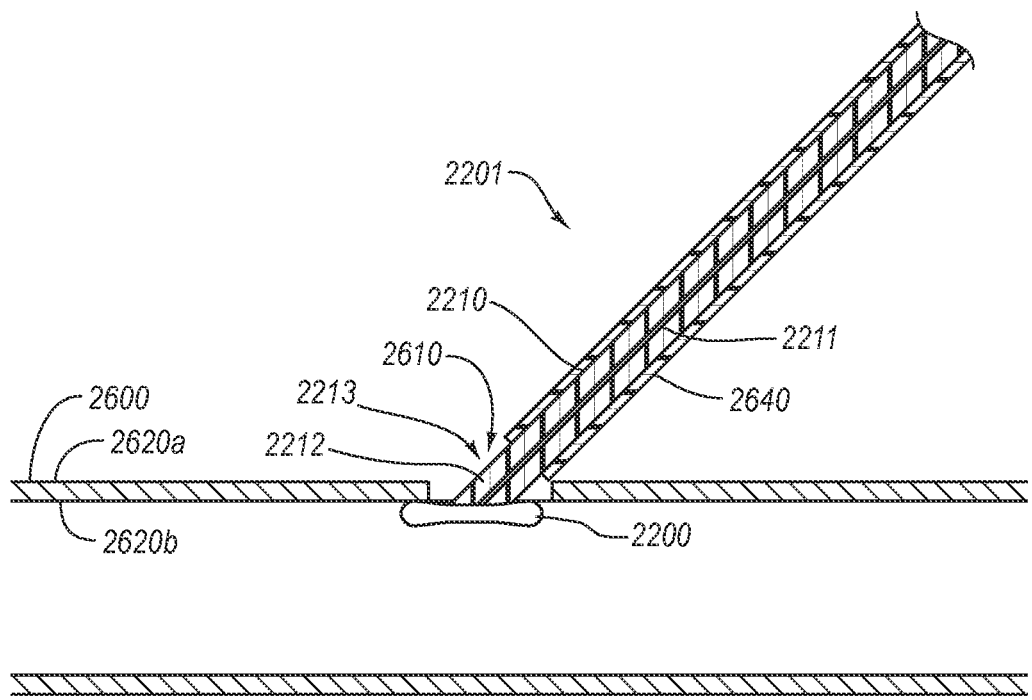

As shown in FIG. 21B, when the locator 2200 is withdrawn so as to locate the vessel 2620 by contacting the internal surface 2620b of the vessel, the gap 2213 is positioned at the opening 2610 of the vessel 2620. This provides incomplete hemostasis because blood is able to ooze, seep, and/or flow through the opening 2610 at the gap 2213. As such, the process of locating the vessel 2620 can cause incomplete hemostasis, which is undesirable.

Figure 21C:
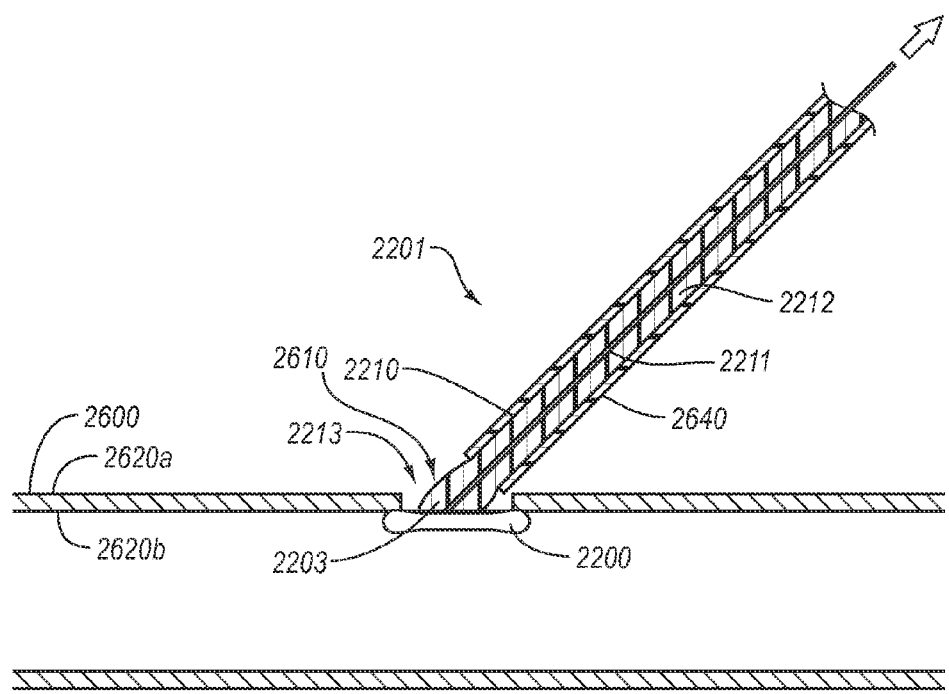

As shown in FIG. 21C, the hemostasis system 2201 can be manipulated so that an expandable member 2203 can be expanded so as to fill the gap 2213 and plug the opening 2610 in the vessel 2620. For example, the wire 2211 can be manipulated in a manner that causes the expandable member 2203 to begin to expand so as to fill the gap 2213 and plug the opening 2610 of the vessel 2620. In another example, the first manipulation of the wire 2211 can expand the locator 2200, and the second manipulation of the wire 2211 can expand the expandable member 2203. The order of which expandable members 2203 and/or the locator 2200 expand may be selected depending on the characteristics of improved hemostasis.

Figure 21D:
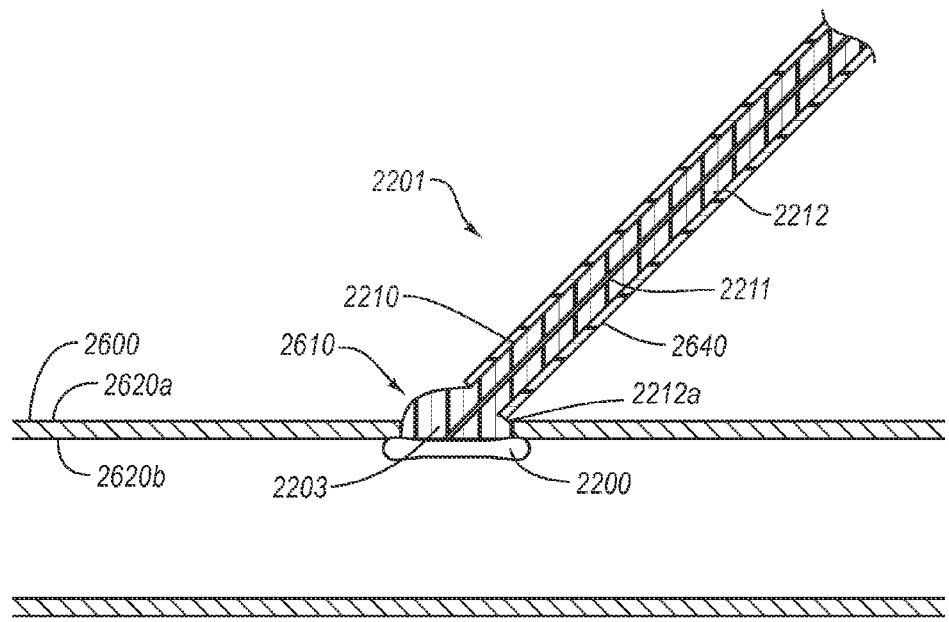

As shown in FIG. 21D, the fully expanded expandable member 2203 has a sufficient size to plug the opening 2610 in the vessel 2620. Also, the expanded expandable member 2203 provides hemostasis so that blood is inhibited from passing through the opening 2610. The expanded expandable member 2203 can extend from the locator 2200 to the sheath 2640 or any distance therebetween. The hemostasis can be maintained throughout the process of delivering the closure element into the vessel 2620 so as to close the opening 2610.

While not shown, the expandable member 2203 and locator 2200 can be collapsed as the closure element is deployed into the vessel 2620. The collapse of the expandable member 2203 and locator 2200 can be facilitated as described herein. For example, the wire 2211 can be manipulated in a manner that automatically causes the collapse as the closure element is delivered into the vessel 2620. Otherwise, the mechanism described herein that collapses the locator and hemostatic member as the closure element is deployed can be used.

Figure 21E:
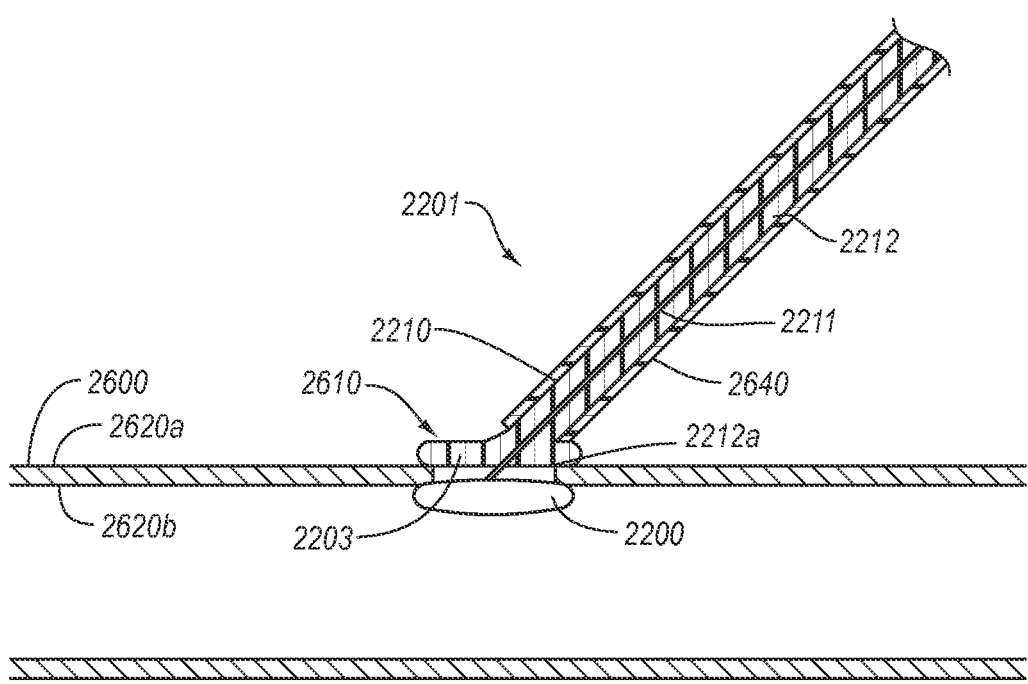

FIG. 21E shows the hemostasis system 2201 can include an expandable member 2203 that expands radially or laterally in a more disc-like configuration so that it can contact the outer wall 2620a of the vessel 2620 and form a seal to inhibit bleeding. An expandable hemostasis member 2203 can be configured as a cap and/or plug for the hole 2610 and may have an expanded outer diameter that is larger than the diameter of the hole 2610.

V. Hemostasis System

Generally, closure systems that are configured to close openings in body vessels can suffer from incomplete hemostasis during the closing procedure. Such incomplete hemostasis allows blood or other body fluids to seep into the medical devices and increase the difficulty in closing and sealing the opening. For example, in an embodiment of a current closure system, the nylon shaft of the locator system is smaller than the arteriotomy (e.g., 6F) or sheath. As the sheath is retracted during the positioning of the locator or split during the advancement of the tube set, blood can ooze out of the opening before the closure element is applied to close the opening. In order to inhibit the oozing of blood through the opening, the hemostasis system of the present invention can be applied to inhibit such oozing and provide improved hemostasis.

In one embodiment, the hemostasis is accomplished by the distal tip of the shaft of the locator selectively expanding. For example, the shaft can be a nylon shaft that is tensioned so as to longitudinally shorten and laterally buckle and expand at the distal end. Such buckling expands the nylon shaft laterally so as to plug or cap the opening in the vessel. Additionally, other embodiment of hemostasis systems can be applied as described herein.

A hemostasis system in accordance with the present invention is configured to substantially plug or cap an opening in a vessel so as to provide improved hemostasis during the deployment of a closure element into the vessel so as to close and seal the opening. Such a hemostasis system can be present in various configurations that have an expandable member that expands so as to plug the opening. Expandable members are well known in the art and can be expanded by a number of mechanisms.

The expandable members of the present invention can be self-expandable so as to automatically expand when subjected to a particular stimulus. Such self-expandable members can include shape-memory materials (e.g., shape memory alloys an shape memory polymers) that expand as is well known in the art. For example, shape memory alloys automatically expand when heated to a certain temperature by the body. Shape memory alloys, such as nitinol, are also known as superelastic metals.

Additionally, a self-expandable member can have an expanded configuration and a contracted configuration, where the member is retained within a device (e.g., sheath) in the contracted configuration and automatically expands when removed from the device. For example, the self-expandable member can have a contracted configuration that fits and is held therein by a sheath as described herein, and automatically expands to the expanded configuration when the sheath is retracted over the expandable member.

In one embodiment, the expandable member is fluid absorbable such that the fluid that oozes through the opening induces the expandable member to expand. An example of this can be a hydroscopic polymer (e.g., hydrogel) that swells and absorbs the body fluid.

In one embodiment, the expandable member is expanded when a mechanism is actuated so as to induce the expansion. This can be similar to a balloon, such as a balloon in a balloon-expandable stent, or an inflatable bladder. The mechanism can be a hydraulic or fluidic mechanism with tubes and pumps that can be automatic and/or selectively controlled.

In one embodiment, the mechanism can be a wire or shaft that changes the configuration of the expandable member from unexpanded to expanded and back to being unexpanded, as desired. Such an expandable member can have expandable elements and components similar to the locator assembly as described herein. This can include the expandable member expanding via the same mechanism that expands the locator assembly or a similarly configured mechanism.

Figure 22A:
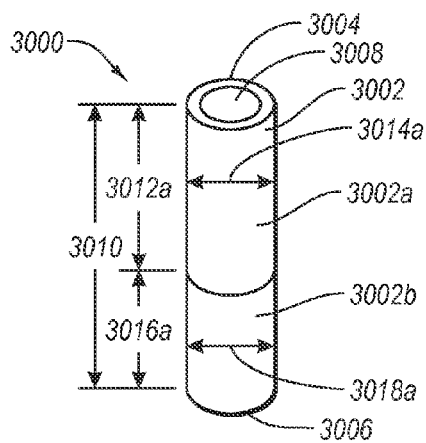
FIGS. 22A-22B are side views illustrating an embodiment of an expanding member for improving hemostasis during delivery of a closure device.
Figure 22B:
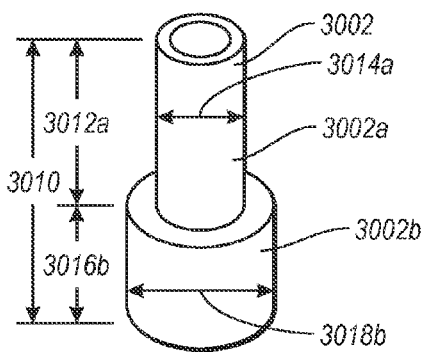

FIGS. 22A-22B are a schematic representation that shows expansion of an expandable hemostasis system 3000, where FIG. 22A shows the hemostasis system 3000 in the unexpanded state and FIG. 22B shows the expanded state. The hemostasis system 3000 includes a hemostasis member 3002 having an internal lumen 3008 that extends from a proximal end 3004 to a distal end 3006. The hemostasis member 3002 is divided into a non-expandable member 3002a at the proximal end 3004 and an expandable member 3002b at the distal end 3006. The non-expandable member 3002a and expandable member 3002b can be two separate materials joined together, or they can be a unitary material with a portion that selectively expands (e.g., expandable member 3002b). The hemostasis member 3002 can be any length 3010, which can be divided in any manner to provide an appropriate non-expandable member 3002*a* length 3012*a* and an appropriate expandable member 3002*b* length 3016*a* while in the non-expanded state. Also, the non-expandable member 3002*a* can have a non-expandable diameter 3014*a*, and the expandable diameter 3018*a* that is sufficient for providing hemostasis and plugging or capping the opening in the body lumen. After the hemostasis system 3000 is expanded as shown in FIG. 22B, the expandable member 3002*b* expands to a larger diameter 3018*b*. Such an expansion in diameter can result in longitudinal shortening in length 3016*b*.

Figure 23A:
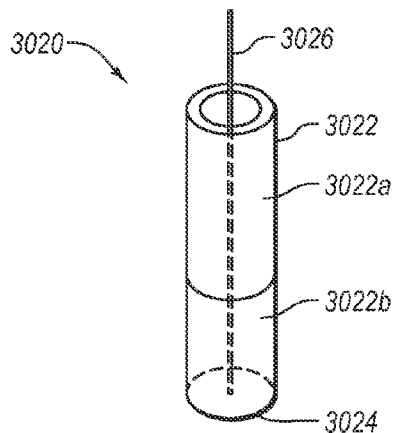
FIG. 23A-23F are side views illustrating different embodiments of expanding members for improving hemostasis during delivery of a closure device.

FIGS. 23A-23F are schematic illustrations of various other embodiments of hemostasis systems. FIG. 23A shows an embodiment of a hemostasis system 3020 in a non-expanded state that includes a hemostasis member 3022 that has a non-expanding member 3022*a* and an expanding member 3022*b*. Also, the hemostasis system 3020 includes a wire 3026 that is coupled to a rigid base 3024 such that a proximally oriented force applied to the wire 3026 can pull the rigid base 3024 so as to buckle and/or otherwise expand the expanding member 3022*b* relative to the non-expanding member. Alternatively, the wire 3026 can be configured as a tube, shaft, pin, combinations thereof, or the like that can provide a similar function in expanding the expanding member 3022*b*. As such, the wire 3026 can have sufficient tensile strength so as to impart a force to the expanding member 3022*b* so as to induce expansion thereof or activate a mechanism that expands the expanding member 3022*b*. The non-expanding member 3022*a* may be a separate material from the expanding member 3022*b* or a unitary material therewith. The non-expandable member 3022*a* may similarly expand if desired. However, an external structural member, such as a sheath or tube, can be used to hold the non-expanding member 3022*a* in place and restrict lateral expansion.

Figure 23B:
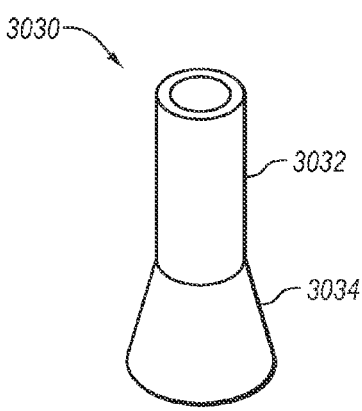

FIG. 23B shows an embodiment of a hemostasis system 3030 having a substantially tubular non-expanding member 3032 and an expanding member 3034 that expands to a substantially conical shape. The tubular non-expanding member 3032 may be capable of expanding; however, it is shown in the non-expanded state so as to be differentiated from the expanding member 3034 that expands within the opening of the vessel so as to form a plug. Also, the taper of the expanding member 3034 can be reversed with the larger end being coupled with the non-expanding member 3032. Insertion of the expanding member 3034 with the smaller end being inserted into a blood vessel can provide a plug/cap with a friction fit.

Figure 23C:
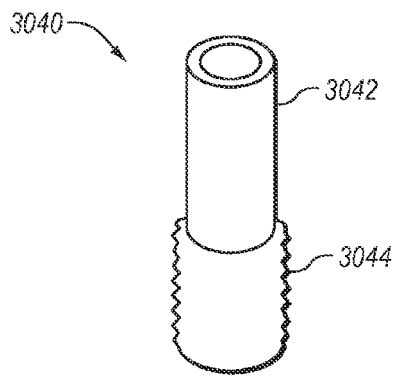

FIG. 23C shows an embodiment of a hemostasis system 3040 having a substantially tubular non-expanding member 3042 and an expanding member 3044 that buckles laterally so as to expand in diameter and shorten in length. The buckling can cause the lateral diameter to vary along the length with wide portions being of sufficient diameter to function as a plug in the opening and provide improved hemostasis. The buckling can also contour with the shape of the blood vessel opening and/or expand greater at the proximal end.

Figure 23D:
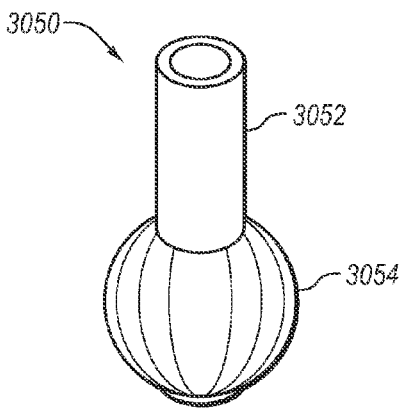

FIG. 23D shows an embodiment of a hemostasis system 3050 having a substantially tubular non-expanding member 3052 and an expanding member 3054 that expands or bows outwardly in the lateral direction. The bowing outwardly can cause the lateral diameter to change or curve along the length with wide portion being of sufficient diameter to function as a plug in the opening and provide improved hemostasis. Usually, the bowing is caused by the material curving outwardly, laterally rather than the material buckling. Alternatively, the bowing can also be similar to the inflation of a balloon or bladder.

Figures 23E, 23F:
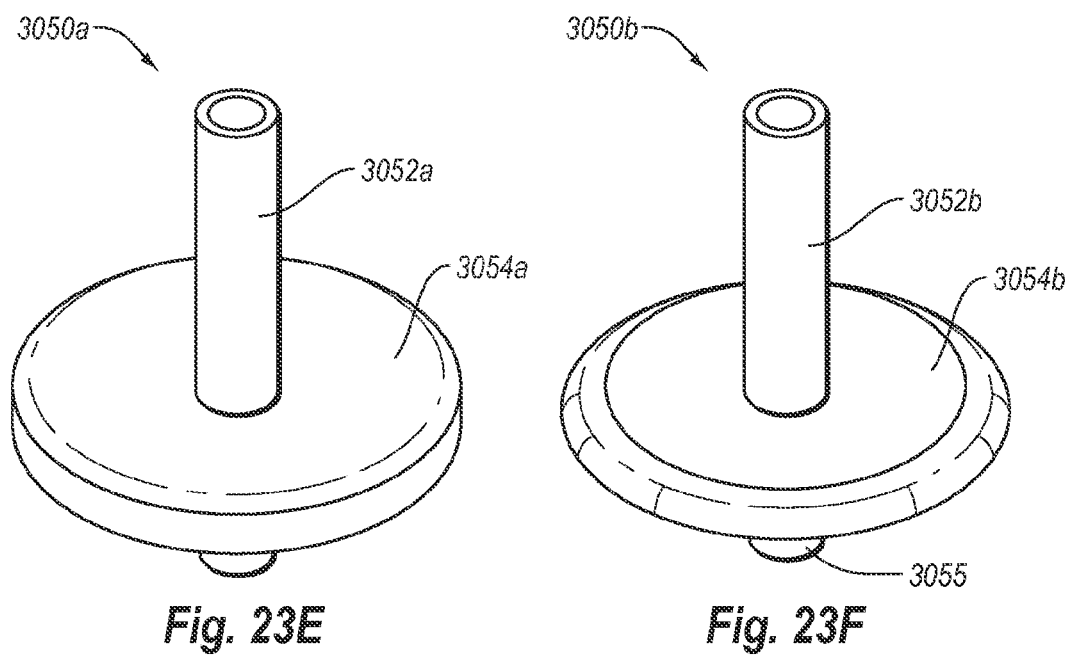

FIG. 23E shows an embodiment of a hemostasis system 3050*a* having a substantially tubular non-expanding member 3052*a* and an expanding member 3054*a* that expands or widens outwardly in the lateral direction to form a plate or discus like shape. The outward expansion can cause the lateral diameter to change to a sufficient diameter to function as a plug, cap, lid or other covering that provides hemostasis to the opening. Usually, the widening is caused by the material expanding outwardly, laterally rather than the material buckling. Alternatively, the widening can also be similar to the inflation of a balloon or bladder.

FIG. 23F shows an embodiment of a hemostasis system 3050*b* having a substantially tubular non-expanding member 3052*b* and an expanding member 3054*b* that expands or widens outwardly in the lateral direction to form a cupped, suction cup, or Frisbee like shape that can. The outward expansion can cause the lateral diameter to change to a sufficient diameter to function as a plug, cap, lid or other covering that provides hemostasis to the opening. Usually, the widening is caused by the material expanding outwardly, laterally rather than the material buckling. Alternatively, the widening can also be similar to the inflation of a balloon or bladder. Additionally, the distal or vessel side of the expanding member 3054*b* can include a plug 3055 that inserts into and plugs the vessel hole.

Figure 24A:
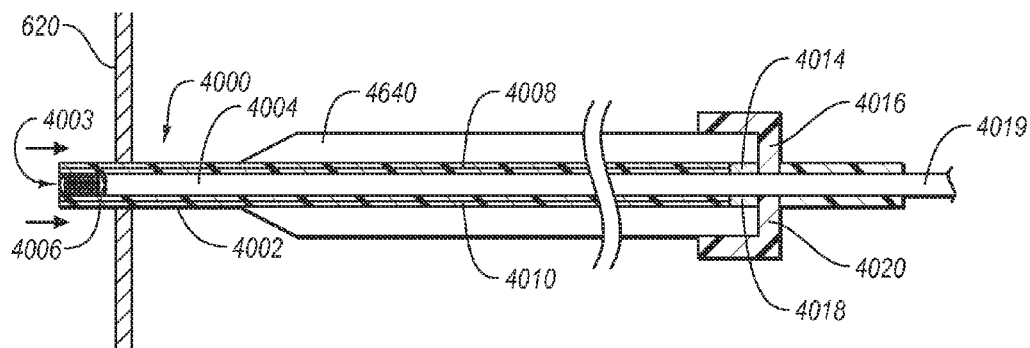
FIGS. 24A-24B illustrate an anchor system in a collapsed configuration, and which can function as a locator.
Figure 24B:
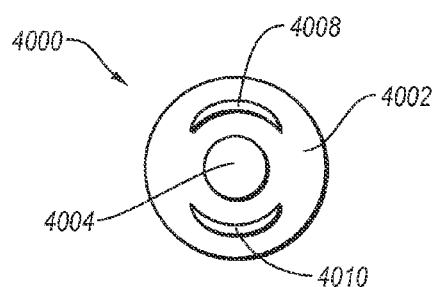

FIGS. 24A-24B illustrate an embodiment of a removable anchor system 4000. The removable anchor system 4000 can include a sheath 4640 that can be configured as any sheath or outer cover or outer tube as described herein. An anchor sheath 4002 can include a pusher member 4004, a removable anchor 4006, and the first anchor wire portion 4008 and second anchor wire portion 4010 positioned opposite of the first anchor wire. The first and second anchor wire portions 4008, 4010 as well as additional anchor wires can have equal or even spacing as well as unequal or uneven spacing with around the lumen 4003 of the anchor sheath 4002. The first anchor wire 4008 and second wire controller 4010 can be formed from the same wire. As such, the same wire forms the first and second anchor wire portions 4008, 4010 and the removable anchor 4006.

The first and second anchor wire portions 4008, 4010 (e.g., of the same wire) can traverse the lumen 4003 until reaching a first wire controller 4014 that couples with and controls the first anchor wire portion 4008 and a second wire controller 4018 that couples with and controls the second anchor wire portion 4010. The first wire controller 4014 can include a first mechanism 4014 that can automatically and/or selectively pulled to control the distal end of the first anchor wire portion 4008. A similar second mechanism 4020 can control the second wire controller 4018 and second anchor wire portion 4010.

Also, the pusher member 4004 can be operably coupled with a push member controller 4019 for selective axial motion or selective position setting.

Figure 25:
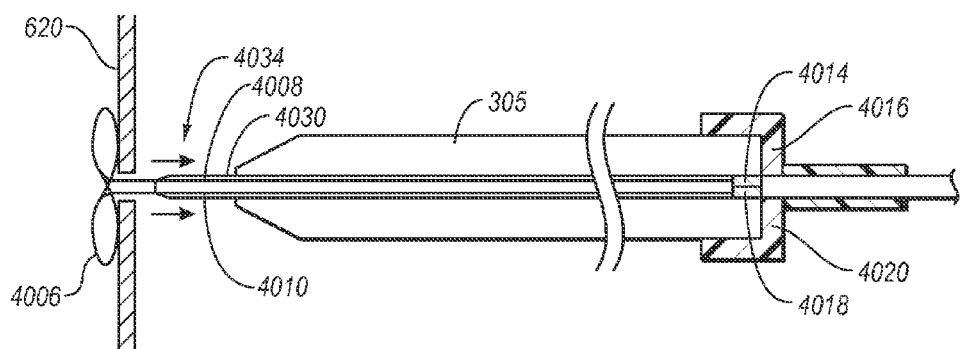
FIG. 25 illustrates an anchor system being deployed and expanded within a vessel.

Additionally, multiple wires can be used to form additional anchors similarly as formed from the first anchor wire portion 4008, second anchor wire portion 4010, and the anchor 4006. As such, while FIG. 25 shows a two lobe anchor formed from a single wire, multiple wires can be used to form multiple two lobe anchors. Alternatively, a single wire can form multiple-lobed clover shaped anchors that are all controlled by first and second anchor wire portions operated by the wire controllers.

FIG. 25 shows the removable anchor system 4000 after the removable locator 4006 at the distal end has been expanded within a blood vessel 620. In order to expand, the pusher member 4004 can be held or advanced distally compared to the relative proximal motion of the anchor sheath 4002, which is indicated by the arrows. The locator 4006 automatically expands when passed out of the anchor sheath 4002. The first and second anchor wires 4008, 4010 are shows to be pulled proximally so that the locator 4006 pushes up against the inside of the blood vessel 620. FIG. 25 also shows a hemostasis tube 4030 and an expandable hemostasis member 3034 that can expand outwardly to provide hemostasis.

The first and second mechanisms 4018, 4020 proximal end of the removable anchor system 4000 can be activated to selectively pull the first and second anchor wire portions 4008, 4010. This can include selectively pulling both the first and second anchor wire portions 4008, 4010 so that the locator 4006 is brought tight against the blood vessel 620.

Figure 26A:
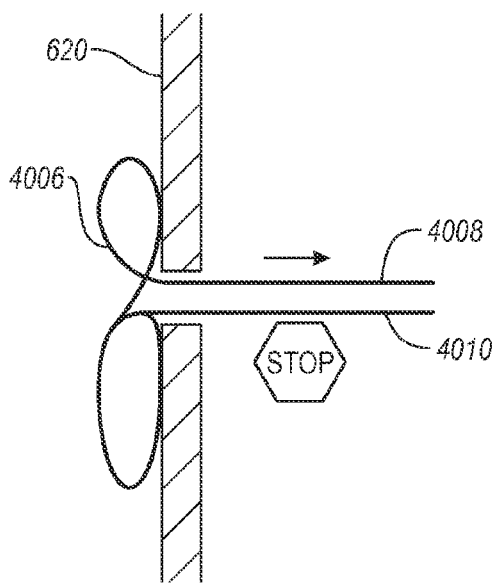
FIGS. 26A-26B show an anchor being collapsed and withdrawn.
Figure 26B:
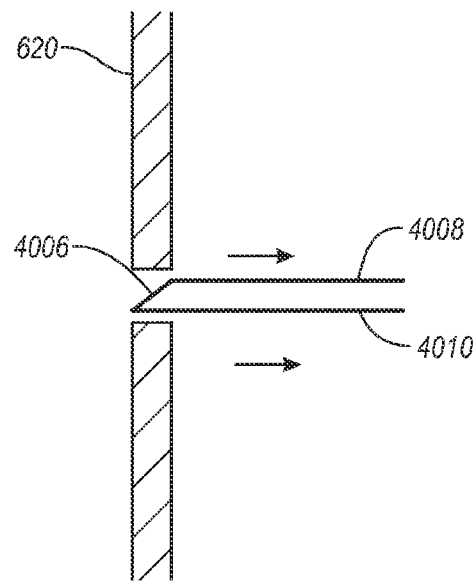

FIGS. 26A-26B show an anchor being collapsed and withdrawn. As such, the first anchor wire portion 4008 can be pulled while the second anchor wire portion 4010 is not pulled (e.g., stop) so that locator 4006 begins to collapse and be pulled proximally as shown in FIG. 26A. FIG. 26B shows the removable locator 4006 can be deformed and pulled proximally out of the blood vessel 620 by pulling one or more of the first and second anchor wire portions 4009, 4010. The removal of the removal locator 4006 can occur before or as a closure element is deployed to seal the opening 610 of the vessel 620.

Figure 27A:
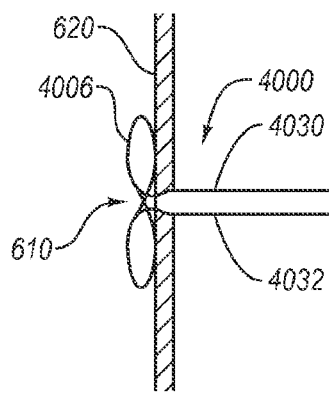
FIG. 27A-27C show an implantable "looped" anchor system being used with a carrier assembly and tube set that deploys a blood vessel closure element.
Figure 27B:
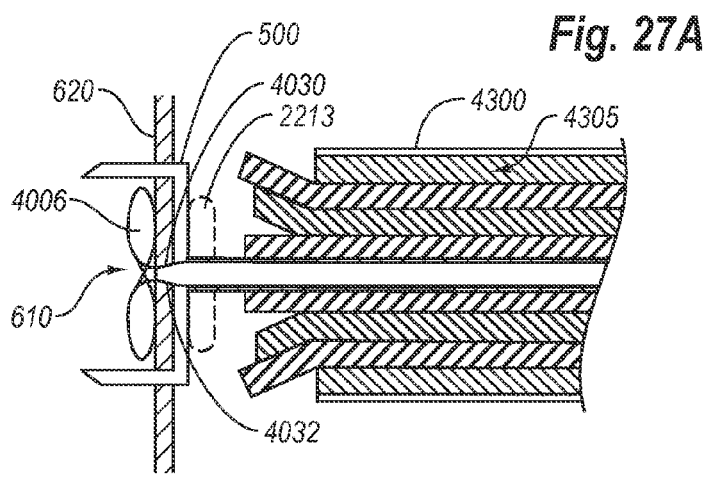
Figure 27C:
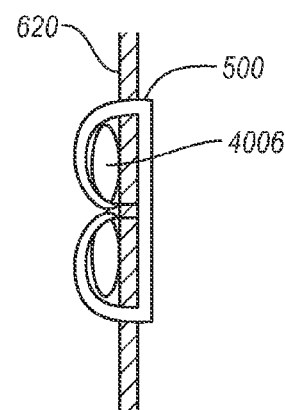

FIG. 27A-27C show an implantable, removable anchor system 4000 being used with a carrier assembly 4300 and tube set 4305 that deploys a blood vessel closure element 500 into a vessel 620. The anchor system 4000, carrier assembly 4300 and tube set 4305 can be configured as described herein.

FIG. 27A shows the anchor system 4000 being located within an opening 610 of the vessel 620. The locator 4006 is positioned against the internal surface of the vessel 620 by pulling on the first anchor wire portion 4030 and second anchor wire portion 4032 at the same time to draw the locator 4006 against the vessel 620 so as to provide the location of the vessel 620. The anchor 2006 can be opened within a blood vessel 620 as shown in the figures, and can be held by selectively pulling the first anchor wire portion 4030 and the second anchor wire portion 4032. These anchor wire portions 4030, 4032 are configured to be cut, decoupled, degraded, dissolved, or otherwise decoupled from the locator 4006. This allows for the anchor 4006 to be implanted. Optionally, the anchor 4006 can be formed of an implantable metal or plastic as well as a degradable material, such as a degradable polymer. The anchor wire portions 4030, 4032 can be prepared of materials common to suture materials as well as biocompatible polymers that are biodegradable or biostable.

FIG. 27B shows the carrier assembly 4200 and tube set 4305 being located adjacent to the opening 610 in the vessel 620, and can be positioned as described herein. As shown, the closure element 500 penetrates through the vessel 620 at a diameter wider or circumference larger than the locator 4006 after being deployed by the tube set 4305 and carrier assembly 4200. The closure element 500 can be inserted into the blood vessel 520 before, during or after the expandable hemostasis member 2213 is refracted or unexpanded as shown by the dashed lines. Accordingly, the dashed lines show the hemostasis member 2213 in the deployed and expanded orientation. The hemostasis member 2213 can be collapsed upon deployment of the closure element 500.

FIG. 27C shows the closure element 500 collapsed and returned to its natural and substantially planar shape. While the closure element 500 is collapsing, it grabs the implantable anchor 4006 and draws it against the blood vessel 620 to close the opening 610. The anchor 4006 is decoupled from the first and second anchor wires 4030, 4032.

Optionally, the closure element and/or anchor 4006 can include portions that are hemostasis, such as having a hemostatic agent coated on selected surfaces, such as non-blood flow facing surfaces or tissue facing surfaces.

Figure 28A:
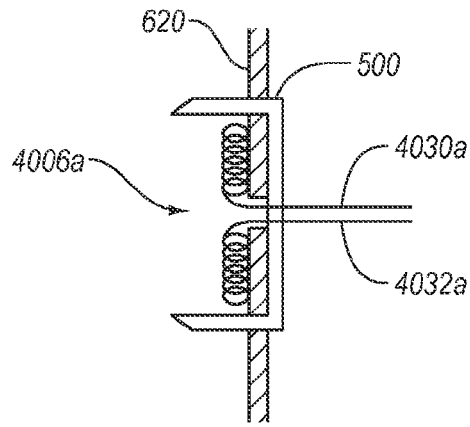
FIGS. 28A-28B show an implantable coil anchor system being implanted with a closure element.
Figure 28B:
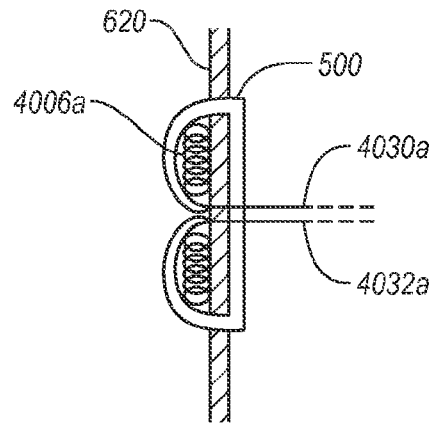
Figure 29A:
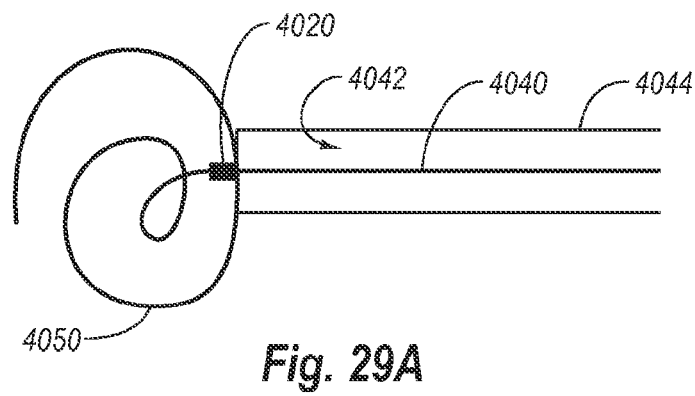
FIGS. 29A-29B show examples of removable or implantable anchors, which can be used as locators.

FIGS. 28A-28B show another embodiment of an anchor 4006a, which can be removable or implantable, in the form of a tight coil. The coiled anchor 4006a can function much as the looped anchor 4006 of FIGS. 24-28. FIG. 29A shows that the closure element 500 can reach around the edges of the coiled anchor 4006a so that it is pulled against the vessel. FIG. 28B also shows the first and second anchor wires 4030a, 4032a that are dissolvable.

FIG. 29A shows an anchor 4050 that is integrally formed with or coupled to one or more anchor wire portions 4040 via a coupler 4020. The coupler 4020 can be selectively undone or dissolved to decouple an implantable anchor 4050 from the anchor wire portion 4040. Alternatively, the coupler 4020 can couple to different materials of a removable anchor 4050 and the anchor wire portion 4040. The shape of the anchor 4050 is a spiral, and which can be delivered into a vessel and expanded as described herein. The spiral anchor 4050 can also be extracted from the blood vessel by pulling on the anchor wire 4040 so that the anchor 4050 unwinds into a lumen 4042 of a locator assembly 4044.

Figure 29B:
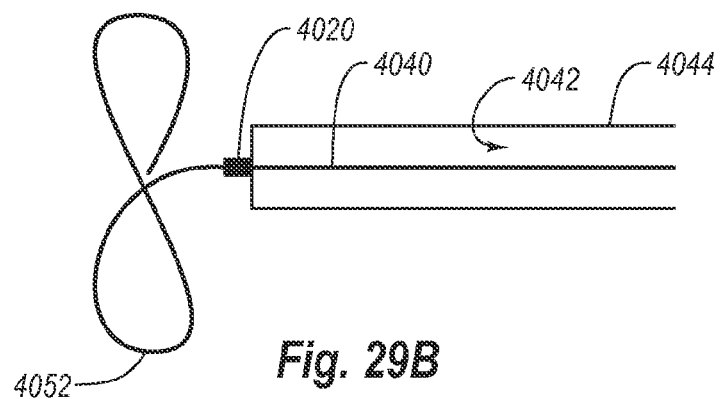

FIG. 29B shows an anchor 4052 and anchor wire portion 4040 and coupler 4020 substantially as FIG. 29A. However, the anchor 4052 has a continuous looped shape with one or more loops (shown with 2 loops). The looped anchor 4052 can be deployed and withdrawn or implanted as described herein.

Figure 30A:
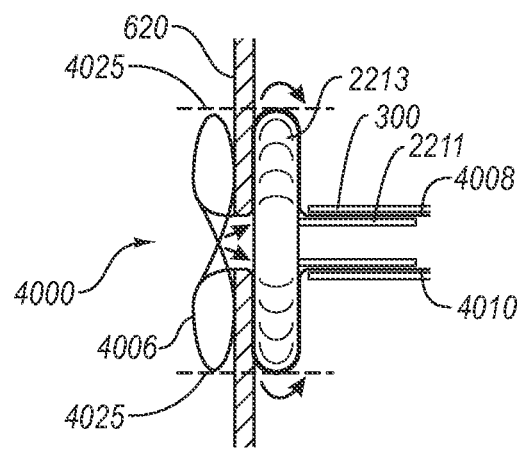
FIG. 30A shows an expanded hemostasis member and an implantable anchor cooperating to provide hemostasis.
Figure 30B:
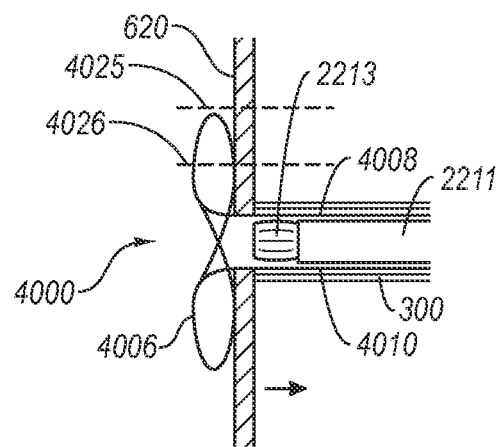
FIG. 30B shows the unexpanded hemostasis member and an implantable anchor as a closure element is about to be deployed.

FIGS. 30A-30B show an anchor system 4000 that is operated with an expandable hemostasis member 2213. The expandable hemostasis member 2213 and anchor system 4000 (removable or implantable) can be deployed and expanded as described herein. As shown, the expandable hemostasis member 2213 expands and causes the first and second anchor wire portions 4008, 4010 to be tightened and drawn against the vessel 620 so that the anchor 4006 locates and anchors against the inside of the vessel 620 while the expandable hemostasis member 2213 is pushed against the outside of the vessel 620 to provide hemostasis.

FIG. 30A shows a dashed line 4025 marking the outer diameter of the expandable hemostasis member 2213. As such, the closure element (not shown) can have a diameter larger than 4025 when deployed with the hemostasis member 2213 being expanded. Accordingly, dashed line 4025 shows the diameter of closure element when deployed around an expanded hemostasis member 2213. The closure element can then pierce the blood vessel outside or wider than the dashed line 4025. This can ensure the expandable hemostasis member 2213 can be unexpanded and withdrawn. As shown, the diameter of dashed line 4025 is also wider than the diameter of the anchor 4006 so that the closure element wraps around and encompasses the anchor 4006 upon deployment and implantation.

FIG. 30B shows an instance where the expandable hemostasis member 2213 is unexpanded before or as the closure element pierces the vessel to an unexpanded outer diameter 4026 shown by the dashed line. The dashed line 4026 shows a diameter larger than the diameter of the unexpanded hemostasis member 2213, and the closure element can have a diameter that is larger than the dashed line 4026. As such, the closure element (not shown) can have a diameter upon deployment that is larger than the diameter of the unexpanded diameter 4026 of the hemostasis member 2213. The closure element can also have a diameter that is smaller than the expanded diameter 4025 of the expanded hemostasis member 2213 and/or anchor 4006.

The anchors described herein can function as locators and can be configured with components described herein in connection to locators and locator assemblies. Also, The anchors can be prepared from shape-memory materials that are alloys or polymers, as well as metals or polymers that are implantable as well as degradable. Examples of the closure element materials can be used as the anchor materials.

The embodiments of hemostasis systems and the components for providing improved hemostasis described herein are representative of the different types of hemostasis providing elements that can be included in a device and/or system for delivering a closure element into a vessel for closing and sealing a opening therein. The hemostasis elements can be varied from that which has been illustrated and described; however, the function remains to provide improved hemostasis during the closure element delivery process. As such, the skilled artisan could make various modifications to the hemostasis elements and still provide improved hemostasis. Accordingly, some of the variations that may be employed will be discussed in more detail below.

The hemostasis system has been illustrated and described as having non-expanding portions and expanding portions. This can include a single material with portions configured to function different in the non-expanding portion compared to the expanding portion. For example, the material at the expanding portion can be narrower or less resistant to forces so as to preferentially expand compared to the non-expanding portion. The non-expanding portion could also have a non-expanding shape or solid composition without an internal lumen, such as a rod, shaft, wire, pin, and the like. Alternatively, the non-expanding portion can be configured identically with the expanding portion, and the hemostasis system includes a member that confines the non-expanding portion so as to inhibit expansion. For example, the sheath can be retracted enough to only expose the expanding portion, and thereby allow the expanding portion to expand while retaining the non-expanding within the sheath such that contact between the sheath and the non-expanding portion inhibits expansion. A similar configuration can be applied with different materials for the non-expanding portion and the expanding portion, where the material of the non-expanding portion is coupled to the material of the expanding portion. Additionally, the non-expanding portion can have a material or plurality of materials that are different from the material or plurality of materials of the expanding portion. For example, the non-expanding portion can have a structurally reinforcing member, such as rod, ribs, braces, or the like that inhibit expansion. On the other hand, the expandable portion can have expandable members (e.g., shape memory materials) disposed in a polymeric member that is capable of expanding, whereby the expandable members cause the polymeric member to correspondingly expand.

In the instance the non-expanding portion and the expanding portion are different materials coupled together, such coupling can be accomplished by well known methods for attaching a material to another material. The type of coupling employed can depend on the type of the first material and the second material. For example, the coupling can be achieved by adhesive, melt-bonding, sintering, welding, brazing, threading, friction resistance, and the like.

In one example, the expandable member can include a laminate structure having structural elements that can be expanded, and thereby expand the laminate structure. The structural elements that can expand can be configured similarly to a stent that expands when deployed. Thus, the hemostasis system can include the components of a stent delivery system that are used to expand a stent, which can include self-expanding systems, balloon/bladder expanding systems, and the like.

The materials of the hemostasis system can be varied and still retain the same function. Generally, the hemostasis materials are biocompatible so that adverse physiological reactions do not occur when the expandable member expands to contact and plug the opening in the vessel. Such biocompatible materials can include metals, alloys, superelastic alloys (e.g., shape memory alloys) polymers, plastics, foams, elastomers, natural or synthetic rubbers, ceramics, and combinations thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of closing an opening in a body lumen of a subject, the method comprising:
   providing a medical device having an expandable hemostasis member;
   locating the body lumen with a locator;
   expanding the expandable hemostasis member to conform to the wall of the body lumen so as to create hemostasis across the opening while the expandable hemostasis member is expanded; and
   deploying a closure element having a plurality of tines tapering toward a distal end into the body lumen so as to close the opening and create hemostasis while the closure element is deployed.

2. The method of claim 1, further comprising expanding the locator from an unexpanded state to an expanded state and pulling the locator against the internal surface of the body lumen.

3. The method of claim 1, wherein the locator automatically expands when moved out from tube of a locator assembly.

4. The method of claim 1, further comprising deploying the locator in an expanded such that the locator remains within the body lumen in the expanded after the medical device is removed from the body lumen.

5. The method of claim 4, wherein deployment of the closure element traps the implantable locator adjacent to the internal surface of the body lumen.

6. The method of claim 4, wherein the locator assembly includes a suture coupled to the implantable locator, and the suture is cut after the opening of the body lumen is closed.

7. The method of claim 6, wherein the suture is biodegradable and any portion of the suture remaining in the subject degrades.

8. The method of claim 1, wherein the locator is biodegradable.

9. The method of claim 1, further comprising contracting the expanded locator or expanded expandable hemostasis member upon deployment of the closure element.

10. The method of claim 1, further comprising a locator assembly that includes at least a first wire portion and a second wire portion that are integrated or coupled to the locator such that pulling on both the first wire portion and second wire portion draws the locator against the internal surface of the body lumen, and puling on one of the first wire portion or second wire portion unwinds the locator and withdraws the locator from the body lumen.

11. The method of claim 1, wherein said expandable hemostasis member in an unexpanded state has a cross-section that is less than or substantially equal to a cross-section of said opening.

12. The method of claim 1, wherein said expandable hemostasis member in an expanded state has a cross-section that is greater than or substantially equal to a cross-section of said opening.

13. The method of claim 1, further comprising longitudinally compressing the expandable hemostasis member so as to laterally expand said expandable hemostasis member.

14. A method of closing an opening in a side of a body lumen of a subject, the method comprising:
- providing a medical device for delivering a closure element to a wall of an opening formed in a body lumen with improved hemostasis, the medical device comprising:
  - a locator assembly having a distal locator configured to extend through tissue into the opening and expand to selectively engage an internal surface of the body lumen adjacent to the opening so as to provide a desired position of the medical device relative to the body lumen;
  - a hemostasis assembly associated with the locator assembly, the hemostasis assembly having a selectively expandable hemostasis member on a distal end configured to extend to the opening when the locator assembly is in contact with the internal surface of the body lumen, the expandable hemostasis member being configured to expand laterally when disposed at the opening so as to provide hemostasis; and
  - a carrier assembly being slidably associated with the locator assembly and hemostasis assembly, the carrier assembly having a carrier member supporting the closure element and a cover member retaining the closure element within the carrier assembly, the closure element including a plurality of tissue piercing tines tapering toward a distal end, the carrier assembly being configured to position the closure element adjacent to the opening and being configured to distally deploy the closure element into tissue surrounding the opening of the body lumen such that the body lumen is drawn substantially closed;
- locating the body lumen with the distal locator;
- expanding the expandable hemostasis member to conform to the wall of the body lumen so as to create hemostasis across the opening while the expandable hemostasis member is expanded; and
- deploying the closure element into the body lumen so as to close the opening and create hemostasis while the closure element is deployed.

* * * * *